US006869975B2

(12) United States Patent
Abe et al.

(10) Patent No.: US 6,869,975 B2
(45) Date of Patent: Mar. 22, 2005

(54) LINKED BIARYL COMPOUNDS

(75) Inventors: Hiroyuki Abe, Osaka (JP); Jonathan Houze, San Mateo, CA (US); Hisashi Kawasaki, Osaka (JP); Frank Kayser, San Francisco, CA (US); Rajiv Sharma, Fremont, CA (US); Samuel Sperry, San Diego, CA (US)

(73) Assignees: Tularik Inc., South San Francisco, CA (US); Japan Tobacco, Inc., Tokyo (JP)

( * ) Notice: Subject to any disclaimer, the term of this patent is extended or adjusted under 35 U.S.C. 154(b) by 0 days.

(21) Appl. No.: 10/244,063

(22) Filed: Sep. 13, 2002

(65) Prior Publication Data

US 2003/0149108 A1 Aug. 7, 2003

Related U.S. Application Data

(60) Provisional application No. 60/386,833, filed on Jun. 6, 2002, provisional application No. 60/378,627, filed on May 7, 2002, provisional application No. 60/335,434, filed on Nov. 30, 2001, and provisional application No. 60/322,556, filed on Sep. 14, 2001.

(51) Int. Cl.⁷ ............................................... A01N 37/10
(52) U.S. Cl. ....................... 514/568; 514/569; 562/426; 562/427
(58) Field of Search ............................... 514/568, 569; 562/426, 427

(56) References Cited

U.S. PATENT DOCUMENTS

| 4,443,536 A | * | 4/1984 | Lestina ........................ 430/552 |
| 4,466,902 A | | 8/1984 | Kumagae et al. |
| 5,847,008 A | | 12/1998 | Doebber et al. |
| 5,859,051 A | | 1/1999 | Adams et al. |
| 6,090,839 A | | 7/2000 | Adams et al. |
| 6,156,801 A | * | 12/2000 | Ota et al. .................... 514/646 |
| 6,300,364 B1 | | 10/2001 | Shimokawa et al. |
| 6,525,094 B1 | | 2/2003 | Zhang et al. |

FOREIGN PATENT DOCUMENTS

| WO | WO 96/01317 | 1/1996 | |
| WO | WO 97/27857 | 8/1997 | |
| WO | WO 97/28115 | 8/1997 | |
| WO | WO 97/28137 | 8/1997 | |
| WO | WO 97/28149 | 8/1997 | |
| WO | WO 98/ 43943 | * 10/1998 | ......... C07C/217/86 |
| WO | WO 99/04815 | 2/1999 | |
| WO | WO99/38845 | 8/1999 | |
| WO | WO 00/72812 | 12/2000 | |
| WO | WO 00/78312 A1 | 12/2000 | |
| WO | WO01/00579 | 1/2001 | |
| WO | WO 01/00603 A1 | 1/2001 | |
| WO | WO 02/08188 A1 | 1/2001 | |
| WO | WO 01/17994 A1 | 3/2001 | |
| WO | WO 01/016120 A1 | 3/2001 | |
| WO | WO 01/60807 A1 | 8/2001 | |
| WO | WO 01/79197 A1 | 10/2001 | |
| WO | WO01/82916 | 11/2001 | |
| WO | WO 01/96311 A2 | 12/2001 | |
| WO | WO 01/96347 A1 | 12/2001 | |
| WO | WO02/00633 | 1/2002 | |
| WO | WO 02/14291 A1 | 2/2002 | |
| WO | WO 02/28433 A1 | 4/2002 | |
| WO | WO 02/28434 | 4/2002 | |
| WO | WO 02/28434 A2 | 4/2002 | |
| WO | WO 02/50048 A1 | 6/2002 | |
| WO | WO 02/070011 A2 | 9/2002 | |
| WO | WO 02/076957 A1 | 10/2002 | |
| WO | WO 03/084916 A2 | 10/2003 | |

OTHER PUBLICATIONS

Auwerx et al., 1996, "Transcriptional control of triglyceride metabolism: fibrates and fatty acids change the expression of the LPL and apo C–III genes by activating the nuclear receptor PPAR", Atherosclerosis 124(suppl.):S29–S37.

Berge et al., 1977, "Pharmaceutical salts", J. Pharmaceut. Sci. 66:1–19.

Bisgaier and Pape, 1998, "High density lipoprotein: are elevated levels desirable and achievable?", Curr. Pharmaceut. Des. 4:53–70.

Hartwig, 1998, "Carbon–heteroatom bond–forming reductive eliminations of amines, ethers, and sulfides", Acc. Chem. Res. 31:852–860.

He et al., 1999, "PPARδ is an APC–regulated target of nonsteriodal anti–inflammatory drugs", Cell 99:335–345.

Johnson et al., 1998, "Troglitazone: review and assessment of its role in the treatment of patients with impaired glucose tolerance and diabetes mellitus", Ann. Pharmacother.32:337–348.

Kelley and Killian, 1998, "Troglitazone", Curr. Opin. Endocrinol. Diabetes 5:90–96.

Kita et al., 1995, "Novel and direct nucleophilic sulfenylation and thiocyanation of phenol ethers using a hypervalent iodine (III) reagent", J. Org. Chem. 60:7144–7148.

Lefebvre et al., 1997, "Regulation of lipoprotein metabolism by thiazolidinediones occurs through a distinct but complementary mechanism relative to fibrates", Arterioscler. Thromb. Vasc. Biol. 17:1756–1764.

Lehmann et al., 1995, "An antidiabetic thiazolidinedione is a high affinity ligand for peroxisome proliferator–activated receptor γ (PPARγ)", J. Biol. Chem. 270:12953–12956.

Leutenegger et al., 1997, "Double–masked, placebo–controlled, dose–ranging study of troglitazone 10 to 200 mg once daily in non–insulin–dependent diabetes mellitus", Curr. Therapeut. Res. 58:403–416.

(List continued on next page.)

Primary Examiner—Zinna Northington Davis
(74) Attorney, Agent, or Firm—Jones Day

(57) ABSTRACT

Compounds, compositions and methods that are useful for the treatment of metabolic disorders, inflammatory diseases and cancer are provided herein. In particular, the invention provides compounds which modulate the expression and/or function of proteins involved in lipid metabolism, inflammation and cell proliferation. The subject compounds are linked biaryl compounds.

28 Claims, 2 Drawing Sheets

OTHER PUBLICATIONS

Oliver et al., 2001, "A selective peroxisome proliferator–activated receptor δ agonist promotes reverse cholesterol transport", Proc. Natl. Acad. Sci. USA 98:5306–5311.

Palomo et al., 2000, "Phosphazene bases for the preparation of biaryl thioethers from aryl iodides and arenethiols", Tetrahedron Lett. 41:1283–1286.

Patani and LaVoie, 1996, "Bioisosterism: a rational approach in drug design", Chem. Rev. 96:3147–3176.

Staels and Auwerx, 1997, "Role of PPAR in the pharmacological regulation of lipoprotein metabolism by fibrates and thiazolidinediones", Curr. Pharmaceut. Des. 3:1–14.

* cited by examiner

LINKED BIARYL COMPOUNDS

CROSS-REFERENCE TO RELATED APPLICATIONS

This application is related to and claims the benefit of U.S. application Ser. No. 60/386,833, filed Jun. 6, 2002, U.S. application Ser. No. 60/378,627, filed May 7, 2002, U.S. application Ser. No. 60/335,434, filed Nov. 30, 2001, and U.S. application Ser. No. 60/322,556, filed Sep. 14, 2001, the disclosures of which are incorporated by reference herein.

FIELD OF THE INVENTION

The present invention relates to compounds that are useful in the diagnosis and treatment of metabolic disorders, inflammatory diseases and neoplastic diseases, and complications thereof.

BACKGROUND OF THE INVENTION

Several independent risk factors have been associated with cardiovascular disease. These include hypertension, increased fibrinogen levels, high levels of triglycerides, elevated low density lipoprotein (LDL) cholesterol, elevated total cholesterol, and low levels of high density lipoprotein (HDL) cholesterol. HMG CoA reductase inhibitors (e.g., statins) are useful for treating conditions characterized by high LDL cholesterol levels. It has been shown that lowering LDL cholesterol is not sufficient for reducing the risk of cardiovascular disease in some patients, particularly those with normal LDL cholesterol levels. This population pool is identified by the independent risk factor of low HDL cholesterol. The increased risk of cardiovascular disease associated with low HDL cholesterol levels has not yet been successfully addressed by drug therapy (i.e., currently there are no drugs on the market that are useful for raising HDL cholesterol). See, e.g., Bisgaier et al. (1998) *Curr. Pharm. Des.* 4:53–70.

Targets for the development of therapeutic agents for cardiovascular disease, diseases associated with cardiovascular disease, such as syndrome X (including metabolic syndrome), and other pathologies such as, diabetes, obesity and cancer include transcription factors involved in regulating lipid metabolism and homeostasis.

The peroxisome proliferator-activated receptors (PPARs) are transducer proteins belonging to the steroid/thyroid/retinoid receptor superfamily. The PPARs were originally identified as orphan receptors, without known ligands, but were named for their ability to mediate the pleiotropic effects of fatty acid peroxisome proliferators. Three mammalian PPARs have been isolated: PPARγ, PPARα and PPARδ (PPARβ, NUC1). These receptors function as ligand-regulated transcription factors that control the expression of target genes by binding to their responsive DNA sequence as heterodimers with RXR. The target genes encode enzymes involved in lipid metabolism and differentiation of adipocytes.

PPARγ has been shown to be expressed in an adipose tissue-specific manner. Its expression is induced early during the course of differentiation of several preadipocyte cell lines. Additional research has now demonstrated that PPARγ plays a pivotal role in the adipogenic signaling cascade. PPARγ also regulates the ob/leptin gene which is involved in regulating energy homeostasis and adipocyte differentiation, which has been shown to be a critical step to be targeted for anti-obesity and diabetic conditions.

In an effort to understand the role of PPARγ in adipocyte differentiation, several investigators have focused on the identification of PPARγ activators. One class of compounds, the thiazolidinediones, which were known to have adipogenic effects on preadipocyte and mesenchymal stem cells in vitro, and antidiabetic effects in animal models of non-insulin-dependent diabetes mellitus (NIDDM), were also demonstrated to be PPARγ-selective ligands (Lehmann et al. (1995) *J. Biol. Chem.* 270:12953–12956). More recently, compounds that selectively activate murine PPARγ were shown to possess in vivo anti-diabetic activity in mice.

Activators of PPARγ, such as troglitazone, have been shown in the clinic to enhance insulin action, reduce serum glucose and have small but significant effects on reducing serum triglyceride levels in patients with NIDDM diabetes. See, for example, Kelly et al. (1998) *Curr. Opin. Endocrinol Diabetes* 5(2):90–96, Johnson et al. (1997) *Ann. Pharmacother.* 32(3):337–348 and Leutenegger et al. (1997) *Curr. Ther. Res.* 58(7):403–416. The mechanism for this triglyceride lowering effect appears to be predominantly increased clearance of very low density lipoproteins (VLDL) through induction of lipoprotein lipase (LPL) gene expression. See, for example, B. Staels et al. (1997) *Arterioscler. Thromb. Vasc. Biol.* 17(9):1756–1764.

Fibrates are a class of drugs which may lower serum triglycerides by 20–50%, lower LDL cholesterol by 10–15%, shift the LDL particle size from the more atherogenic small dense to normal dense LDL, and increase HDL cholesterol by 10–15%. Experimental evidence indicates that the effects of fibrates on serum lipids are mediated through activation of PPARα. See, for example, Staels et al. (1997) *Pharm. Des.* 3(1):1–14. Activation of PPARα results in transcription of enzymes that increase fatty acid catabolism and decrease de novo fatty acid synthesis in the liver resulting in decreased triglyceride synthesis and VLDL production/secretion. In addition, PPARα activation decreases production of apoC-III. Reduction in apoC-III, an inhibitor of LPL activity, increases clearance of VLDL. See, for example, Auwerx et al. (1996) *Atherosclerosis, (Shannon, Irel.)*124(Suppl.):S29–S37.

Evidence suggests that PPARδ also controls the peroxisomal beta-oxidation pathway of fatty acids. Activators of PPARδ have been shown to promote reverse cholesterol transport, which can raise HDL cholesterol levels. See, Oliver et al. (2001) *Proc. Natl Acad. Sci. USA* 98(9):5306–531 1. It has also been shown that PPARδ activators inhibit the formation of the inflammatory mediator's inducible nitric oxide synthase (iNOS) and tumor necrosis factor (TNF). See, International Publication No. WO 02/28434 to Buchan et al. Moreover, it has been shown that PPARδ, unlike PPARγ or PPARα, represents a β-catenin/Tcf-4 target with particular importance for chemoprevention (He et al. (1999) *Cell* 99:335–345).

The identification of compounds which modulate PPARδ provides an opportunity to probe PPARδ-mediated processes and discover new therapeutic agents for conditions and diseases associated therewith, such as cardiovascular disease, atherosclerosis, diabetes, obesity, syndrome X and malignant diseases.

SUMMARY OF THE INVENTION

The present invention provides compounds which are useful in the treatment of metabolic disorders, cardiovascular diseases, inflammatory conditions and neoplastic diseases. While a complete understanding of the compounds' mechanism of action is not required in order to practice the present invention, the compounds have been shown to exert their effect through modulation of PPARδ. The invention also provides pharmaceutical compositions comprising these compounds and methods of using the subject compounds and compositions for the treatment of metabolic disorders, cardiovascular disease, inflammatory conditions or neoplastic diseases.

The compounds provided herein have the formula (Ia):

$$R^1O_2C—CR^aR^b—Y—Ar^1—X—Ar^2—Z^1—Z^2—Ar^3 \quad \text{Ia}$$

wherein

X is selected from the group consisting of O, $S(O)_m$, CR'R" and $SO_2NR"$;

Y is O or CR'R";

$Z^1$ and $Z^2$ are independently selected from the group consisting of O, $S(O)_m$, $(CR'R")_n$, N(R"), C(O)NR" and CR'R"C(O)NR'";

alternatively, $Z^1$ and $Z^2$ may be combined to form $(C_2-C_4)$alkenyl;

$Ar^1$ and $Ar^2$ are independently an aromatic group;

$Ar^3$ is aryl;

each R', R" and R'" is independently selected from the group consisting of hydrogen, $(C_1-C_4)$alkyl, aryl and aryl$(C_1-C_4)$alkyl;

$R^1$ is selected from the group consisting of hydrogen, $(C_1-C_8)$alkyl and aryl$(C_1-C_4)$alkyl;

$R^a$ and $R^b$ are independently selected from the group consisting of hydrogen, $(C_1-C_4)$alkyl, aryl and aryl$(C_1-C_4)$alkyl;

the subscript m is an integer from 0 to 2; and the subscript n is an integer from 1 to 2;

with the proviso that said compound is not 3-amino-4-[4-(phenylmethoxy)phenoxy]phenoxylacetic acid, 4-[3,5-diiodo-4-(phenylmethoxy)phenoxy]-3,5-diiodobenzenepropanoic acid or 4-[4-(benzyloxy)-3-iodophenoxy]-3,5-diiodohydrocinnamic acid.

Also provided herein are compounds having the formula (Ib):

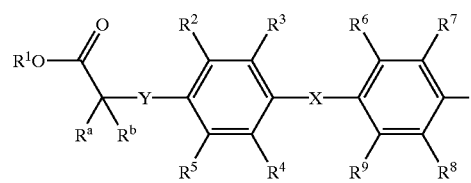

wherein

X is selected from the group consisting of O, $S(O)_m$, CR'R" and $SO_2NR"$;

Y is O or CR'R";

$Z^1$ and $Z^2$ are independently selected from the group consisting of O, $S(O)_m$, $(CR'R")_n$, N(R"), C(O)NR" and CR'R"C(O)NR'";

alternatively, $Z^1$ and $Z^2$ may be combined to form $(C_2-C_4)$alkenyl;

$Ar^3$ is aryl;

$R^1$ is selected from the group consisting of hydrogen, $(C_1-C_8)$alkyl and aryl$(C_1-C_4)$alkyl;

$R^2$, $R^3$, $R^4$, $R^5$, $R^6$, $R^7$, $R^8$ and $R^9$ are independently selected from the group consisting of hydrogen, halogen, $(C_1-C_4)$alkyl, $(C_5-C_6)$cycloalkyl, fluoro$(C_1-C_4)$alkyl, OR', aryl, aryl$(C_1-C_4)$alkyl, $NO_2$, NR'R", C(O)R', $CO_2R'$, C(O)NR'R", N(R")C(O)R', N(R")$CO_2R'$, N(R")C(O)NR'R", $S(O)_m$ NR'R", $S(O)_mR'$, CN and N(R")S(O)$_mR'$;

alternatively, any two adjacent R groups selected from the group consisting of $R^2$, $R^3$, $R^4$, $R^5$, $R^6$, $R^7$, $R^8$ and $R^9$ may be combined with the carbon atoms to which they are attached to form a fused aromatic or cycloalkane ring;

each R', R" and R'" is independently selected from the group consisting of hydrogen, $(C_1-C_4)$alkyl, aryl and aryl$(C_1-C_4)$alkyl;

alternatively, when R' and R" are attached to the same nitrogen atom, R' and R" may be combined with the nitrogen atom to form a 5-, 6- or 7-membered ring containing from 1 to 3 heteroatoms selected from the group consisting of N, O and S;

$R^a$ and $R^b$ are independently selected from the group consisting of hydrogen, $(C_1-C_4)$alkyl, aryl and aryl$(C_1-C_4)$alkyl;

the subscript m is an integer from 0 to 2; and the subscript n is an integer from 1 to 2;

with the proviso that when X is O, $Z^1$ is O, $Z^2$ is $CH_2$ and $Ar^3$ is unsubstituted phenyl, Y is other than O or $CH_2$.

Also provided herein are compounds having the formula (Ib):

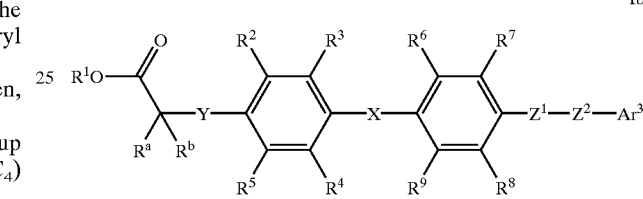

wherein

X is selected from the group consisting of $S(O)_m$, CR'R" and $SO_2NR"$;

Y is O or CR'R";

$Z^1$ and $Z^2$ are independently selected from the group consisting of O, $S(O)_m$, $(CR'R")_n$, N(R"), C(O)NR" and CR'R"C(O)NR'";

alternatively, $Z^1$ and $Z^2$ may be combined to form $(C_2-C_4)$alkenyl;

$Ar^3$ is aryl;

$R^1$ is selected from the group consisting of hydrogen, $(C_1-C_8)$alkyl and aryl$(C_1-C_4)$alkyl;

$R^2$, $R^3$, $R^4$, $R^5$, $R^6$, $R^7$, $R^8$ and $R^9$ are independently selected from the group consisting of hydrogen, halogen, $(C_1-C_4)$alkyl, $(C_5-C_6)$cycloalkyl, fluoro$(C_1-C_4)$alkyl, OR', aryl, aryl$(C_1-C_4)$alkyl, $NO_2$, NR'R", C(O)R', $CO_2R'$, C(O)NR'R", N(R")C(O)R', N(R")$CO_2R'$, N(R")C(O)NR'R", $S(O)_m$ NR'R", $S(O)_mR'$, CN and N(R")S(O)$_mR'$;

alternatively, any two adjacent R groups selected from the group consisting of $R^2$, $R^3$, $R^4$, $R^5$, $R^6$, $R^7$, $R^8$ and $R^9$ may be combined with the carbon atoms to which they are attached to form a fused aromatic or cycloalkane ring;

each R', R" and R'" is independently selected from the group consisting of hydrogen, $(C_1-C_4)$alkyl, aryl and aryl$(C_1-C_4)$alkyl;

alternatively, when R' and R" are attached to the same nitrogen atom, R' and R" may be combined with the nitrogen atom to form a 5-, 6- or 7-membered ring containing from 1 to 3 heteroatoms selected from the group consisting of N, O and S;

$R^a$ and $R^b$ are independently selected from the group consisting of hydrogen, $(C_1-C_4)$alkyl, aryl and aryl$(C_1-C_4)$alkyl;

the subscript m is an integer from 0 to 2; and the subscript n is an integer from 1 to 2.

The compounds provided in the above formulas are meant to include all pharmaceutically acceptable salts, hydrates, solvates and prodrugs thereof.

Certain pharmaceutical compositions of the invention comprise a pharmaceutically acceptable carrier, excipient or diluent in combination with a compound of formula (Ia):

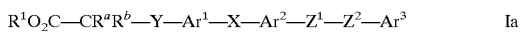
$$R^1O_2C\!-\!CR^aR^b\!-\!Y\!-\!Ar^1\!-\!X\!-\!Ar^2\!-\!Z^1\!-\!Z^2\!-\!Ar^3 \qquad \text{Ia}$$

wherein

X is selected from the group consisting of O, $S(O)_m$, CR'R" and $SO_2NR$";

Y is O or CR'R";

$Z^1$ and $Z^2$ are independently selected from the group consisting of O, $S(O)_m$, $(CR'R")_n$, N(R"), C(O)NR" and CR'R"C(O)NR'";

alternatively, $Z^1$ and $Z^2$ may be combined to form $(C_2-C_4)$alkenyl;

$Ar^1$ and $Ar^2$ are independently an aromatic group;

$Ar^3$ is aryl;

each R', R" and R'" is independently selected from the group consisting of hydrogen, $(C_1-C_4)$alkyl, aryl and aryl$(C_1-C_4)$alkyl;

$R^1$ is selected from the group consisting of hydrogen, $(C_1-C_8)$alkyl and aryl$(C_1-C_4)$alkyl;

$R^a$ and $R^b$ are independently selected from the group consisting of hydrogen, $(C_1-C_4)$alkyl, aryl and aryl$(C_1-C_4)$alkyl;

the subscript m is an integer from 0 to 2; and the subscript n is an integer from 1 to 2.

Also provided herein are pharmaceutical compositions comprising a pharmaceutically acceptable carrier, excipient or diluent in combination with a compound of formula (Ib):

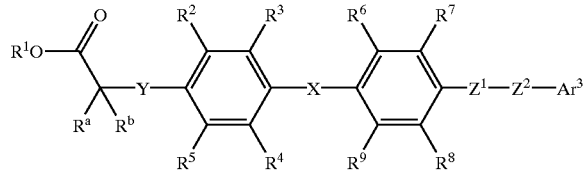

Ib wherein

X is selected from the group consisting of O, $S(O)_m$, CR'R" and $SO_2NR$";

Y is O or CR'R";

$Z^1$ and $Z^2$ are independently selected from the group consisting of O, $S(O)_m$, $(CR'R")_n$, N(R"), C(O)NR" and CR'R"C(O)NR'";

alternatively, $Z^1$ and $Z^2$ may be combined to form $(C_2-C_4)$alkenyl;

$Ar^3$ is aryl;

$R^1$ is selected from the group consisting of hydrogen, $(C_1-C_8)$alkyl and aryl$(C_1-C_4)$alkyl;

$R^2$, $R^3$, $R^4$, $R^5$, $R^6$, $R^7$, $R^8$ and $R^9$ are independently selected from the group consisting of hydrogen, halogen, $(C_1-C_4)$alkyl, $(C_5-C_6)$cycloalkyl, fluoro$(C_1-C_4)$alkyl, OR', aryl, aryl$(C_1-C_4)$alkyl, $NO_2$, NR'R", C(O)R', $CO_2R$', C(O)NR'R", N(R")C(O)R', N(R")$CO_2R$', N(R")C(O)NR'R", $S(O)_m$ NR'R", $S(O)_mR$', CN and N(R")$S(O)_mR$';

alternatively, any two adjacent R groups selected from the group consisting of $R^2$, $R^3$, $R^4$, $R^5$, $R^6$, $R^7$, $R^8$ and $R^9$ may be combined with the carbon atoms to which they are attached to form a fused aromatic or cycloalkane ring;

each R', R" and R'" is independently selected from the group consisting of hydrogen, $(C_1-C_4)$alkyl, aryl and aryl$(C_1-C_4)$alkyl;

alternatively, when R' and R" are attached to the same nitrogen atom, R' and R" may be combined with the nitrogen atom to form a 5-, 6- or 7-membered ring containing from 1 to 3 heteroatoms selected from the group consisting of N, O and S; and $R^a$ and $R^b$ are independently selected from the group consisting of hydrogen, $(C_1-C_4)$alkyl, aryl and aryl$(C_1-C_4)$alkyl;

the subscript m is an integer from 0 to 2; and the subscript n is an integer from 1 to 2.

Also provided herein are methods for treating a metabolic disorder, cardiovascular disease, an inflammatory condition, a neoplastic disease, an immune disorder, a shock state, a disorder of gastrointestinal motility or a disease of the central nervous system comprising administering to a subject in need thereof a therapeutically effective amount of one of the foregoing compounds or compositions.

The invention also provides methods for treating a condition or disease mediated by PPARδ and methods for treating a condition or disease responsive to PPARδ modulation.

The invention also provides methods for treating a condition or disease mediated by iNOS or TNF and methods for treating a condition or disease responsive to iNOS or TNF modulation.

The invention also provides methods for elevating HDL cholesterol levels.

The invention also provides methods for decreasing LDL cholesterol levels.

The invention further provides methods for decreasing triglyceride levels.

The invention provides methods for treating diabetes, atherosclerosis or conditions associated with syndrome X, decreasing insulin resistance, lowering blood pressure, and obesity.

The present invention also provides methods for modulating PPARδ.

DETAILED DESCRIPTION OF THE INVENTION

Abbreviations and Definitions

Figure 1A:
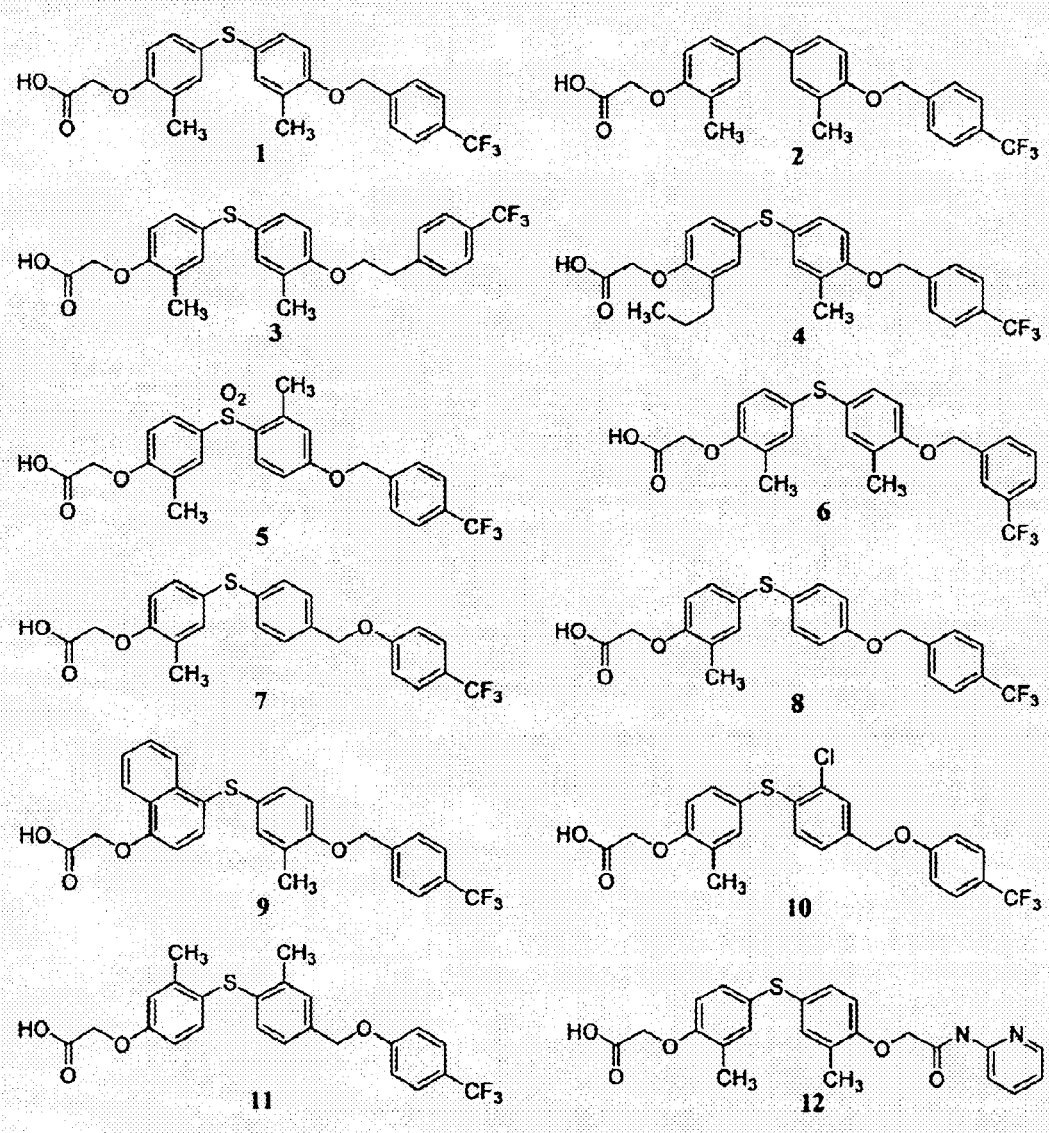
FIGS. 1a and 1b provide exemplary structures of preferred compounds of the invention.

The abbreviations used herein are conventional, unless otherwise defined.

The terms "treat", "treating" and "treatment", as used herein, are meant to include:

(1) alleviating or abrogating a disease and/or its attendant symptoms;

(2) barring a subject from acquiring a disease;

(3) reducing a subject's risk of acquiring a disease;

(4) decreasing the probability or eliminating the possibility that a disease will be contracted;

(5) preventing the disease, i.e., causing the clinical symptoms of the disease not to develop in a mammal that may be exposed to or predisposed to the disease but does not yet experience or display symptoms of the disease;

(6) inhibiting the disease, i.e., arresting or reducing the development of the disease or its clinical symptoms; or (7) relieving the disease, i.e., causing regression of the disease or its clinical symptoms.

The term "therapeutically effective amount" refers to that amount of the compound being administered sufficient to prevent development of or alleviate to some extent one or more of the symptoms of the condition or disorder being treated as well as to alleviate or eradicate the cause of the disease itself.

The term "modulate" refers to the ability of a compound to increase or decrease the function and/or expression of PPARδ, where PPARδ function may include transcription regulatory activity and/or protein-binding. Modulation may occur in vitro or in vivo. Modulation, as described herein, includes antagonism, agonism, partial antagonism and/or partial agonism of a function or characteristic associated with PPARδ, either directly or indirectly, and/or the upregulation or downregulation of PPARδ expression, either directly or indirectly. Agonists are compounds that, e.g., bind to, stimulate, increase, open, activate, facilitate, enhance activation, activate, sensitize or upregulate signal transduction. Antagonists are compounds that, e.g., bind to, partially or totally block stimulation, decrease, prevent, inhibit, delay activation, inactivate, desensitize, or downregulate signal transduction. A modulator preferably inhibits PPARδ function and/or downregulates PPARδ expression. More preferably, a modulator inhibits or activates PPARδ function and/or downregulates or upregulates PPARδ expression. Most preferably, a modulator activates PPARδ function and/or upregulates PPARδ expression. In addition, in a preferred embodiment, the modulation is direct. The ability of a compound to inhibit PPARδ function can be demonstrated in a binding assay or a cell-based assay, e.g., a transient transfection assay.

As used herein, "diabetes" refers to type I diabetes mellitus (juvenile onset diabetes, insulin dependent-diabetes mellitus or IDDM) or type II diabetes mellitus (non-insulin-dependent diabetes mellitus or NIDDM), preferably, NIDDM.

As used herein, "syndrome X" refers to a collection of abnormalities including hyperinsulinemia, obesity, elevated levels of triglycerides, uric acid, fibrinogen, small dense LDL particles and plasminogen activator inhibitor 1 (PAI-1), and decreased levels of HDL cholesterol. Syndrome X is further meant to include metabolic syndrome.

As used herein, the term "eating disorder" refers to an emotional and/or behavioral disturbance associated with an excessive decrease in body weight and/or inappropriate efforts to avoid weight gain, e.g., fasting, self-induced vomiting, laxative or diuretic abuse. Exemplary eating disorders include anorexia nervosa and bulimia.

As used herein, the term "obesity" refers to the excessive accumulation of body fat. Obesity may have genetic, environmental (e.g., expending less energy than is consumed) and regulatory determinants. Obesity includes exogenous, hyperinsulinar, hyperplasmic, hypothyroid, hypothalamic, symptomatic, infantile, upper body, alimentary, hypogonadal, simple and central obesity, hypophyseal adiposity and hyperphagia. Cardiovascular disorders, such as hypertension and coronary artery disease, and metabolic disorders, such as hyperlidemia and diabetes, are commonly associated with obesity.

As used herein, the term "PPARδ-responsive condition or disorder" refers to a condition or disorder that responds favorably to modulation of PPARδ activity. Favorable responses to PPARδ modulation include alleviation or abrogation of the disease and/or its attendant symptoms, inhibition of the disease, i.e., arrest or reduction of the development of the disease, or its clinical symptoms, and regression of the disease or its clinical symptoms. A PPARδ-responsive condition or disease may be completely or partially responsive to PPARδ-modulation. A PPARδ-responsive condition or disorder may be associated with inappropriate, e.g., less than or greater than normal, PPARδ-activity. Inappropriate PPARδ functional activity might arise as the result of PPARδ expression in cells which normally do not express PPARδ, decreased PPARδ expression (leading to, e.g., lipid and metabolic disorders and diseases) or increased PPARδ expression. A PPARδ-responsive condition or disease may include a PPARδ-mediated condition or disease.

As used herein, the term "PPARδ-mediated condition or disorder" and related terms and phrases refer to a condition or disorder characterized by inappropriate, e.g., less than or greater than normal, PPARδ activity. Inappropriate PPARδ functional activity might arise as the result of PPARδ expression in cells which normally do not express PPARδ, decreased PPARδ expression (leading to, e.g., metabolic and inflammatory disorders and diseases) or increased PPARδ expression. A PPARδ-mediated condition or disease may be completely or partially mediated by inappropriate PPARδ functional activity. However, a PPARδ-mediated condition or disease is one in which modulation of PPARδ results in some effect on the underlying condition or disorder (e.g., a PPARδ agonist results in some improvement in patient well-being in at least some patients).

As used herein, the terms "iNOS-responsive condition or disorder", "TNF-responsive condition or disorder" and related terms and phrases refer to a condition or disorder that responds favorably to modulation of iNOS or TNF activity, respectively. Favorable responses to iNOS or TNF modulation include alleviation or abrogation of the disease and/or its attendant symptoms, inhibition of the disease, i.e., arrest or reduction of the development of the disease, or its clinical symptoms, and regression of the disease or its clinical symptoms. An iNOS- or TNF-responsive condition or disease may be completely or partially responsive to iNOS or TNF modulation. An iNOS or TNF-responsive condition or disorder may be associated with inappropriate, e.g., less than or greater than normal, iNOS or TNF activity. Inappropriate iNOS or TNF functional activity might arise as the result of overproduction of nitric oxide (NO), iNOS or TNF expression in cells which normally do not express iNOS or TNF, decreased iNOS or TNF expression (leading to, e.g., lipid and metabolic disorders and diseases) or increased iNOS or TNF expression. An iNOS- or TNF-responsive condition or disease may include an iNOS- or TNF-mediated condition or disease.

As used herein, the terms "iNOS-mediated condition or disorder", "TNF-mediated condition or disorder" and related terms and phrases refer to a condition or disorder characterized by inappropriate, e.g., less than or greater than normal, iNOS or TNF activity, respectively. Inappropriate iNOS or TNF functional activity might arise as the result of overproduction of NO by iNOS, iNOS or TNF expression in cells which normally do not express iNOS or TNF, decreased iNOS or TNF expression, increased iNOS or TNF expression. An iNOS- or TNF-mediated condition or disease may be completely or partially mediated by inappropriate iNOS or TNF functional activity. However, an iNOS- or TNF-mediated condition or disease is one in which modulation of iNOS or TNF results in some effect on the underlying condition or disorder (e.g., an iNOS or TNF inhibitor results in some improvement in patient well-being in at least some patients).

The term "alkyl," by itself or as part of another substituent, means, unless otherwise stated, a straight or branched chain, or cyclic hydrocarbon radical, or combination thereof, which may be fully saturated, mono- or poly-unsaturated and can include di- and multi-valent radicals, having the number of carbon atoms designated (i.e. $C_1$–$C_{10}$ means one to ten carbons). Examples of saturated hydrocarbon radicals include groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below as "heteroalkyl," "cycloalkyl" and "alkylene." The term "alkylene" by itself or as part of another substituent means a divalent radical derived from an alkane, as exemplified by —$CH_2CH_2CH_2CH_2$—. Typically, an alkyl group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. Also included in the term "heteroalkyl" are those radicals described in more detail below as "heteroalkylene" and "heterocycloalkyl." The term "heteroalkylene" by itself or as part of another substituent means a divalent radical derived from heteroalkyl, as exemplified by —$CH_2$—$CH_2$—S—$CH_2CH_2$— and —$CH_2$—S—$CH_2$—$CH_2$—NH—$CH_2$—. For heteroalkylene groups, heteroatoms can also occupy either or both of the chain termini. Still further, for alkylene and heteroalkylene linking groups, no orientation of the linking group is implied.

The terms "cycloalkyl" and "heterocycloalkyl", by themselves or in combination with other terms, represent, unless otherwise stated, cyclic versions of "alkyl" and "heteroalkyl", respectively. Thus, the terms "cycloalkyl" and "heterocycloalkyl" are meant to be included in the terms "alkyl" and "heteroalkyl", respectively. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl", are meant to include alkyl substituted with halogen atoms which can be the same or different, in a number ranging from one to (2m'+1), where m' is the total number of carbon atoms in the alkyl group. For example, the term "halo($C_1$–$C_4$)alkyl" is meant to include trifluoromethyl, 2,2,2-trifluoroethyl, 4-chlorobutyl, 3-bromopropyl, and the like. Thus, the term "haloalkyl" includes monohaloalkyl (alkyl substituted with one halogen atom) and polyhaloalkyl (alkyl substituted with halogen atoms in a number ranging from two to (2m'+1) halogen atoms, where m' is the total number of carbon atoms in the alkyl group). The term "perhaloalkyl" means, unless otherwise stated, alkyl substituted with (2m'+1) halogen atoms, where m' is the total number of carbon atoms in the alkyl group. For example, the term "perhalo($C_1$–$C_4$)alkyl", is meant to include trifluoromethyl, pentachloroethyl, 1,1,1-trifluoro-2-bromo-2-chloroethyl, and the like.

The term "aryl," employed alone or in combination with other terms (e.g., aryloxy, arylthioxy, arylalkyl) means, unless otherwise stated, an aromatic substituent which can be a single ring or multiple rings (up to three rings) which are fused together or linked covalently. The rings may each contain from zero to four heteroatoms selected from N, O, and S, wherein the nitrogen and sulfur atoms are optionally oxidized, and the nitrogen atom(s) are optionally quaternized. The aryl groups that contain heteroatoms may be referred to as "heteroaryl" and can be attached to the remainder of the molecule through a heteroatom Non-limiting examples of aryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl ring systems are selected from the group of acceptable substituents described below.

The term "arylalkyl" is meant to include those radicals in which an aryl group is attached to an alkyl group (e.g., benzyl, phenethyl, pyridylmethyl and the like) or a heteroalkyl group (e.g., phenoxymethyl, 2-pyridyloxymethyl, 3-(1-naphthyloxy)propyl, and the like).

Each of the above terms (e.g., "alkyl," "heteroalkyl" and "aryl") is meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be a variety of groups selected from: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —CN and —NO$_2$ in a number ranging from zero to (2N+1), where N is the total number of carbon atoms in such radical. R', R" and R'" each independently refer to hydrogen, unsubstituted ($C_1$–$C_8$)alkyl and heteroalkyl, unsubstituted aryl, aryl substituted with 1–3 halogens, unsubstituted alkyl, alkoxy or thioalkoxy groups, or aryl-($C_1$–$C_4$)alkyl groups. When R' and R" are attached to the same nitrogen atom, they can be combined with the carbon atoms to which they are attached with the nitrogen atom to form a 5-, 6- or 7-membered ring containing from 1 to 3 heteroatoms selected from the group consisting of N, O and S. For example, —NR'R" is meant to include 1-pyrrolidinyl and 4-morpholinyl. From the above discussion of substituents, one of skill in the art will understand that the term "alkyl" is meant to include groups such as haloalkyl (e.g., —$CF_3$ and —$CH_2CF_3$) and acyl (e.g., —C(O)$CH_3$, —C(O)$CF_3$, —C(O)$CH_2$O$CH_3$, and the like).

Similarly, substituents for the aryl groups are varied and are selected from: -halogen, —OR', —OC(O)R', —NR'R", —SR', —R', —CN, —$NO_2$, —$CO_2$R', —CONR'R", —C(O)R', —OC(O)NR'R", —NR"C(O)R', —NR"C(O)$_2$R', —NR'—C(O)NR"R'", —NH—C($NH_2$)=NH, —NR'C($NH_2$)=NH, —NH—C($NH_2$)=NR', —S(O)R', —S(O)$_2$R', —S(O)$_2$NR'R", —$N_3$, —CH(Ph)$_2$, fluoro($C_1$–$C_4$)alkoxy, and fluoro($C_1$–$C_4$)alkyl, in a number ranging from zero to the total number of open valences on the aromatic ring system; and where each R', R" and R'" is independently selected from hydrogen, ($C_1$–$C_8$)alkyl and heteroalkyl, unsubstituted aryl, (unsubstituted aryl)-($C_1$–$C_4$)alkyl and (unsubstituted aryl)oxy-($C_1$–$C_4$)alkyl.

Two of the substituents on adjacent atoms of the aryl ring may optionally be replaced with a substituent of the formula —T—C(O)—($CH_2$)$_q$—U—, wherein T and U are independently —NH—, —O—, —$CH_2$— or a single bond, and q is an integer of from 0 to 2. Alternatively, two of the substituents on adjacent atoms of the aryl ring may optionally be replaced with a substituent of the formula —A—($CH_2$)$_r$—B—, wherein A and B are independently —$CH_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl ring may optionally be replaced with a substituent of the formula —($CH_2$)$_s$—X—($CH_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen and unsubstituted ($C_1$–$C_6$)alkyl.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, oxalic, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al. (1977) *J. Pharm. Sci.* 66:1–19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent. In the present invention, hydrolizable esters are particularly preferred prodrugs.

Compounds containing bioisosteric replacements for the $CO_2$H attached to $CR^aR^b$, such as those reviewed in Patani et al. (1996) *Chem. Rev.* 96(8):3147–3176, are contemplated by the present invention and are intended to be within the scope of the present invention.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, enantiomers, diastereomers, geometric isomers and individual isomers are all intended to be encompassed within the scope of the present invention. These isomers can be resolved or asymmetrically synthesized using conventional methods to render the isomers "optically pure" i.e., substantially free of its other isomers; preferably, 85%, 90%, 95% or 97% ee.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). Radiolabeled compounds are useful as therapeutic agents, e.g., cancer therapeutic agents, research reagents, e.g., assay reagents, and diagnostic agents, e.g., in vivo imaging agents. All isotopic variations of the compounds of the present invention, whether radioactive or not, are intended to be encompassed within the scope of the present invention.

Embodiments of the Invention

A class of compounds that interact with PPARδ has been discovered. Depending on the biological environment (e.g., cell type, pathological condition of the host, etc.), these compounds can activate or block the actions of PPARδ. By activating the PPARδ receptor, the compounds will find use as therapeutic agents capable of modulating conditions and disorders mediated by PPARδ or responsive to PPARδ modulation. As noted above, examples of such diseases and disorders include metabolic disorders, cardiovascular diseases, inflammatory conditions and neoplastic diseases. Additionally, the compounds are useful for the treatment of complications of these diseases and disorders (e.g., neuropathy, retinopathy and glomerulosclerosis). While the compounds of the present invention are believed to exert their effect through modulation of PPARδ, the mechanism of action by which the compounds act is not a limitation of all embodiments of the present invention. For example, the compounds of the invention may interact with other PPAR receptor isotypes, e.g., PPARα.

Compounds

In one aspect, the present invention provides compounds having the formula (Ia):

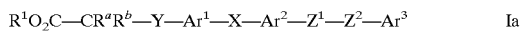

or a pharmaceutically acceptable salt or prodrug thereof, wherein X is O, $S(O)_m$, CR'R" or $SO_2NR$". Y is O or CR'R".

$Z^1$ and $Z^2$ are independently O, $S(O)_m$, $(CR'R")_n$, $N(R")$, $C(O)NR"$ or $CR'R"C(O)NR'"$ or $Z^1$ and $Z^2$ may be combined with the carbon atoms to which they are attached to form ($C_2$–$C_4$)alkenyl (e.g., —CH=CH ). It is to be understood that $Z^1$ and $Z^2$ are combined to form a stable moiety —$Z^1$—$Z^2$ . For example, compounds wherein —$Z^1$—$Z^2$— is —O—O— (peroxides) and the like are not intended to be within the scope of the invention.

$Ar^1$ and $Ar^2$ are independently an aromatic group. Preferably, $Ar^1$ and $Ar^2$ are independently benzene, naphthalene, pyrrole, imidazole, pyrazine, oxazole, thiazole, furan, thiophene, pyridine, pyrimidine, benzothiazole, benzimidazole, indole, isoquinoline or quinoline.

$Ar^3$ is aryl. Preferably, $Ar^3$ is phenyl, naphthyl, pyrrolyl, imidazolyl, pyrazinyl, oxazolyl, thiazolyl, furyl, thienyl, pyridinyl, pyrimidinyl, benzothiazolyl, benzimidazolyl, indolyl, isoquinolyl or quinolyl. Examples of $Ar^3$ include, but are not limited to, phenyl, 2-trifluoromethylphenyl, 3-trifluoromethylphenyl, 4-trifluoromethylphenyl, 4-oxazolyl, 5-thiazolyl, 2-pyridyl, 3-pyridyl, 4-pyridyl, 2-benzimidazolyl, 4-quinolyl, 5-quinolyl and 6-quinolyl.

$R^1$ is hydrogen, ($C_1$–$C_8$)alkyl or aryl($C_1$–$C_4$)alkyl.

$R^a$ and $R^b$ are independently selected from the group consisting of hydrogen, ($C_1$–$C_4$)alkyl, aryl and aryl($C_1$–$C_4$)alkyl.

Each R', R" and R'" is independently hydrogen, ($C_1$–$C_4$) alkyl, aryl or aryl($C_1$–$C_4$)alkyl. The subscript m is an integer from 0 to 2 and the subscript n is an integer from 1 to 2, with the proviso that said compound is not 3-amino-4-[4-(phenylmethoxy)phenoxy]phenoxyacetic acid, 4-[3,5-diiodo-4-(phenylmethoxy)phenoxy]-3,5-diiodobenzene-propanoic acid or 4-[4-(benzyloxy)-3-iodophenoxy]-3,5-diiodohydrocinnamic acid.

In preferred embodiments, $Ar^1$ and $Ar^2$ are both benzene. In particularly preferred embodiments, $Ar^1$ and $Ar^2$ are independently benzene-1,4-diyl which is unsubstituted or substituted with 1 or 2 substituents selected independently from the group consisting of halogen, ($C_1$–$C_4$)alkyl, ($C_5$–$C_6$)cycloalkyl, fluoro($C_1$–$C_4$)alkyl, OR', aryl, aryl ($C_1$–$C_4$)alkyl, $NO_2$, NR'R", C(O)R', $CO_2R'$, C(O)NR'R", N(R")C(O)R', N(R")$CO_2R'$, N(R")C(O)NR'R", $S(O)_m$NR'R", $S(O)_mR'$, CN and N(R")$S(O)_mR'$, or with two adjacent substituents which, together with the carbon atoms to which they are attacted, form a fused aromatic or cycloalkane ring.

One group of preferred embodiments is represented by the formula (Ib):

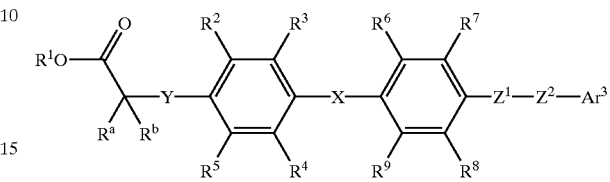

wherein $R^2$, $R^3$, $R^4$, $R^5$, $R^6$, $R^7$, $R^8$ and $R^9$ are independently selected from hydrogen, halogen, ($C_1$–$C_4$)alkyl, ($C_5$–$C_6$) cycloalkyl, fluoro($C_1$–$C_4$)alkyl, OR', aryl, aryl($C_1$–$C_4$)alkyl, $NO_2$, NR'R", C(O)R', $CO_2R'$, C(O)NR'R", N(R")C(O)R', N(R")$CO_2R'$, N(R")C(O)NR'R", $S(O)_m$NR'R", $S(O)_mR'$, CN and N(R")$S(O)_mR'$, or any two adjacent R groups selected from $R^2$, $R^3$, $R^4$, $R^5$, $R^6$, $R^7$, $R^8$ and $R^9$ (e.g., $R^2$ and $R^3$, $R^4$ and $R^5$, $R^6$ and $R^7$ or $R^8$ and $R^9$) may be combined with the carbon atoms to which they are attached to form a fused aromatic or cycloalkane ring.

Another group of preferred embodiments is represented by formula Ib, with the proviso that when X is O, $Z^1$ is O, $Z^2$ is $CH_2$ and $Ar^3$ is unsubstituted phenyl, Y is other than O or $CH_2$.

Another group of preferred embodiments is represented by formula Ib, wherein X is $S(O)_m$, CR'R" or $SO_2NR$".

Within each of these groups of preferred embodiments are several further preferred groups, described below.

X is preferably $S(O)_m$, CR'R" or $SO_2NR$". When X is CR'R", then R' and R" are preferably both hydrogen or ($C_1$–$C_4$)alkyl. Exemplary values for CR'R" include $CH_2$ and $C(CH_3)_2$. More preferably, X is $S(O)_m$. Most preferably, X is S.

Y is preferably O or CR'R". When Y is CR'R", then R' and R" are preferably both hydrogen or ($C_1$–$C_4$)alkyl. Exemplary values for CR'R" include $CH_2$ and $C(CH_3)_2$. More preferably, Y is O.

$Ar^3$ is preferably phenyl or pyridyl. More preferably, $Ar^3$ is substituted phenyl. Most preferably, $Ar^3$ is phenyl substituted with at least one fluoro($C_1$–$C_4$)alkyl.

$R^1$ is preferably hydrogen or ($C_1$–$C_4$)alkyl. More preferably, $R^1$ is hydrogen.

$R^a$ and $R^b$ are preferably both hydrogen or ($C_1$–$C_4$)alkyl. More preferably, $R^a$ and $R^b$ are both hydrogen or methyl. Most preferably, $R^a$ and $R^b$ are both hydrogen.

Preferably, $Z^1$ and $Z^2$ are independently O, $(CR'R")_n$, N(R") or CR'R"C(O)NR'". More preferably, $Z^1$ and $Z^2$ are independently O, $(CR'R")_n$ or N(R")". In particularly preferred embodiments, $Z^1$ is O and $Z^2$ is $(CR'R")_n$. Exemplary values for $Z^1$—$Z^2$- include —O—$CH_2$— and —O—($CH_2)_2$—. In separate, but particularly preferred embodiments, $Z^1$ is $(CR'R")_n$ and $Z^2$ is O. Exemplary values for —$Z^1$—$Z^2$— include —$CH_2$—O— and —($CH_2)_2$—O—. In other separate, but particularly preferred embodiments, $Z^1$ is $(CR'R")_n$ and $Z^2$ is N(R"). Exemplary values for —$Z^1$—$Z^2$—include —$CH_2$—NH—, —$CH_2$—$N(CH_3)$—, —($CH_2)_2$—NH—, —($CH_2)_2$—$N(CH_3)$— and —($CH_2)_2$—N ($CH_2CH_3$)—. In still other separate, but particularly preferred embodiments, $Z^1$ is N(R") and $Z^2$ is $(CR'R")_n$. Exemplary values for —$Z^1$—$Z^2$— include —NH—$CH_2$—, —N(CH$_3$)—CH$_2$—, —NH—(CH$_2$)$_2$— and —N(CH$_3$)—(CH$_2$)$_2$—. In other separate, but particularly preferred embodiments, Z$^1$ is O and Z$^2$ is CR'R"C(O)NR'". Exemplary values for —Z$^1$—Z$^2$— include —O—CH$_2$C(O)NH—, —O—CH$_2$C(O)N(CH$_3$)—, —CH$_2$C(O)N(CH$_2$CH$_3$)— and —O—CH$_2$C(O)N(CH$_2$C$_6$H$_5$)—.

Also particularly preferred are those embodiments that combine each of these preferred groups. Accordingly, one group of particularly preferred embodiments is represented by the formula (II):

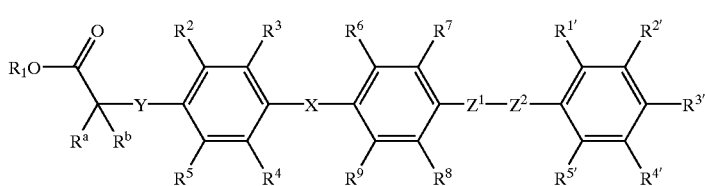

wherein R$^{1'}$, R$^{2'}$, R$^{3'}$, R$^{4'}$ and R$^{5'}$ are independently selected from hydrogen, halogen, (C$_1$–C$_4$)alkyl, fluoro(C$_1$–C$_4$)alkyl, OR', aryl, aryl(C$_1$–C$_4$)alkyl, NO$_2$, NR'R", C(O)R', CO$_2$R', C(O)NR'R", N(R")C(O)R', N(R")CO$_2$R', N(R")C(O)NR'R", S(O)$_m$NR'R", S(O)$_m$R', CN and N(R")S(O)$_m$R'. X, Y, Z$^1$, Z$^2$, R$^a$, R$^b$, R$^1$, R$^2$, R$^3$, R$^4$, R$^5$, R$^6$, R$^7$, R$^8$, R$^9$, R', R" and R'" have the meanings and preferred groupings provided above. Preferably, at least one of R$^{1'}$, R$^{2'}$, R$^{3'}$, R$^{4'}$ and R$^{5'}$ is not hydrogen. More preferably, at least one of R$^{1'}$, R$^{2'}$, R$^{3'}$, R$^{4'}$ and R$^{5'}$ is fluoro(C$_1$–C$_4$)alkyl. Still more preferably, R$^{3'}$ is CF$_3$, R$^{4'}$ is CF$_3$ or R$^{5'}$ is CF$_3$.

Another group of particularly preferred embodiments is represented by the formula (IV):

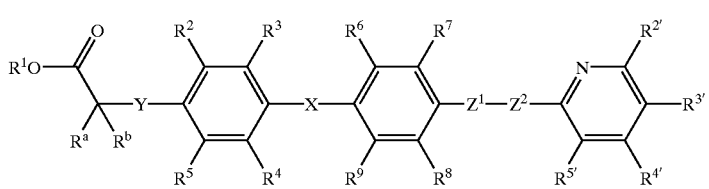

wherein R$^{2'}$, R$^{3'}$, R$^{4'}$ and R$^{5'}$ are independently selected from hydrogen, halogen, (C$_1$–C$_4$)alkyl, fluoro(C$_1$–C$_4$)alkyl, OR', aryl, aryl(C$_1$–C$_4$)alkyl, NO$_2$, NR'R", C(O)R', CO$_2$R', C(O)NR'R", N(R")C(O)R', N(R")CO$_2$R', N(R")C(O)NR'R", S(O)$_m$NR'R", S(O)$_m$R', CN and N(R")S(O)$_m$R'. X, Y, Z$^1$, Z$^2$, R$^1$, R$^2$, R$^3$, R$^4$, R$^5$, R$^6$, R$^7$, R$^8$, R$^9$, R$^a$, R$^b$, R', R" and R'" have the meanings and preferred groupings provided above.

In another group of particularly preferred embodiments X is S and Y is O. Within this group, preferred compounds are represented by the formula (V):

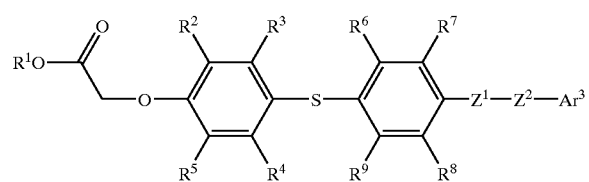

wherein Ar$^3$, R$^1$, R$^2$, R$^3$, R$^4$, R$^5$, R$^6$, R$^7$, R$^8$, R$^9$, R', R" and R'" have the meanings and preferred groupings provided above.

Another group of particularly preferred embodiments is represented by formula V, wherein Ar$^3$ is phenyl substituted with at least one fluoro(C$_1$–C$_4$)alkyl.

Another group of particularly preferred embodiments is represented by the formula (VII):

wherein X, Y, Ar$^3$, R$^a$, R$^b$, R$^1$, R$^2$, R$^3$, R$^4$, R$^5$, R$^6$, R$^7$, R$^8$, R$^9$, R', R" and R'" have the meanings and preferred groupings provided above.

Another group of particularly preferred embodiments is represented by the formula (VIII):

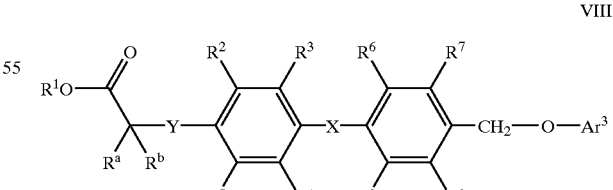

wherein X, Y, Ar$^3$, R$^a$, R$^b$, R$^1$, R$^2$, R$^3$, R$^4$, R$^5$, R$^6$, R$^7$, R$^8$, R$^9$, R', R" and R'" have the meanings and preferred groupings provided above.

Still another group of particularly preferred embodiment is represented by the formula (IX):

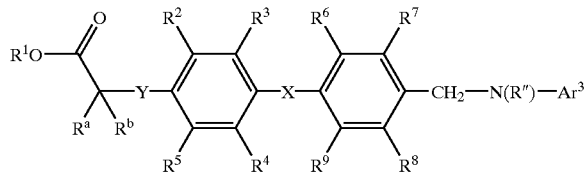

wherein X, Y, Ar³, R$^a$, R$^b$, R¹, R², R³, R⁴, R⁵, R⁶, R⁷, R⁸, R⁹, R', R" and R'" have the meanings and preferred groupings provided above.

Another group of particularly preferred embodiments is represented by the formula (X):

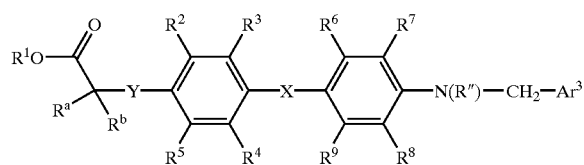

wherein X, Y, Ar³, R$^a$, R$^b$, R¹, R², R³, R⁴, R⁵, R⁶, R⁷, R⁸, R⁹, R', R" and R'" have the meanings and preferred groupings provided above.

Another group of particularly preferred embodiments is represented by the formula (XI):

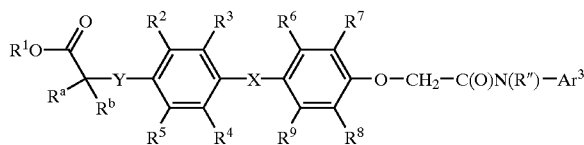

wherein X, Y, Ar³, R$^a$, R$^b$, R¹, R², R³, R⁴, R⁵, R⁶, R⁷, R⁸, R⁹, R', R" and R'" have the meanings and preferred groupings provided above.

Figure 1B:
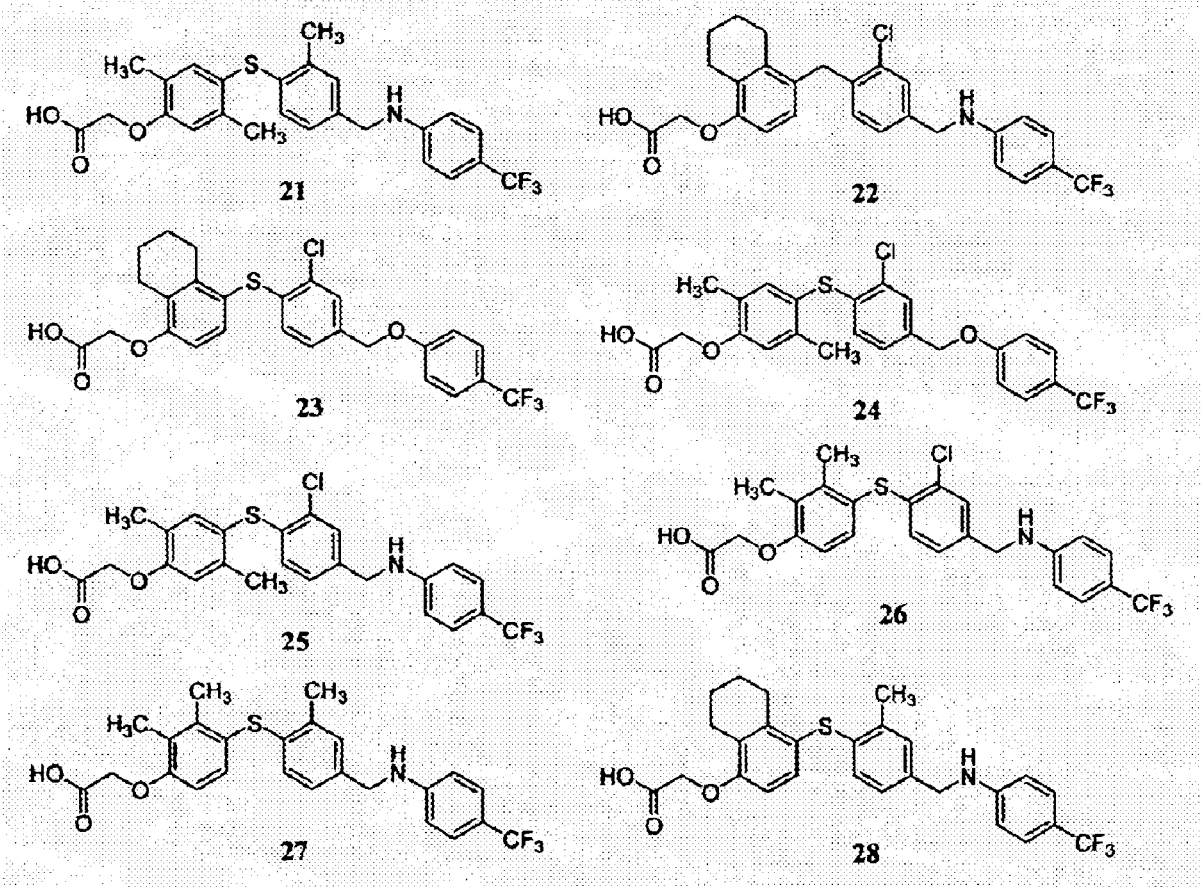

Exemplary preferred compounds are provided in FIG. 1.

In sum, the invention encompasses novel compounds, novel pharmaceutical compositions and/or novel methods of use. While some compounds disclosed herein are available from commercial sources, the pharmaceutical compositions or methods of using these compounds are novel. Unless otherwise indicated, it is to be understood that the invention includes those compounds that are novel, as well as pharmaceutical compositions, various methods (e.g., methods of treating certain PPARδ-mediated conditions and diseases), and the like which include both the novel compounds of the invention and compounds that are commercially available. Exemplary commercially available compounds include:

3-amino-4-[4-(phenylmethoxy)phenoxy]phenoxyacetic acid,
4-[3,5-diiodo-4-(phenylmethoxy)phenoxy]-3,5-diiodobenzenepropanoic acid, and
4-[4-(benzyloxy)-3-iodophenoxy]-3,5-diiodohydrocinnamic acid.

Preparation of the Compounds

Schemes 1–13 below provide exemplary synthetic methods for the preparation of the compounds of the present invention. One of skill in the art will understand that additional methods are also useful. In other words, the compounds of the invention can be made using conventional organic synthesis using starting materials, reagents and reactions well known in the art.

The terms "head group" and "tail group", as used herein, refer to the indicated regions of compounds of formulas Ia and Ib:

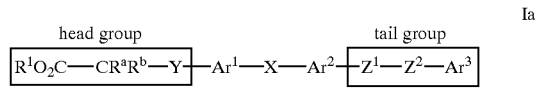

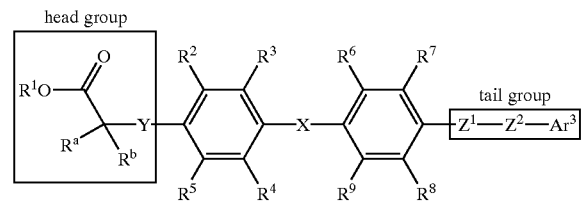

Certain compounds of the invention may be conveniently prepared by a general process, outlined in Scheme 1, wherein a bis-phenol A is successively alkylated with an α-halo ester B in the presence of a non-nucleophilic base, such as K₂CO₃, Cs₂CO₃, NaH or Et₃N or other amine base, and with an aryl(C₁–C₄)alkyl halide D. Alternatively, alkylation can be accomplished via Mitsunobu reaction of the corresponding alcohols in place of halides B and D. The esters E can be easily saponified to the carboxylic acid, if desired.

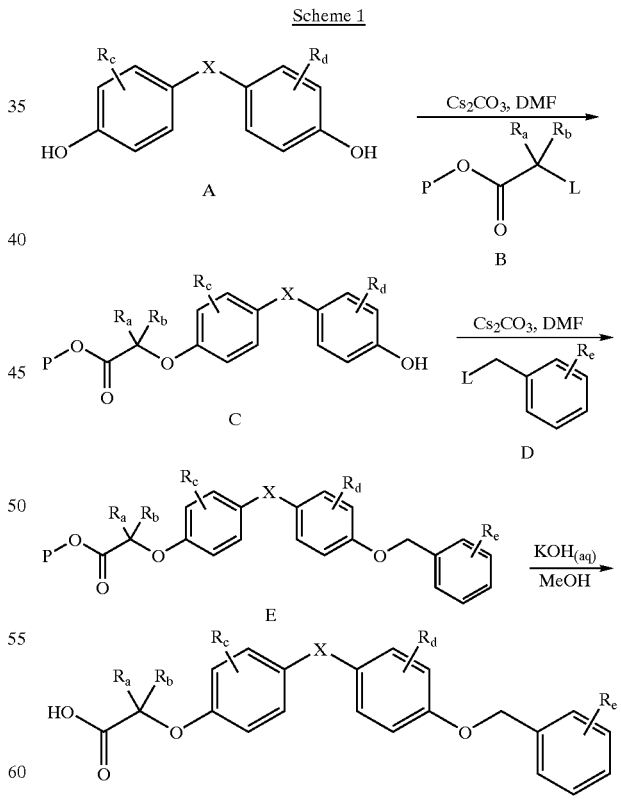

A variant of the above scheme is useful for generation of a library of compounds of the invention. Phenol C, wherein R$^c$ is tert-butyl, can be generated as in Scheme 1. The second alkylation can be carried out using polymer supported TBD (1,5,7-triazabicyclo[4.4.0]dec-5-ene) as the base. The tert-butyl ester can be cleaved by treatment with TFA and excess reagents can be removed by treatment with N-(2-mercaptoethyl)aminomethyl polystyrene and MP-carbonate resins. Advantages of this variation for library synthesis include the easy removal of byproducts by filtration or evaporation under reduced pressure.

Scheme 2

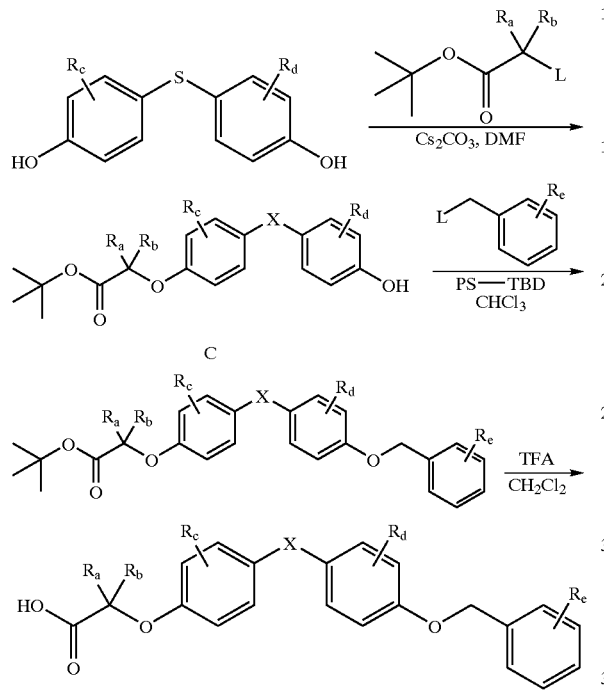

A number of symmetrical bis-phenols of formula A, i.e., bis-phenols wherein $R^c$ and $R^d$ are the same, are commercially available. For unsymmetrical bis-phenols, i.e., bis-phenols wherein $R^c$ and $R^d$ are different, compounds of the invention can be prepared according to Scheme 3 below. An aryloxyacetic acid head group can be generated by alkylation of a suitably substituted aryl alcohol F. Chlorosulfonation followed by reduction of the sulfonyl chloride moiety generates thiophenol H. Thiophenols of formula H are useful for generating a variety of compounds of the invention.

Scheme 3

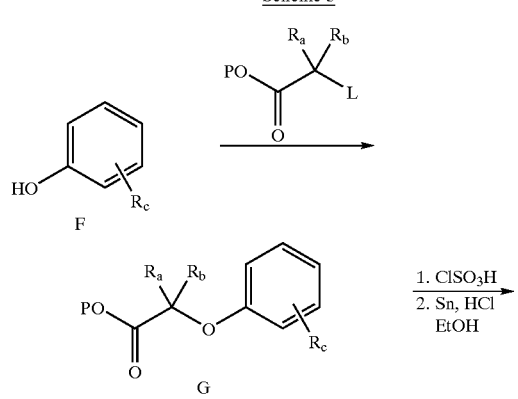

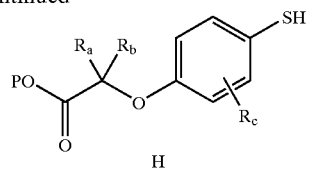

The tail group can also be derived from alkylation of a suitably substituted aryl alcohol I (see Scheme 4). The resulting ether J can be directly coupled to the thiol generated using [bis(trifluoroacetoxy)iodo]benzene in hexafluoroisopropanol (Kita et al. (1995) *J. Org Chem.* 60:7144–7148). If $R^a$ is a suitable halogen (e.g., Br, I), diaryl sulfides K can be prepared by a copper-catalyzed Ullmann-type process (Palomo et al. (2000) *Tetrahedron Lett.* 41:1283–1286). The skilled practitioner will recognize that a variety of palladium, nickel or copper catalyzed couplings are useful for preparing linked biaryl intermediates such as K (Scheme 4) or A (Scheme 1); see, Hartwig (1998) *Acc. Chem. Res.* 31:852–860 and references therein. After coupling, the ester K can be saponified to the carboxylic acid L.

Scheme 4

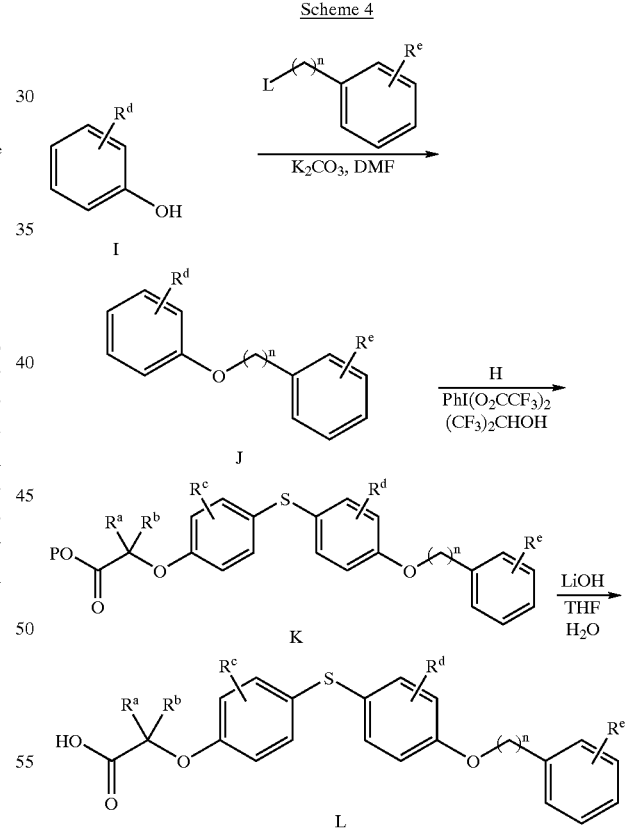

Compounds of the invention not accessed through bis-phenol intermediates such as A can be assembled by nucleophilic aromatic substitution employing sulfide H. Reaction of H (see Scheme 5) with a suitably substituted aromatic aldehyde (M) under basic conditions in a dipolar, aprotic solvent leads to the diaryl sulfide N. The aldehyde can be reduced and the tail group attached by a Mitsunobu reaction (Mitsunobu (1981) *Synthesis* 1–28).

Scheme 5

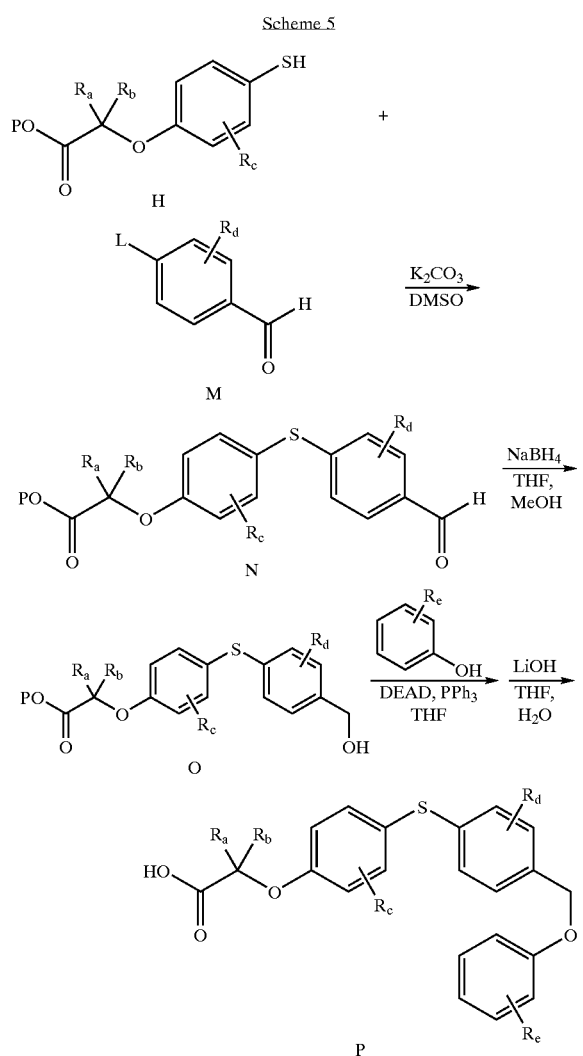

Alternatively, aldehyde N can be reduced and the tail group attached by an alkylation reaction.

Scheme 6 exemplifies the preparation of compounds which incorporate alkylene in the head group from aldehyde R via reaction with diethylphosphonoacetic acid ester and subsequent reduction by Mg.

Scheme 6

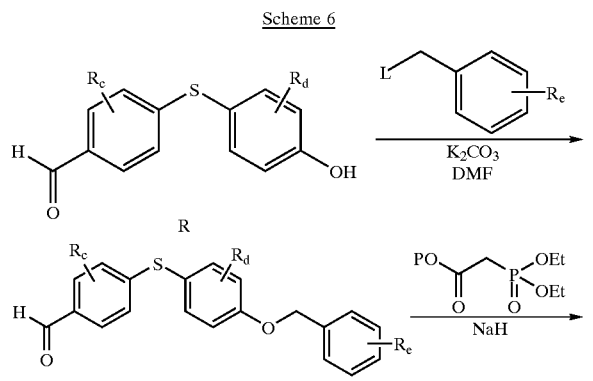

Scheme 7 exemplifies the preparation of compounds which incorporate alkylene in the tail group from aldehyde N via reaction with diethyl benzylphosphonate.

Scheme 7

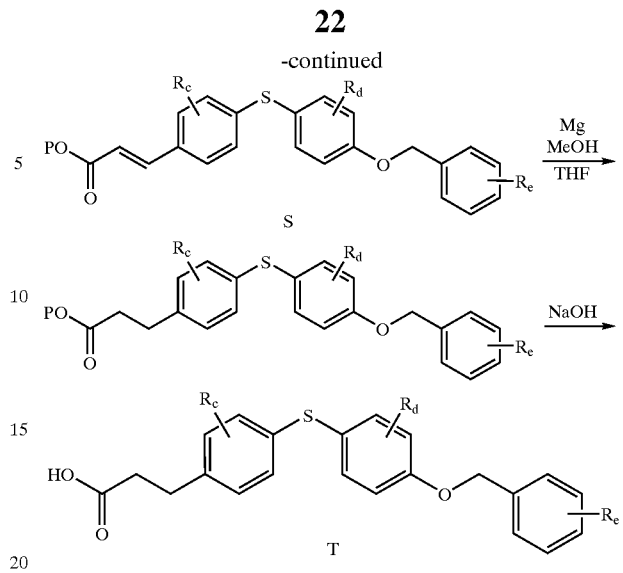

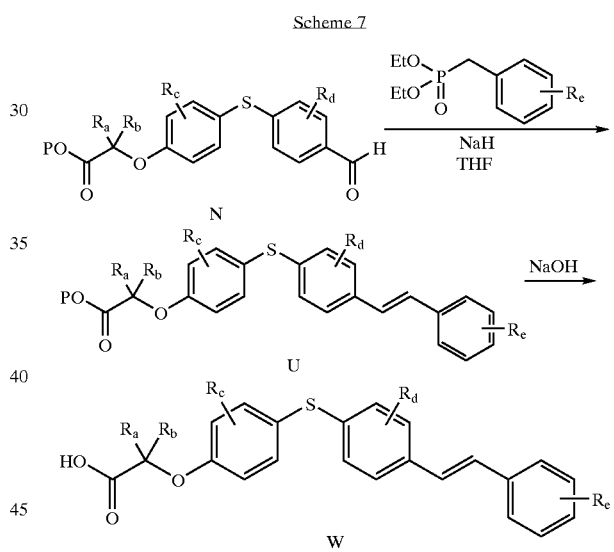

Compounds of the invention containing a sulfonamide linkage can be prepared as shown in Scheme 8. Alkylation of a nitro-substituted aryl alcohol followed by reduction of the nitro group provides the arylamino compound X. Reaction of X with sulfonyl chloride Y (obtained by chlorosulfonation of the aryloxyacetic acid derivative G as described above) affords the sulfonamide Z. The carboxylic ester can then be saponified if desired.

Scheme 8

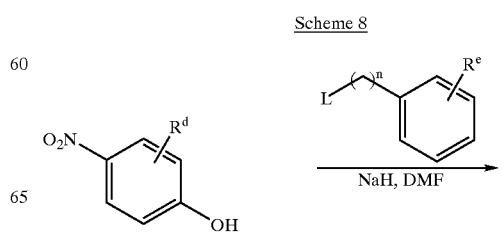

-continued

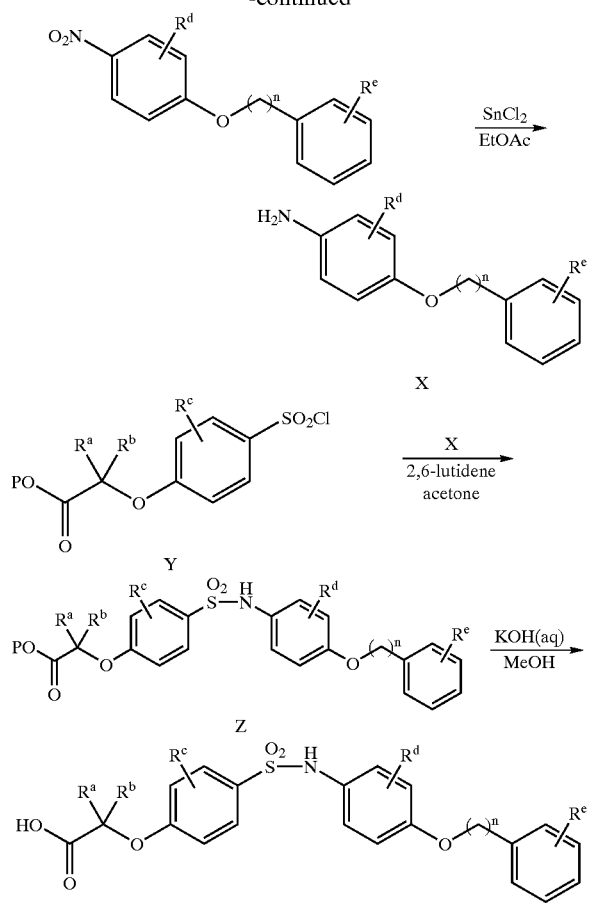

X

If further substitution of the sulfonamide nitrogen is desired, alkylation of intermediate Z can be accomplished as illustrated in Scheme 9. After alkylation, the carboxylic ester can be saponified if desired.

Scheme 9

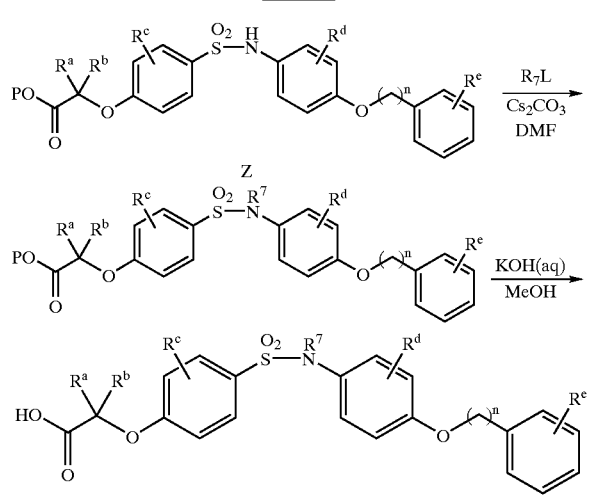

Sulfonyl chlorides Y are also useful for reaction with other classes of amines besides anilines. To illustrate, the preparation of a library of N-aryl piperazines is shown in Scheme 10. Reaction of sulfonyl chlorides Y with N-aryl piperazines AA is promoted with polymer-supported Hünig's base. After removal of the polymer-supported reagent, the ester can be cleaved if desired.

Scheme 10

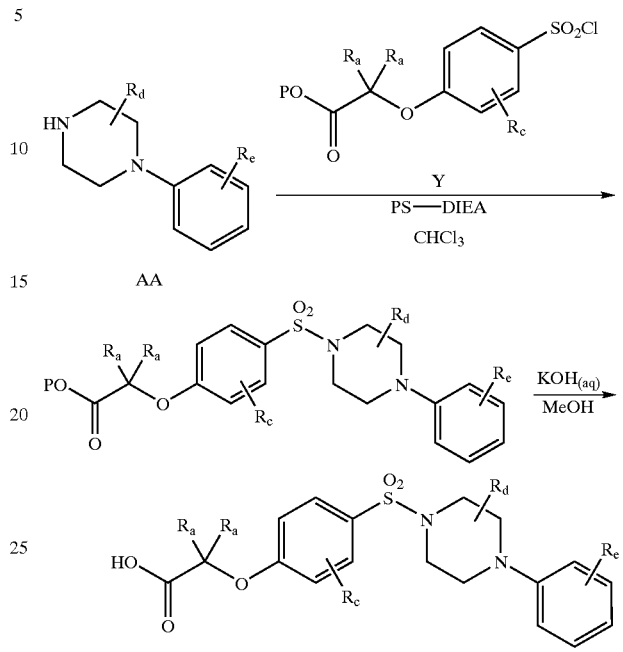

Compounds of the invention which incorporate a carboxamide can be accessed from intermediate A, as outlined in Scheme 11. Exhaustive alkylation of A with an α-halo ester followed by saponification generates the diacid BB. The diacid is then coupled to an appropriate amine.

Scheme 11

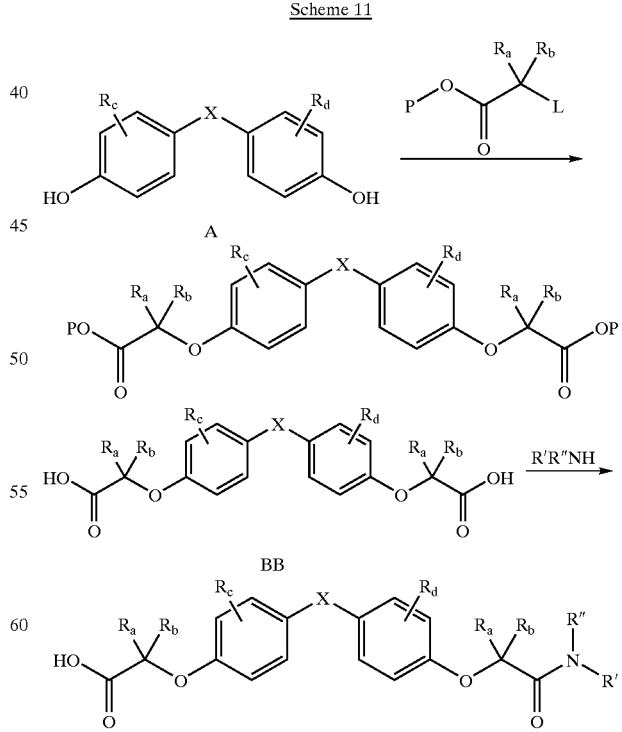

Alternatively, the diacid BB can be loaded on to a solid support, and the remaining free acid coupled with a series of amines. Cleavage of the compound from the solid support provides the desired acid products CC. This method is suited to the rapid generation of a library of analogs (Scheme 12).

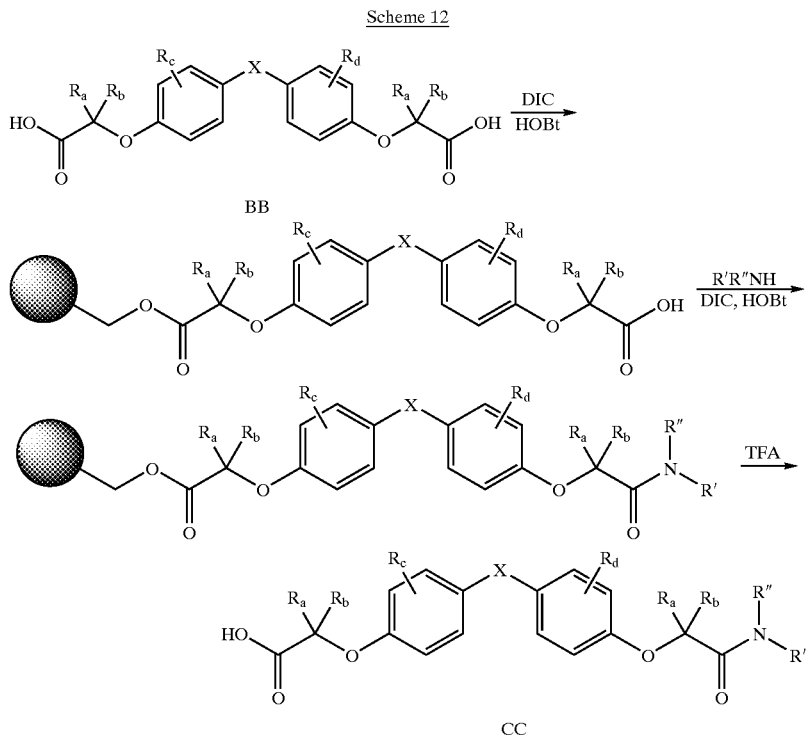

Scheme 13 exemplifies the preparation of compounds which contain aminomethyl linkage in the tail group. Reductive amination of aldehyde N (see Scheme 5) with a substituted aniline followed by ester hydrolysis generates these types of compound.

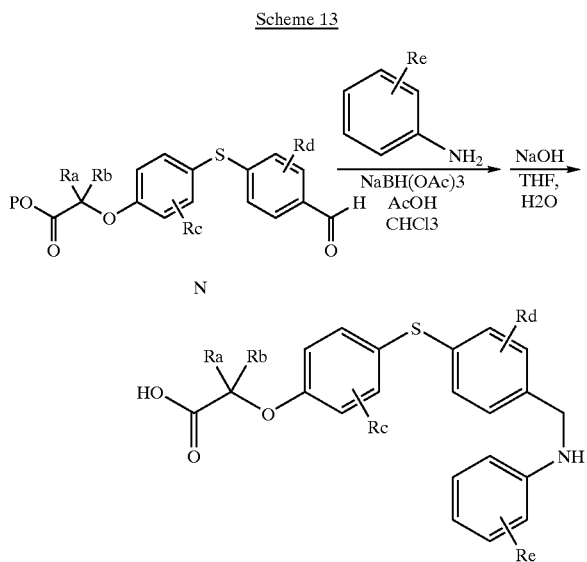

Regarding the molecular structures set forth in Schemes 1–13 above, one of skill in the art will readily appreciate that precursors and intermediates having aryl groups other than phenyl, e.g. naphthyl, can be used to practice the synthetic method. Moreover, it will be appreciated that the groups $R^c$, $R^d$ and $R^e$ indicate, in a very general sense, substituents on the aryl and/or piperazinyl groups. $R^c$, $R^d$ and $R^e$ can be the same or different. $R^c$, $R^d$ and $R^e$ can represent a single substituent or multiple substituents. When $R^c$, $R^d$ and/or $R^e$ represent multiple substituents, each $R^c$, $R^d$ and $R^e$ can be the same or different.

It will also be appreciated that each group O—P and L indicates, in a general sense, a carboxyl protecting group that can be removed under basic conditions (e.g., alkyl ester), see, e.g., Greene et al. (1991) *Protective Groups in Organic Synthesis,* $2^{nd}$ Edition, New York: Wiley and Kocienski (1994) *Protecting Groups,* New York: Thieme, pp.224–276, and a leaving group (e.g., halogen, sulfonate, and the like), respectively.

The exemplary methods and the examples described herein are illustrative of the present invention and are not to be construed as limiting the scope thereof.

Compositions

In another aspect, the present invention provides pharmaceutical compositions comprising a pharmaceutically acceptable carrier, excipient or diluent and one or more compounds of the present invention.

One embodiment provides the subject compounds combined with a pharmaceutically acceptable excipient such as sterile saline, methylcellulose solutions, detergent solutions or other medium, water, gelatin, oils, etc. The compounds or compositions may be administered alone or in combination with any convenient carrier, diluent, etc., and such administration may be provided in single or multiple dosages. The compositions are sterile, particularly when used for parenteral delivery. However, oral unit dosage forms need not be sterile. Useful carriers include water soluble and water insoluble solids, fatty acids, micelles, inverse micelles, liposomes and semi-solid or liquid media, including aqueous solutions and non-toxic organic solvents. All of the above formulations may be treated with ultrasounds, stirred, mixed, high-shear mixed, heated, ground, milled, aerosolized, pulverized, lyophilized, etc., to form pharmaceutically acceptable compositions.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component. In tablets, the active component is mixed with the carrier having the necessary binding properties in suitable proportions and compacted in the shape and size desired.

The powders and tablets preferably contain from 5% or 10% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 1000 mg, preferably 1.0 mg to 100 mg according to the particular application and the potency of the active component. The composition can, if desired, also contain other compatible therapeutic agents.

The pharmaceutical compositions and methods of the present invention may further comprise other therapeutically active compounds, as noted herein, useful in the treatment of metabolic disorders, cardiovascular diseases, inflammatory conditions or neoplastic diseases and pathologies associated therewith (e.g., diabetic neuropathy) or other adjuvant. In many instances, compositions which include a compound of the invention and an alternative agent have additive or synergistic effects when administered.

Methods of Use

In another aspect, the present invention provides methods for treating a metabolic disorder, cardiovascular disease, an inflammatory condition or a neoplastic disease, comprising administering to a subject in need thereof a therapeutically effective amount of at least one compound of the present invention.

In another aspect, the present invention provides methods of treating a condition or disorder mediated by PPARδ. These methods comprise administering to a subject in need thereof, a therapeutically effective amount of a compound of the present invention. The "subject" is defined herein to include animals such as mammals, including, but not limited to, primates (e.g., humans), cows, sheep, goats, horses, dogs, cats, rabbits, rats, mice and the like.

In another aspect, the invention provides methods for treating a condition or disorder responsive to PPARδ modulation, comprising administering to a subject in need thereof, a therapeutically effective amount of a compound of the present invention.

The present invention also provides methods of elevating HDL cholesterol levels, methods of reducing LDL cholesterol levels and methods of reducing triglyceride levels, each comprising administering to a subject in need thereof, a therapeutically effective amount of a compound of the present invention.

The invention further provides methods of modulating PPARδ, comprising contacting a cell with a compound of the present invention. Preferably, the compound is an agonist of PPARδ.

Diseases and conditions associated with lipid metabolism, inflammation and cell proliferation can be treated with the present compounds and compositions. In one group of embodiments, diseases or conditions, including chronic diseases, of humans or other species can be treated with activators of PPARδ function. These diseases or conditions include: (1) metabolic disorders, such as hypercholesterolemia, hyperlipidemia, dyslipidemia (e.g., elevated LDL cholesterol, elevated total cholesterol, low HDL cholesterol), mixed dyslipidemia, hypertriglyceridemia, hyperglycemia, diabetes, obesity, syndrome X, eating disorders, insulin resistance and hyperinsulinemia, (2) cardiovascular diseases, including, but not limited to, aneurysm, atherosclerosis, arteriosclerosis, cardiomyopathy, congestive heart failure, coronary artery disease, hypertension, ischemia/reperfusion, restenosis and vascular stenosis, (3) inflammatory conditions or diseases such as atherosclerosis, rheumatoid arthritis, osteoarthritis, prosthetic joint failure, allergic diseases (e.g., systemic anaphylaxis or hypersensitivity responses, drug allergies, insect sting allergies and food allergies), inflammatory bowel diseases (e.g., Crohn's disease, ulcerative colitis, ileitis, enteritis, gastritis and mucosal inflammation resulting from infection, the enteropathy provoked by non-steroidal anti-inflammatory drugs), vaginitis, psoriasis and inflammatory dermatoses (e.g., dermatitis, eczema, atopic dermatitis, allergic contact dermatitis, urticaria and bum injury), vasculitis, spondyloarthropathies, scleroderma, asthma and respiratory allergic diseases (e.g., allergic rhinitis, hypersensitivity lung diseases, adult respiratory distress syndrome, cystic fibrosis, and the like), (4) autoimmune diseases, (e.g., rheumatoid arthritis, psoriatic arthritis, multiple sclerosis, systemic lupus erythematosus, type I diabetes, glomerulonephritis, and the like), (5) graft rejection (including allograft rejection and graft-v-host disease) and conditions associated therewith, (6) inflammatory sequelae of viral or bacterial infections, including septic shock, (7) other diseases in which undesired inflammatory responses are to be inhibited, e.g., atherosclerosis, myositis, neurodegenerative diseases (e.g., Alzheimer's disease), encephalitis, meningitis, hepatitis, nephritis, sepsis, sarcoidosis, conjunctivitis, otitis, chronic obstructive pulmonary disease, sinusitis, myocarditis, glaucoma and Behcet's syndrome, (8) neoplastic diseases such as solid tumors, skin cancer, melanoma, lymphoma and endothelial cancers, e.g., breast cancer, lung cancer, colorectal cancer, prostate cancer, kidney cancer, liver cancer, stomach cancer, bladder cancer, ovarian cancer and cancer of the gastrointestinal tract, and (9) other conditions and diseases that are sensitive or responsive to modulation of PPARδ function.

Activators of PPARδ function can also be used to treat diseases or conditions responsive to iNOS or TNF modulation or mediated by iNOS or TNF, including (1) inflammatory conditions and immune disorders, e.g., rheumatoid arthritis, osteoarthritis, prosthetic joint failure, ulcerative colitis, Crohn's disease and other inflammatory bowel diseases, gastritis and mucosal inflammation resulting from infection, enteropathy provoked by non-steroidal antiinflammatory drugs, adult respiratory distress syndrome, asthma, cystic fibrosis, or chronic obstructive pulmonary disease, myocarditis, multiple sclerosis, diabetes melitus and complications thereof, glomerulonephritis, dermatitis, psoriasis, eczema, urticaria, glaucoma, organ transplant rejection, systemic lupus erythematosis, inflammatory sequelae of viral or bacterial infections, atherosclerosis, injury following hypoxic or ischemic insults (with or without reperfusion), for example, cerebral or cardiac, (2) shock states, e.g., septic shock, hemorrhagic shock, traumatic shock, or shock caused by fulminant hepatic failure or by therapy with cytokines such as TNF, IL-1 and IL-2 or therapy with cytokine-inducing agents, for example 5,6-dimethylxanthenone acetic acid, (3) disorders of gastrointestinal motility, e.g., ileus, and (4) diseases of the central nervous system (CNS), e.g., migraine, psychosis, anxiety, schizophrenia, sleep disorders, cerebral ischemia, CNS trauma, epilepsy, multiple sclerosis, AIDS dementia, chronic neurodegenerative disease such as Lewy Body Dementia, Huntington's disease, Parkinson's disease or Alzheimer's disease, acute and chronic pain and conditions in which non-adrenergic non-cholinergic nerves may be implicated, such as priapism, obesity and hyperphagia.

Depending on the disease to be treated and the subject's condition, the compounds and compositions of the present invention may be administered by oral, parenteral (e.g., intramuscular, intraperitoneal, intravenous, intraduodenal, ICV, intracisternal injection or infusion, subcutaneous injection or implant), inhalation, nasal, vaginal, rectal, sublingual, transdermal or topical routes of administration and may be formulated, alone or together, in suitable dosage unit formulations containing conventional non-toxic pharmaceutically acceptable carriers, adjuvants and vehicles appropriate for each route of administration. The present invention also contemplates administration of the compounds of the present invention in a depot formulation, in which the active ingredient is released over a defined time period.

In therapeutic use for the treatment of metabolic disorders, cardiovascular diseases, inflammatory conditions, neoplastic diseases, immune disorders, shock states, disorders of gastrointestinal motility or CNS diseases described herein, the compounds utilized in the pharmaceutical method of the invention may be administered at the initial dosage of about 0.001 mg/kg to about 100 mg/kg daily. A daily dose range of about 0.1 mg/kg to about 10 mg/kg is preferred. The dosages, however, may be varied depending upon the requirements of the patient, the severity of the condition being treated, and the compound being employed. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. For convenience, the total daily dosage may be divided and administered in portions during the day, if desired.

The foregoing compounds and compositions may be advantageously combined with the carbon atoms to which they are attached and/or used in combination with agents useful in the treatment of metabolic disorders, cardiovascular diseases, inflammatory conditions, neoplastic diseases, immune disorders, shock states, gastrointestinal motility disorders or CNS diseases and pathologies associated therewith (e.g., diabetic neuropathy). In many instances, administration of the subject compounds or compositions in conjunction with these alternative agents enhances the efficacy of such agents. Accordingly, in some instances, the present compounds and compositions, when combined with the carbon atoms to which they are attached or administered in combination with, e.g., antidiabetic agents, can be used in dosages which are less than the expected amounts when used alone, or less than the calculated amounts for combination therapy.

For example, in the treatment of inflammation, the present compounds may be used in conjunction with an antiinflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin receptor antagonist, such as an interleukin-1 receptor antagonist, an NMDA receptor antagonist, an inhibitor of nitric oxide or an inhibitor of the synthesis of nitric oxide, a non-steroidal antiinflammatory agent, or a cytokine-suppressing antiinflammatory agent, for example with a compound such as acetaminophen, aspirin, codeine, fentanyl, ibuprofen, indomethacin, ketorolac, morphine, naproxen, phenacetin, piroxicam, a steroidal analgesic, sufentanyl, sulindac, tenidap, and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxy-ephedrine; an antitussive such as codeine, hydrocodone, caramiphen, carbetapentane, or dextramethorphan; a diuretic; and a sedating or non-sedating antihistamine. Each of the above agents may be administered, by a route and in an amount commonly used therefor, contemporaneously or sequentially with a compound of the present invention. When a compound of the present invention is used contemporaneously with one or more other drugs, in some cases a pharmaceutical composition containing such other drugs in addition to the compound of the present invention may be preferred. Accordingly, the pharmaceutical compositions of the present invention include those that also contain one or more other active ingredients, in addition to a compound of the present invention. Examples of other active ingredients that may be combined with the carbon atoms to which they are attached with a compound of the present invention, either administered separately or in the same pharmaceutical compositions, include, but are not limited to: (a) VLA-4 antagonists, (b) corticosteroids, such as beclomethasone, methylprednisolone, betamethasone, prednisone, prednisolone, dexamethasone, fluticasone and hydrocortisone, and corticosteroid analogs such as budesonide; (c) immunosuppressants such as cyclosporine (cyclosporine A, Sandimmune®, Neoral®), tacrolimus (FK-506, Prograf®), rapamycin (sirolimus, Rapamune®) and other FK-506 type immunosuppressants, and mycophenolate, e.g., mycophenolate mofetil (CellCept®); (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine, pyrilamine, astemizole, terfenadine, loratadine, cetirizine, fexofenadine, descarboethoxyloratadine, and the like; (e) non-steroidal anti-asthmatics such as β2-agonists (e.g., terbutaline, metaproterenol, fenoterol, isoetharine, albuterol, bitolterol and pirbuterol), theophylline, cromolyn sodium, atropine, ipratropium bromide, leukotriene antagonists (e.g., zafirlukast, montelukast, pranlukast, iralukast, pobilukast and SKB-106,203), leukotriene biosynthesis inhibitors (zileuton, BAY-1005); (f) non-steroidal antiinflammatory agents (NSAIDs) such as propionic acid derivatives (e.g., alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid and tioxaprofen), acetic acid derivatives (e.g., indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac), fenamic acid derivatives (e.g., flufenamic acid, meclofenamic acid, mefenamic acid, niflumic acid and tolfenamic acid), biphenylcarboxylic acid derivatives (e.g., diflunisal and flufenisal), oxicams (e.g., isoxicam, piroxicam, sudoxicam and tenoxicam), salicylates (e.g., acetyl salicylic acid and sulfasalazine) and the pyrazolones (e.g., apazone, bezpiperylon, feprazone, mofebutazone, oxyphenbutazone and phenylbutazone); (g) cyclooxygenase-2 (COX-2) inhibitors such as celecoxib (Celebrex®) and rofecoxib (Vioxx®); (h) inhibitors of phosphodiesterase type IV (PDE-IV); (i) other agonists of the PPARs, especially PPARα and PPARγ; (j) cholesterol lowering agents such as HMG-CoA reductase inhibitors (lovastatin, simvastatin, pravastatin, fluvastatin, atorvastatin and other statins), bile acid sequestrants (e.g., cholestyramine and colestipol), nicotinic acid (niacin), fibric acid derivatives (gemfibrozil, clofibrate, fenofibrate and benzafibrate), probucol and nitroglycerin; (k) anti-diabetic agents such as insulin, sulfonylureas (e.g., glyburide, meglinatide), biguanides, e.g., metformin (Glucophage®), α-glucosidase inhibitors (acarbose), thiazolidindione compounds, e.g., rosiglitazone (Avandia®), troglitazone (Rezulin®), ciglitazone, pioglitazone (Actos®) and englitazone; (1) preparations of interferon beta (interferon β-1 α, interferon β-1 β); (m) etanercept, (n) antibody therapies such as orthoclone (OKT3), daclizumab (Zenapax®), basiliximab (Simulect®) and infliximab (Remicade®), (o) multiple sclerosis therapeutic agents such as interferon β-1β (Betaseron®), interferon β-1α (Avonex®), azathioprine (Imurek®, Imuran®), glatiramer acetate (Capoxone®), a glucocorticoid (e.g., prednisolone) and cyclophosphamide, (p) β3 adrenergic receptor agonists, leptin or derivatives thereof, and neuropeptide Y (e.g., NPY5) antagonists; (q) other compounds such as 5-aminosalicylic acid and prodrugs thereof, (r) chemotherapeutic agents such as DNA-alkylating agents (e.g., cyclophosphamide, ifosfamide), antimetabolites (e.g., azathioprene, 6-mercaptopurine, methotrexate, a folate antagonist, and 5-fluorouracil, a pyrimidine antagonist), microtubule disruptors (e.g., vincristine, vinblastine, paclitaxel, docetaxel, colchicine, nocodazole and vinorelbine), DNA intercalators (e.g., doxorubicin, daunomycin and cisplatin), DNA synthesis inhibitors such as hydroxyurea, DNA cross-linking agents, e.g., mitomycin C, (s) hormone therapy (e.g., tamoxifen, and flutamide), (t) a nitric oxide synthase (NOS) inhibitor (e.g., an iNOS or an nNOS inhibitor), and (u) an inhibitor of the release, or action, of tumor necrosis factor α (TNF α). The weight ratio of the compound of the present invention to the second active ingredient may be varied and will depend upon the effective dose of each ingredient. Generally, an effective dose of each will be used. Thus, for example, when a compound of the present invention is combined with the carbon atoms to which they are attached with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

The following examples are offered by way of illustration and are not intended to limit the scope of the invention.

EXAMPLES

Reagents and solvents used below can be obtained from commercial sources such as Aldrich Chemical Co. (Milwaukee, Wis., USA). $^1$H-NMR spectra were recorded on a Bruker DPX 300 MHz NMR spectrometer, a JEOL JNM-A 300 MHz WB NMR spectrometer, a Varian Gemini 400 MHz NMR spectrometer, a Bruker ARX 400 MHz NMR spectrometer or a Varian INNOVA 400 MHz NMR spectrometer. Significant peaks are tabulated in the order: number of protons, multiplicity (s, singlet; d, doublet; t, triplet; q, quartet; m, multiplet; br s, broad singlet) and coupling constant(s) in Hertz (Hz). Electron Ionization (EI) mass spectra were recorded on a Hewlett Packard 5989A mass spectrometer. Mass spectrometry results are reported as the ratio of mass over charge, followed by the relative abundance of each ion (in parentheses). In tables, a single m/e value is reported for the M+H (or as noted M–H) ion containing the most common atomic isotopes. Isotope patterns correspond to the expected formula in all cases. Electrospray ionization (ESI) mass spectrometry analysis was conducted on a Hewlett-Packard 1100 MSD electrospray mass spectrometer using the HP1100 HPLC for sample delivery. Normally the analyte was dissolved in methanol at 0.1 mg/mL and 1 microliter (μL) was infused with the delivery solvent into the mass spectrometer which scanned from 100 to 1500 daltons. All compounds could be analyzed in the positive ESI mode, using 1:1 acetonitrile/water with 1% acetic acid as the delivery solvent. The compounds provided below could also be analyzed in the negative ESI mode, using 2 mM NH$_4$OAc in acetonitrile/water as delivery solvent. LCMS was conducted on an Agilent 1100 series LC/MSD.

Example 1

This example illustrates the preparation of {2-methyl-4-[3-methyl-4-(4-trifluoromethyl-benzyloxy)-phenylsulfanyl]-phenoxy}-acetic acid (1).

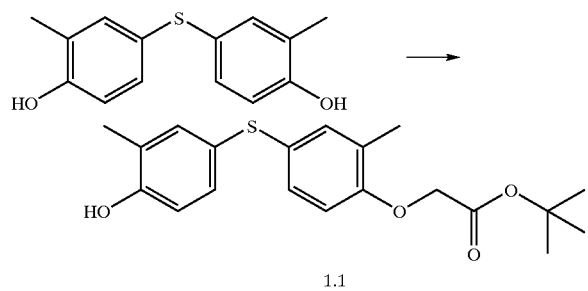

1.1

[4-(4-Hydroxy-3-methyl-phenylsulfanyl)-2-methyl-phenoxy]-acetic acid tert-butyl ester (1.1). An oven-dried 100 mL round-bottomed flask was charged with bis-(4-hydroxy-3-methylphenyl)-sulfide (8.6 g, 34.9 mmol), finely powdered Cs$_2$CO$_3$ (11.9 g, 36.7 mmol), and anhydrous DMF (35 mL). Next, tert-butyl bromoacetate (5.2 mL, 34.9 mmol, Aldrich) was added dropwise, and the reaction was stirred vigorously overnight at room temperature. The reaction was poured into 500 mL of water and extracted with 3×50 mL of methylene chloride. The combined organics were washed with 2×150 mL of water, dried over Na$_2$SO$_4$, and concentrated to a slightly yellow oil. The mixture was then purified by flash chromatography (SiO$_2$ gel 60, eluted with 10% hexanes in DCM—5% hexanes in DCM—100% DCM). The fractions containing only desired product 1.1 were combined and concentrated to a white solid (3.5 g). The mixed fractions were combined, concentrated, and resubjected to the same chromatography conditions to yield an additional 2.0 g of pure 1.1. $^1$H NMR (400 MHz) (CDCl$_3$) δ 7.13 (2H, m); 7.06 (2H, m); 6.70 (1H, d, J=8.3 Hz); 6.59 (1H, d, J=8.4 Hz); 4.50 (2H, s); 2.23 (3H, s); 2.20 (3H, s); 1.48 (9H, s).

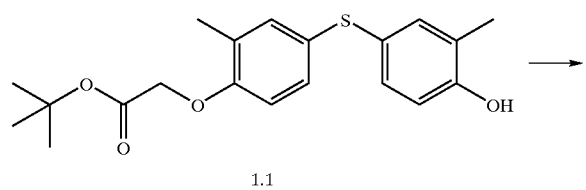

1.1

-continued

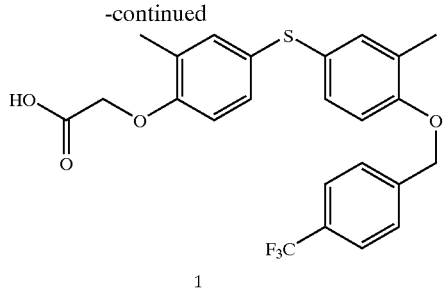

1

{2-Methyl-4-[3-methyl-4-(4-trifluoromethyl-benzyloxy)-phenylsulfanyl]-phenoxy}-acetic acid (1). An oven-dried 100 mL round-bottomed flask was charged with compound 1.1 (400 mg, 1.1 mmol), finely powdered Cs$_2$CO$_3$ (405 mg, 1.2 mmol), and anhydrous DMF (2 mL). 4-(Trifluoromethyl)benzyl bromide (298 mg, 1.1 mmol, Aldrich) was added, and the reaction was stirred vigorously overnight at room temperature. The reaction mixture was poured into 60 mL of water and extracted with 3×20 mL of methylene chloride. The combined organics were washed with 2×50 mL of water, dried over Na$_2$SO$_4$, and concentrated to a slightly yellow oil (422 mg). This crude material was dissolved in methylene chloride (2.5 mL), and trifluoroacetic acid (1.2 mL) was slowly added. The reaction was stirred for 4 h, after which the volatile components were removed in vacuo to reveal a crude pink oil. The crude pink oil was purified using flash chromatography (SiO$_2$ gel 60, eluted with 60% EtOAc/hexanes), and the resulting white solid was recrystallized from methylene chloride/hexanes to give fine white crystals (213 mg). MS ESI m/e: 461.1 (M−H). $^1$H NMR (400 MHz) (CDCl$_3$) δ 7.65 (2H, d, J=8.4 Hz); 7.54 (2H, d, J=8.4 Hz); 7.20 (1H, s); 7.17–7.14 (2H, d, m); 7.10 (11H, dd, J=13.0, 2.4 Hz); 6.77 (1H, d, J=8.4 Hz); 6.65 (1H, d, J=8.4 Hz); 5.12 (2H, s); 4.66 (2H, s); 2.25 (3H, s); 2.24 (3H, s).

Example 4

This example illustrates the preparation of 4-[[3-methyl-4-(4-trifluoromethyl-benzyloxy)phenyl]sulfanyl]-2-propylphenoxy-acetic acid (4)

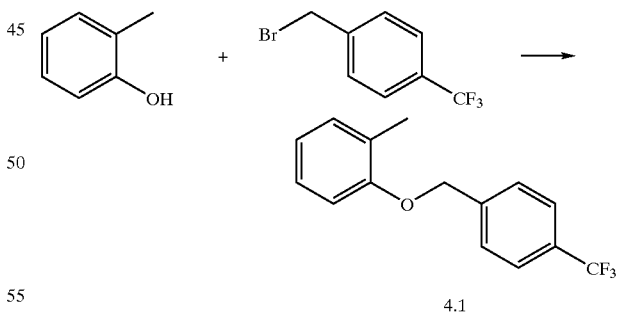

4.1

2-Methyl-1-(4-trifluoromethylbenzyloxy)benzene (4.1). 2-Methylphenol (12.53 g, 115.9 mmol) was dissolved in DMF (60 mL), and stirred at 0° C. To the solution was added K$_2$CO$_3$ (24.03 g, 173.9 mmol) and 4-trifluoromethylbenzyl bromide (23.08 g, 96.6 mmol), and the reaction was stirred at room temperature for 2 h. Water was added to the reaction, and the product was extracted with EtOAc twice. The organic layer was washed with water and brine, dried over Na$_2$SO$_4$, and concentrated in vacuo to give a crude residue. The crude residue was purified using silica gel column chromatography (hexane/EtOAc=30/1) to give 4.1 (25.1 g). $^1$H NMR (400 MHz) (CDCl$_3$) δ 7.64 (2H, d, J=8.2 Hz); 7.56 (2H, d, J=8.2 Hz); 7.18–7.08 (2H, m); 6.90 (1H, t, J=7.2 Hz); 6.84 (1H, d, J=8.1 Hz); 5.14 (2H, s); 2.30 (3H, s).

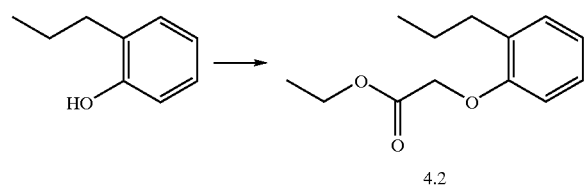

2-Propylphenoxy-acetic acid ethyl ester (4.2). 2-Propylphenol (15.0 g, 110 mmol) was dissolved in DMF (70 mL), and stirred at 0° C. To the solution was added K$_2$CO$_3$ (30.43 g, 220.2 mmol) and ethyl 2-bromoacetate (13.43 mL, 121.1 mmol), and the reaction was stirred at room temperature for 3.5 h. The reaction was diluted with water, and the product was extracted with EtOAc twice. The organic layer was washed with water, brine, dried over Na$_2$SO$_4$, and concentrated in vacuo to give residue. The residue was purified using silica gel column chromatography (hexane/EtOAc=30/1) to give 4.2 (25.4 g). $^1$H NMR (400 MHz) (CDCl$_3$) δ 7.18–7.08 (2H, m); 6.91 (1H, t, J=7.4 Hz); 6.71 (1H, d, J=8.1 Hz); 4.62 (2H, s); 4.25 (2H, q, J=7.1 Hz); 2.68–2.57 (2H, m); 1.70–1.60 (2H, m); 1.29 (3H, t, J=7.1 Hz); 0.95 (3H, t, J=7.4 Hz).

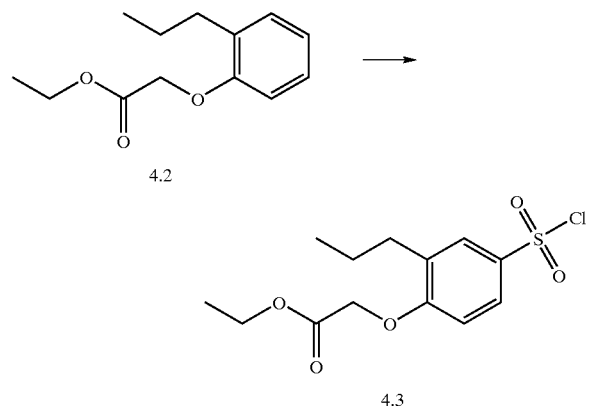

4–Chlorosulfonyl-2-propylphenoxy-acetic acid ethyl ester (4.3). Chlorosulfonic acid (36.59 mL, 550.5 mmol) was cooled to 0° C. under argon atmosphere. The cooled chlorosulfonic acid was added dropwise to compound 4.2 (24.5 g, 110.1 mmol) using a dropping funnel. The reaction was stirred at 0° C. for 30 min. and at room temperature for 4 h. The reaction mixture was poured into ice-water and stirred slowly at 0° C. for 20 min. The precipitated crystals were collected and dried in vacuo using oven at 40° C. to give 4.3 (30.8 g) as pale-yellow crystals. $^1$H NMR (300 MHz) (CDCl$_3$) δ 7.90–7.79 (2H, m); 6.81 (1H, d, J=8.4 Hz); 4.75 (2H, s); 4.28 (2H, q, J=7.1 Hz); 2.79–2.67 (2H, m); 1.77–1.60 (2H, m); 1.30 (3H, t, J=7.1 Hz); 0.97 (3H, t, J=7.3 Hz).

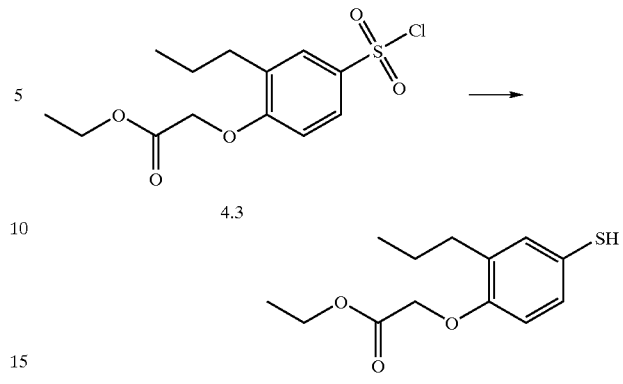

4-Mercapto-2-propylphenoxy-acetic acid ethyl ester (4.4). Compound 4.3 (43.27 g, 134.9 mmol) was dissolved in ethanol (168.6 mL). To the solution was added tin (80.1 g, 674.5mmol) and the reaction was stirred at room temperature for 15 min., then cooled to 0° C. To the reaction was added 4N HCl/dioxane solution (168.6 mL, 674.5 mmol) dropwise at 0° C. Then the reaction was refluxed for 3.5 h. After cooling to room temperature, the reaction mixture was concentrated in vacuo and filtered to remove insoluble materials and the filtrate was concentrated in vacuo to give the residue. The resulting residue was purified using silica gel column chromatography (hexane/EtOAc=10/1) to give 4.4 (27.2 g). $^1$H NMR (400 MHz) (CDCl$_3$) δ 7.13 (1H, d, J=2.3 Hz); 7.09 (1H, dd, J=2.4, 8.4 Hz); 6.60 (1H, d, J=8.4 Hz); 4.59 (2H, s); 4.25 (2H, q, J=7.1 Hz); 3.32(1H, s); 2.63–2.55 (2H, m); 1.68–1.57 (2H, m); 1.28 (3H, t, J=7.1 Hz); 0.95 (3H, t, J=7.4 Hz).

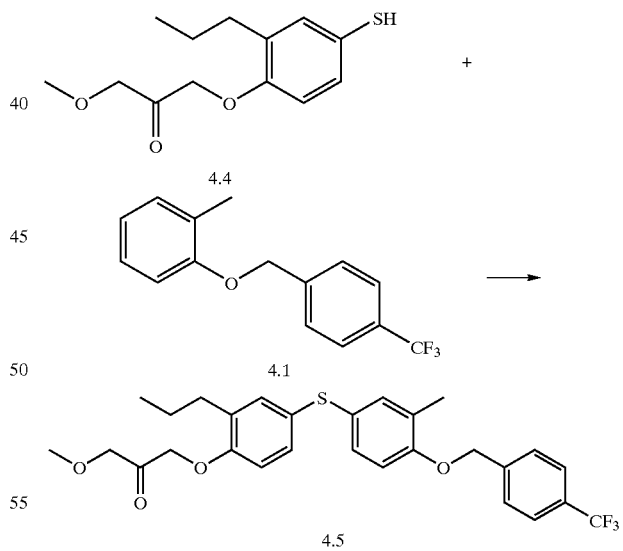

4-[[3-Methyl-4-(4-trifluoromethylbenzyloxy)phenyl] sulfanyl]-2-propylphenoxy-acetic acid ethyl ester (4.5). Compound 4.4 (5.0 g, 19.66 mmol) was dissolved in 1,1,1,3,3,3-hexafluoro-2-propanol (30 mL) under argon atmosphere. To the solution was added compound 4.1 (5.23 g, 19.66 mmol) and [bis(trifluoroacetoxy)iodo]benzene (10.14 g, 23.59 mmol) slowly, while maintaining the reaction temperature between 10° C. and 17° C. After stirring for 15 min, the reaction mixture was concentrated in vacuo to give a residue which was purified using silica gel column chromatography (hexane/EtOAc=20/1) to give 4.5 (6.11 g). $^1$H NMR (400 MHz) (CDCl$_3$) δ 7.64 (2H, d, J=8.2 Hz); 7.54 (2H, d, J=8.1 Hz); 7.20–7.06 (4H, m); 6.76 (1H, d, J=8.4 Hz); 6.62 (1H, d, J=8.4 Hz); 5.11 (2H, s); 4.60 (2H, s); 4.25 (2H, q, J=7.1 Hz); 2.63–2.56 (2H, m); 2.24 (3H, s); 1.67–1.55 (2H, m); 1.28 (3H, t, J=7.1 Hz); 0.92 (3H, t, J=7.4 Hz).

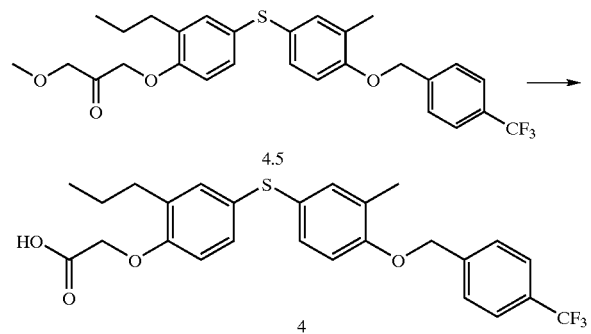

4-[[3-Methyl-4-(4-trifluoromethyl-benzyloxy)phenyl]sulfanyl]-2-propylphenoxy-acetic acid (4). Compound 4.5 (32.7 g, 63.0 mmol) was dissolved in THF (250 mL). To the solution was added 4N LiOH (31.5 mL, 126 mmol) and the reaction was stirred at room temperature for 1 h, after which time water (31.5mL) was added, and the reaction mixture was stirred for 30 min. 2N HCl (70 mL) was then added to the reaction and the THF was removed in vacuo. The residue was diluted with hexane (250 mL) with stirring, and the deposited crystals were collected by filtration and recrystallized from EtOAc—hexane to provide 4 (24.12 g). MS APSI m/e: 489 (M−H). $^1$H NMR (400 MHz) (DMSO-d$_6$) δ 12.90 (1H, brs); 7.76 (2H, d, J=8.2 Hz); 7.67 (2H, d, J=8.2 Hz); 7.20–7.05 (4H, m); 6.99 (1H, d, J=8.6 Hz); 6.81 (1H, d, J=8.4 Hz); 5.23 (2H, s); 4.68 (2H, s); 2.56–2.47 (2H, m); 2.18 (3H, s); 1.60–1.47 (2H, m); 0.85 (3H, t, J=7.4 Hz).

Example 5

This example illustrates the preparation of 4-[[2-methyl-4-(4-trifluoromethyl-benzyloxy)phenyl]sulfonyl]-2-methylphenoxy-acetic acid (5).

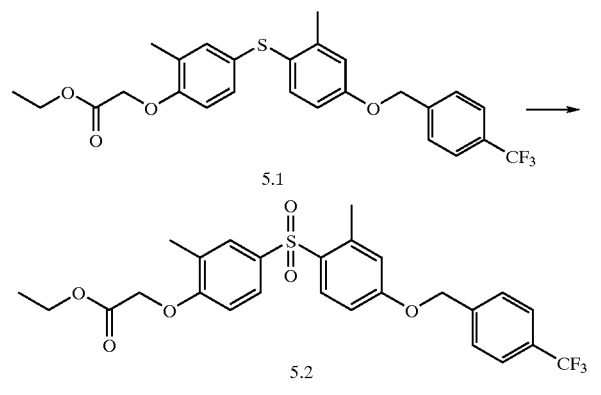

4-[[2-methyl-4-(4-trifluoromethyl-benzyloxy)phenyl]sulfonyl]-2-methylphenoxy-acetic acid ethyl ester (5). Compound 5.1 (90 mg, 0.18 mmol), prepared in a similar manner as described for compound 4.5 (see Example 4, above), was dissolved in dichloromethane (2.0 mL). To the solution was added 70–75% m-chloroperbenzoic acid (100 mg, 41–44 mmol) at 0° C. and the reaction mixture was stirred overnight at room temperature. Saturated NaHCO$_3$ solution (5.0 mL) and NaS$_2$O$_3$ (100 mg) were added to the mixture, which was stirred at room temperature for 1 h. The product was extracted with dichloromethane (5.0 mL), and the organic extracts were successively washed with 1N NaOH solution (5.0 mL) and brine (5.0 mL), dried over Na$_2$SO$_4$, and concentrated in vacuo to give a residue which was purified using silica gel column chromatography (eluted with 0–30% AcOEt/hexane) to give 5.2 (86 mg). $^1$H NMR (400 MHz) (CDCl$_3$) δ 8.12 (1H, m, J=8.8 Hz), 7.70–7.60 (3H, m), 7.60 (1H, s), 7.52 (2H, d, J=8.0 Hz), 6.89 (1H, dd, J=2.5, 8.8 Hz), 6.79 (1H, d, J=2.2 Hz), 6.71 (1H, d, J=8.6 Hz), 5.15 (2H, s), 4.68 (2H, s), 4.25 (2H, q, J=7.1 Hz), 2.42 (3H, s), 2.28 (3H, s), 1.28 (3H, t, J=7.1 Hz).

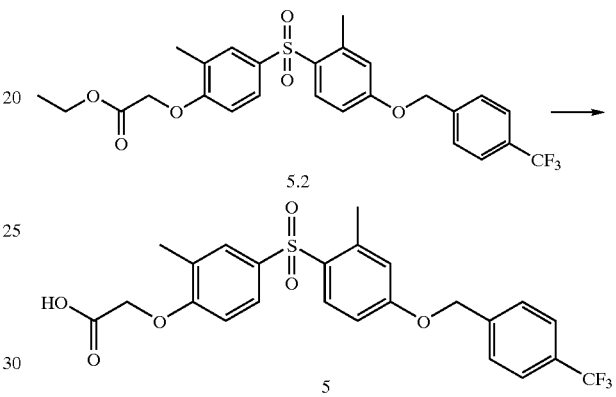

4-[[2-methyl-4-(4-trifluoromethyl-benzyloxy)phenyl]sulfonyl]-2-methylphenoxy-acetic acid (5). Compound 5.2 (82 mg) was saponified in a similar manner as described for compound 4 (see Example 4, above) to give 5 (68 mg). MS APSI m/e: 493 (M−H). $^1$H NMR (400 MHz) (DMSO-d$_6$) δ 13.00 (1H, brs); 8.02 (2H, d, J=8.8 Hz); 7.76 (2H, d, J=8.2 Hz); 7.67–7.59 (4H, m); 7.10 (1H, dd, J=2.6, 8.8 Hz); 7.02–7.00 (2H, m); 5.29 (2H, s); 4.81 (2H, s); 2.36 (3H, s); 2.22 (3H, s)

Example 7

This example illustrates the preparation of 4-[[4-[(4-trifluoromethylphenoxy)methyl]phenyl]sulfanyl]-2-methylphenoxy-acetic acid (7).

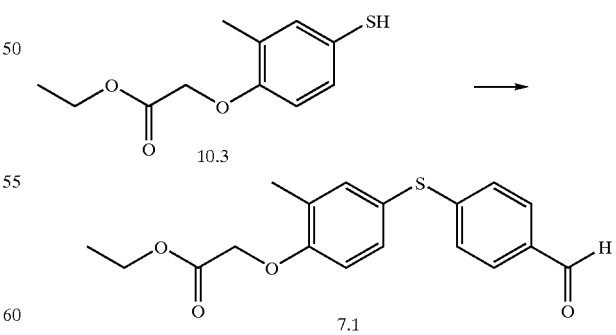

4-[(4-Formylphenyl)sulfanyl]-2-methylphenoxy-acetic acid ethyl ester (7.1). Compound 10.3 (17.6 g, 77.8 mmol) and 4-fluorobenzaldehyde (10.6 g, 85.4 mmol) were coupled in a similar manner as described for compound 10.4 (see Example 10, below). The crude material was purified by flash chromatography (SiO₂ gel 60 N, eluted with AcOEt/hexane=¼). The fractions containing only desired product were combined and concentrated to a slightly yellow oil (19.4 g). ¹H NMR (400 MHz) (CDCl₃) δ 9.89 (1H, s); 7.69 (2H, d, J=8.3 Hz); 7.40–7.30 (2H, m); 7.15 (2H, d, J=8.3 Hz); 6.74 (1H, d, J=8.2 Hz); 4.69 (2H, s); 4.28 (2H, q, J=7.1 Hz); 2.31 (3H, s); 1.30 (3H, t, J=7.1 Hz).

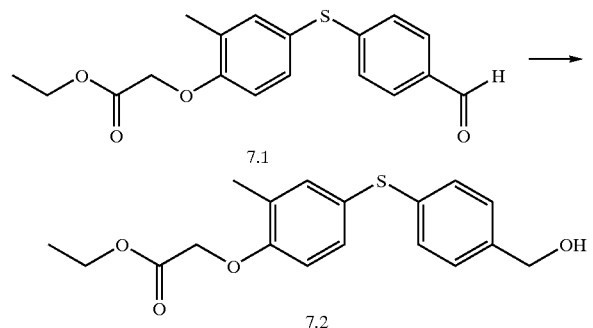

4-[(4-Hydoxymethylphenyl)sulfanyl]-2-methylphenoxy-acetic acid ethyl ester (7.2). Compound 7.1 (32.9 g, 99.6 mmol) was reduced in a similar manner as described for compound 10.5 (see Example 10, below). The crude material was purified by flash chromatography (SiO₂ gel 60 N, eluted with AcOEt/hexane=½). The fractions containing only desired product were combined and concentrated to a slightly yellow oil (30.0 g). ¹H NMR (400 MHz) (CDCl₃) δ 7.30–7.20 (4H, m); 7.18 (2H, d, J=8.2 Hz); 6.67 (1H, d, J=8.4 Hz); 4.64 (2H, s); 4.63 (2H, d, J=5.9 Hz); 4.26 (2H, q, J=7.1 Hz); 2.26 (3H, s); 1.61 (1H, t, J=5.9 Hz); 1.30 (3H, t, J=7.1 Hz).

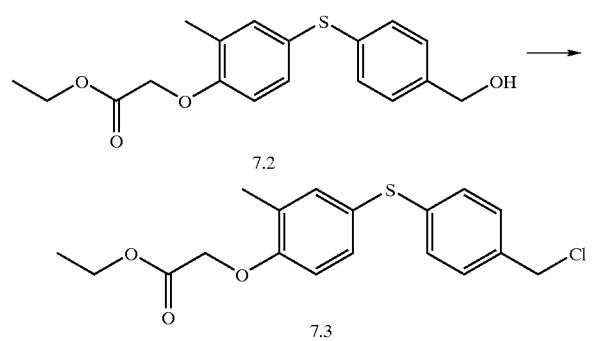

4-[(4-Chloromethylphenyl)sulfanyl]-2-methylphenoxy-acetic acid ethyl ester (7.3). An oven-dried 1 L round-bottomed flask was charged with compound 7.2 (30.0 g, 90.2 mmol) and chloroform (300 mL) and the mixture was cooled to 0° C. Thionyl chloride (7.90 mL, 107 mmol) was added dropwise at 0° C., and the reaction was stirred at room temperature for 1 h. The reaction mixture was concentrated in vacuo to give 7.3 as a slightly yellow oil (33.5 g), which was used in the next step without further purification. ¹H NMR (400 MHz) (CDCl₃) δ 7.30–7.20 (4H, m); 7.12 (2H, d, J=8.3 Hz); 6.68 (1H, d, J=8.4 Hz); 4.65 (2H, s); 4.53 (2H, s); 4.27 (2H, q, J=7.1 Hz); 2.27 (3H, s); 1.30 (3H, t, J=7.1 Hz).

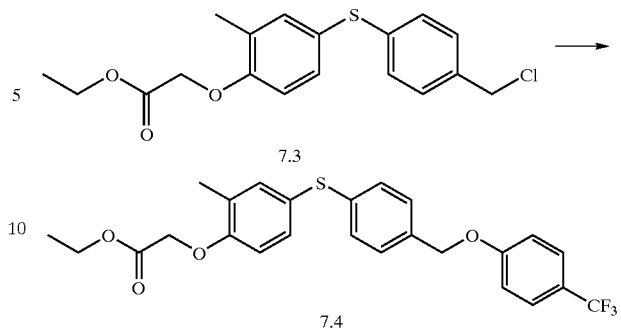

4-[[4-[(4-Trifluoromethylphenoxy)methyl]phenyl]sulfanyl]-2-methylphenoxy-acetic acid ethyl ester (7.4). An oven-dried 500 mL round-bottomed flask was charged with crude 7.3 (prepared from 7.2 (30.0 g, 90.2 mmol)) and DMF (200 mL) and cooled to 0° C. Next, 4-hydroxybenzotrifluoride (17.5 g, 108 mmol) and K₂CO₃ (24.9 g, 180 mmol) were added at 0° C., and the reaction heated to 70–80° C. and stirred for 2 h. The reaction mixture was poured into ice-water (400 mL), and the product was extracted with toluene (400 mL). The organic layer was successively washed with water (2×300 mL) and brine (400 mL), dried over MgSO₄, and concentrated to give a slightly yellow oil which was purified by flash chromatography (SiO₂ gel 60 N, eluted with AcOEt/hexane=⅙). The fractions containing only desired product were combined and concentrated to a slightly yellow oil (40.9 g). ¹H NMR (400 MHz) (CDCl₃) δ 7.53 (2H, d, J=8.6 Hz); 7.30–7.20 (4H, m); 7.17 (2H, d, J=8.4 Hz); 7.00 (2H, d, J=8.7 Hz); 6.68 (1H, d, J=8.4 Hz); 5.04 (2H, s); 4.66 (2H, s); 4.27 (2H, q, J=7.1 Hz); 2.27 (3H, s); 1.30 (3H, t, J=7.1 Hz).

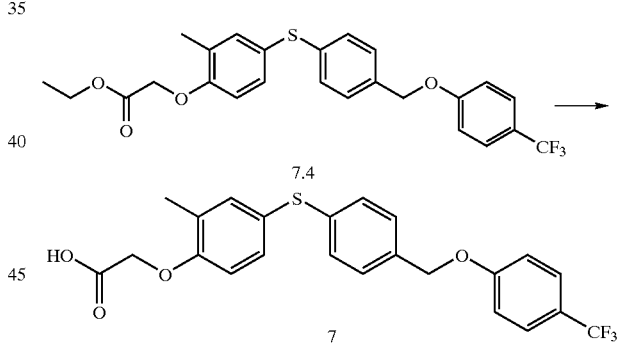

4-[[4-[(4-Trifluoromethylphenoxy)methyl]phenyl]sulfanyl]-2-methylphenoxy-acetic acid (7). A 1 L round-bottomed flask was charged with compound 7.4 (40.9 g, 85.8 mmol), THF (100 mL) and MeOH (100 mL). Next, 2 N NaOH (86 mL, 172 mmol) was added dropwise, and the reaction was stirred at room temperature for 1 h. The solution was neutralized with 2 N HCl (86 mL) and the organic solvent was evaporated to give an aqueous solution and an insoluble oil. The residue was diluted with AcOEt (300 mL) and 1N HCl (300 mL), and partitioned. The organic phase was successively washed with water (400 mL) and brine (400 mL), dried over MgSO₄, and concentrated to give white crystals. Recrystallization from 520 mL of AcOEt/hexane (3/10) gave compound 7 (33.4 g) as white crystals. MS APSI m/e: 447 (M−H). ¹H NMR (400 MHz) (DMSO-d₆) δ 13.0 (1H, brs); 7.64 (2H, d, J=8.8 Hz); 7.38 (2H, d, J=8.3 Hz); 7.30–7.20 (2H, m); 7.16 (4H, d, J=8.3 Hz); 6.89 (1H, d, J=8.5 Hz); 5.14 (2H, s); 4.74 (2H, s); 2.19 (3H, s).

Example 8

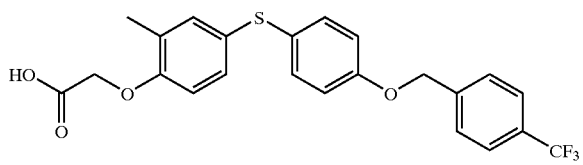

8

Compound 8 was prepared from compound 10.3 and 4-trifluoromethylbenzyloxybenzene according to the method of Example 4. MS APSI m/e: 447 (M−H). $^1$H NMR (300 MHz) (DMSO-d$_6$) δ 13.11 (1H, brs); 7.76 (2H, d, J=8.2 Hz); 7.66 (2H, d, J=8.2 Hz); 7.25 (2H, d, J=8.8 Hz); 7.17 (1H, d, J=2.0 Hz); 7.11 (1H, dd, J=2.0, 8.4 Hz); 7.01 (2H, d, J=8.8 Hz); 6.81 (1H, d, J=8.4 Hz); 5.21 (2H, s); 4.69 (2H, s); 2.15 (3H, s).

Example 9

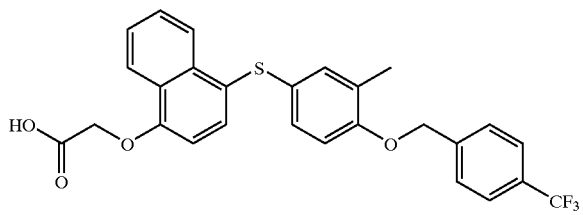

9

Compound 9 was prepared according to the method of Example 4. MS APSI m/e: 497 (M−H). $^1$H NMR (400 MHz) (DMSO-d$_6$) δ 13.12 (1H, brs); 8.28 (2H, t, J=8.9 Hz); 7.75 (2H, d, J=8.2 Hz); 7.65–7.60 (5H, m); 7.13 (1H, d, J=2.0 Hz); 6.98 (1H, dd, J=2.0, 8.6 Hz); 6.92 (2H, dd, J=2.0, 8.2 Hz); 5.18 (2H, s); 4.93 (2H, s); 2.14 (3H, s).

Example 10

This example illustrates the preparation of 4-[[2-chloro-4-[(4-trifluoromethylphenoxy)methyl]phenyl]sulfanyl]-2-methylphenoxy-acetic acid (10).

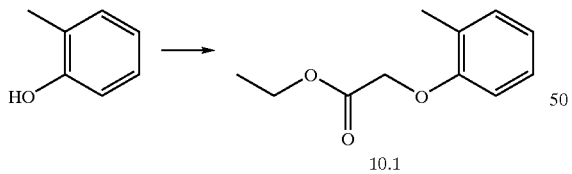

10.1

2-Methylphenoxy-acetic acid ethyl ester (10.1). An oven-dried 300 mL round-bottomed flask was charged with 2-methylphenol (15.0 g, 139 mmol), finely powdered K$_2$CO$_3$ (38.3 g, 277 mmol), and anhydrous DMF (60 mL) and the resulting solution was cooled to 0° C. Next, ethyl bromoacetate (18.5 mL, 167 mmol) was added dropwise at 0° C., and the reaction was stirred vigorously at room temperature for 1 h. The reaction mixture was cooled using an ice-water bath, water (180 mL) was added and the product was extracted twice with AcOEt (200 mL and 100 mL). The combined organics were sequentially washed with 2×100 mL of water and 100 mL of brine, dried over Na$_2$SO$_4$, and concentrated to a slightly yellow oil which was then purified by flash chromatography (SiO$_2$ gel 60 N, eluted with 5% AcOEt/hexane—10% AcOEt/hexane). The fractions containing only desired product were combined and concentrated to provide compound 10.1 as a colorless oil (29.3 g). $^1$H NMR (300 MHz) (CDCl$_3$) δ 7.26–7.13 (2H, m); 6.90 (1H, t, J=7.3 Hz); 6.71 (1H, d, J=8.0 Hz); 4.63 (2H, s); 4.27 (2H, q, J=6.9 Hz); 2.30 (3H, s); 1.30 (3H, t, J=6.9 Hz).

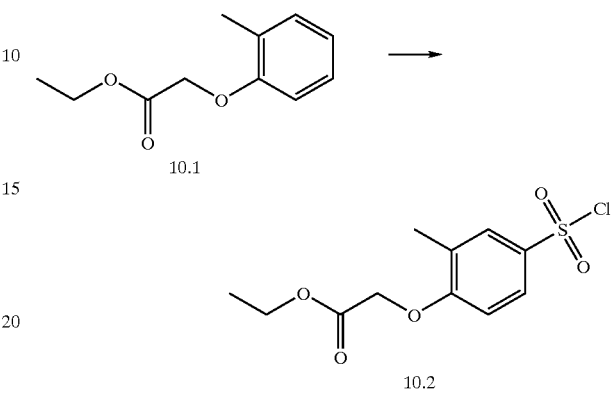

4-Chlorosulfonyl-2-methylphenoxy-acetic acid ethyl ester (10.2). An oven-dried 200 mL round-bottomed flask was charged with chlorosulfonic acid (18.5 mL, 167 mmol). Under N$_2$ flow, compound 10.1 (29.3 g, 139 mmol) was added dropwise using a cannula tube at 0° C., and the reaction was stirred at room temperature for 1.5 h. The reaction mixture was poured into 300 mL of ice-water. Deposited crystals were collected, washed with 3×100 mL of ice-water, and dried in vacuo affording the title compound 10.2 (37.3 g). $^1$H NMR (300 MHz) (CDCl$_3$) δ 7.86–7.84 (2H, m); 6.80 (1H, t, J=9.5 Hz); 4.76 (2H, s); 4.29 (2H, q, J=7.1 Hz); 2.37 (3H, s); 1.31 (3H, t, J=7.1 Hz).

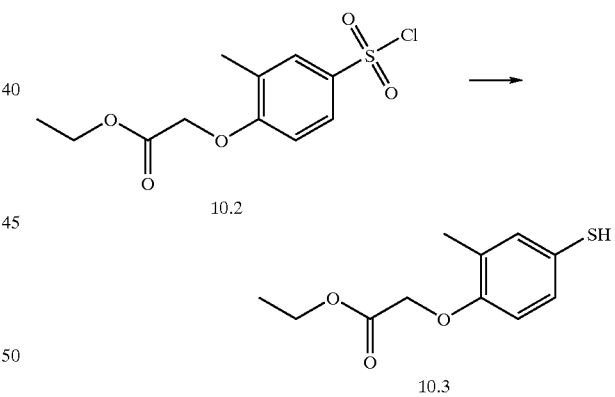

4-Mercapto-2-methylphenoxy-acetic acid ethyl ester (10.3). An oven-dried 1 L round-bottomed flask was charged with compound 10.2 (37.3 g, 127 mmol), finely powdered tin (74.3 g, 626 mmol), and EtOH (157 mL) and the solution was cooled to 0° C. Next, 4 N HCl/dioxane (157 mL, 628 mmol) was added dropwise at 0° C., and the reaction was refluxed for 2.5 h. The reaction mixture was concentrated, and the formed precipitate was filtered off and washed with 300 mL of chloroform. The combined filtrate and washing were concentrated to a slightly yellow oil, which was then purified by flash chromatography (SiO$_2$ gel 60 N, eluted with 10% AcOEt/hexane—20% AcOEt/hexane). The fractions containing only desired product were combined and concentrated to a colorless oil 10.3 (26.1 g). $^1$H NMR (400 MHz) (CDCl$_3$) δ 7.14 (1H, d, J=1.8 Hz); 7.09 (1H, dd, J=2.3, 8.5 Hz); 6.59 (1H, d, J=8.4 Hz); 4.59 (2H, s); 4.25 (2H, q, J=7.1 Hz); 3.32(1H, s); 2.24 (3H, s); 1.29 (3H, t, J=7.1 Hz).

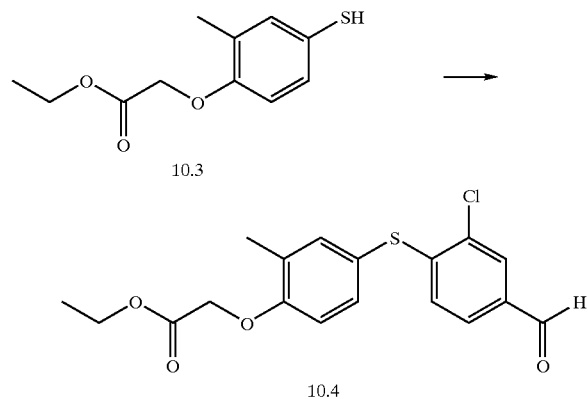

4-[(2-Chloro-4-formylphenyl)sulfanyl]-2-methylphenoxy-acetic acid ethyl ester (10.4). An oven-dried 500 mL round-bottomed flask was charged with finely powdered K$_2$CO$_3$ (31.8 g, 230 mmol) and anhydrous DMF (104 mL). Next, a solution of compound 10.3 (26.1 g, 115 mmol) and 3,4-dichlorobenzaldehyde (21.0 g, 120 mmol) in anhydrous DMF (52 mL) was added dropwise at 90° C., and the reaction was vigorously stirred at same temperature for 1 h. The reaction mixture was poured into 468 mL of ice-water and extracted with 3×200 mL of AcOEt. The combined organics were sequentially washed with 2×200 mL of water and 100 mL of brine, dried over Na$_2$SO$_4$, and concentrated to a yellow oil, which was then purified by flash chromatography (SiO$_2$ gel 60 N, eluted with 10% AcOEt/hexane—20% AcOEt/hexane). The fractions containing only desired product were combined and concentrated to a slightly yellow oil (34.9 g). $^1$H NMR (300 MHz) (CDCl$_3$) δ 9.85 (1H, s); 7.81 (1H, d, J=1.5 Hz); 7.50 (1H, dd, J=1.8, 8.1 Hz); 7.37–7.35 (2H, m); 6.80–6.74 (2H, m); 4.71 (2H, s); 4.30 (2H, q, J=7.2 Hz); 2.32 (3H, s); 1.32 (3H, t, J=7.2 Hz).

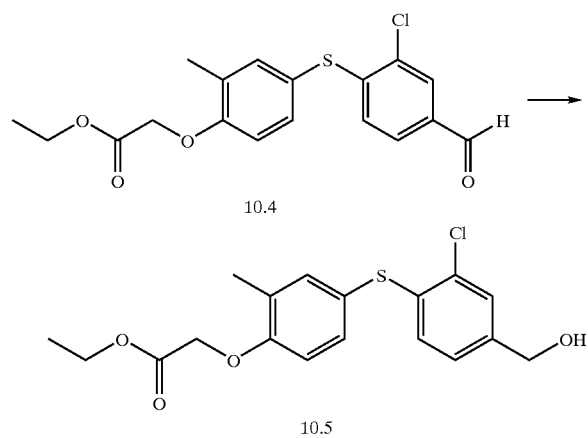

4-[(2-Chloro-4-hydroxymethylphenyl)sulfanyl]-2-methylphenoxy-acetic acid ethyl ester (10.5). An oven-dried 500 mL round-bottomed flask was charged with compound 10.4 (34.9 g, 95.7 mmol), EtOH (175 mL) and THF (17.5 mL). Next, sodium borohydride (1.10 g, 29.1 mmol) was added in 3 portions at 0° C., and the reaction was vigorously stirred at 0° C. for 1 h. The reaction mixture was poured into 463 mL of 0.25 N HCl at 0° C. and the product was extracted with 3×200 mL of AcOEt. The combined organics were washed sequentially with 2×200 mL of water and 100 mL of brine, dried over Na$_2$SO$_4$, and concentrated to a yellow oil, which was then purified by flash chromatography (SiO$_2$ gel 60 N, eluted with 20% AcOEt/hexane—30% AcOEt/hexane). The fractions containing only desired product were combined and concentrated to a slightly yellow oil (33.5 g). $^1$H NMR (400 MHz) (CDCl$_3$) δ 7.37 (1H, d, J=1.5 Hz); 7.31–7.28 (2H, m); 7.05 (1H, dd, J=1.8, 8.2 Hz); 6.77 (1H, d, J=8.2 Hz); 6.72 (1H, d, J=8.3 Hz); 4.67 (2H, s); 4.61 (2H, d, J=5.9 Hz); 4.28 (2H, q, J=7.2 Hz); 2.29 (3H, s); 1.66 (1H, t, J=5.9 Hz); 1.31 (3H, t, J=7.2 Hz).

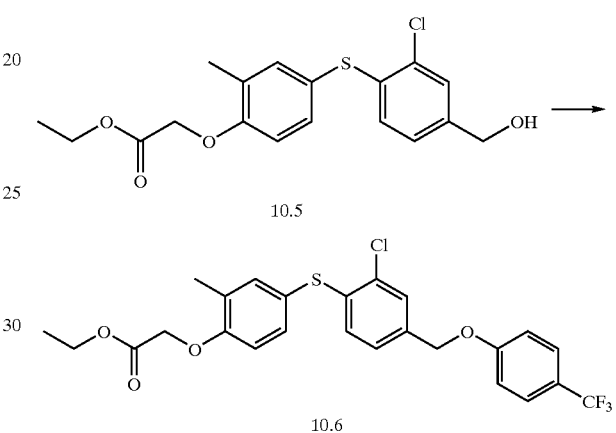

4-[[2-Chloro-4-[(4-trifluoromethylphenoxy)methyl]phenyl]sulfanyl]-2-methylphenoxy-acetic acid ethyl ester (10.6). An oven-dried 1 L round-bottomed flask was charged with compound 10.5 (33.5 g, 91.3 mmol), 4-hydroxybenzotrifluoride (16.3 g, 101 mmol), triphenylphosphine (28.7 g, 109 mmol) and THF (335 mL). Next, diethyl azodicarboxylate (17.0 mL, 110 mmol) was added dropwise at 0° C., and the reaction was stirred at room temperature for 30 min. The reaction mixture was concentrated and purified by flash chromatography (SiO$_2$ gel 60 N, eluted with 10% AcOEt/hexanes—15% AcOEt/hexane—20% AcOEt/hexane). The fractions containing only desired product were combined and concentrated to a slightly yellow oil (43.4 g). $^1$H NMR (400 MHz) (CDCl$_3$) δ 7.54 (2H, d, J=8.8 Hz); 7.42 (1H, d, J=1.6 Hz); 7.34–7.30 (2H, m); 7.09 (1H, dd, J=1.8, 8.2 Hz); 6.99 (2H, d, J=8.8 Hz); 6.76–6.72 (2H, m); 5.00 (2H, s); 4.68 (2H, s); 4.28 (2H, q, J=7.1 Hz); 2.29 (3H, s); 1.31 (3H, t, J=7.2 Hz).

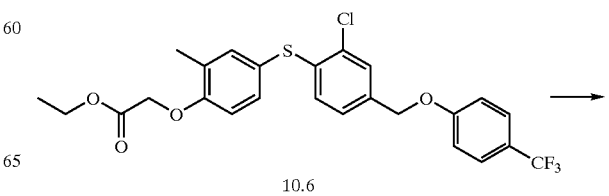

Example 11

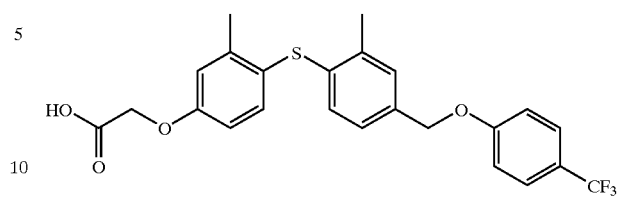

11

Compound 11 was prepared according to the method of Example 10. MS APSI m/e: 461(M–H). $^1$H NMR (400 MHz) (DMSO-$d_6$) δ 12.94 (1H, brs); 7.64 (2H, d, J=8.7 Hz); 7.33 (1H, s); 7.27 (1H, d, J=8.5 Hz); 7.20–7.10 (3H, m); 6.98 (1H, d, J=2.8 Hz); 6.82 (1H, dd, J=2.8, 8.5 Hz); 6.66 (1H, d, J=8.0 Hz); 5.10 (2H, s); 4.70 (2H, s); 2.34 (3H, s); 2.26 (3H, s).

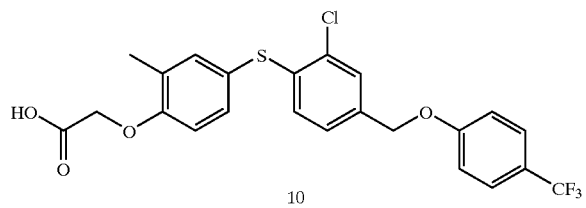

10

4-[[2-Chloro-4-[(4-trifluoromethylphenoxy)methyl]phenyl]sulfanyl]-2-methylphenoxy-acetic acid (10). A 1 L round-bottomed flask was charged with compound 10.6 (43.4 g, 84.9 mmol) and EtOH (386 mL). Next, 4 N NaOH (42 mL, 168 mmol) was added dropwise, and the reaction was stirred at room temperature for 30 min. The reaction was then neutralized using 343 mL of 0.5 N HCl, deposited crystals were collected, washed with 2×100 mL of water, and dried in vacuo. Recrystallization from 508 mL of AcOEt/hexanes (⅜) furnished the title compound 10 (31.1 g) as white crystals. MS APSI m/e: 481 (M–H). $^1$H NMR (400 MHz) (DMSO-$d_6$) δ 12.98 (1H, brs); 7.65 (2H, d, J=8.7 Hz); 7.58 (1H, s); 7.36–7.29 (3H, m); 7.17 (2H, d, J=8.6 Hz); 6.96 (1H, d, J=8.4 Hz); 6.74 (1H, d, J=8.2 Hz); 5.14 (2H, s); 4.77 (2H, s); 2.21 (3H, s).

Example 13

The following compounds were prepared by methods similar to those described in Examples 1, 4 and 5.

TABLE 1

| Compound | R² | R³ | R⁴ | X | R⁶ | R⁷ | R¹' |
|---|---|---|---|---|---|---|---|
| 13.1 | Me | H | H | S | H | cyclopentyl | 3-CF₃ |
| 13.2 | Me | H | H | SO₂ | H | H | 4-CF₃ |
| 13.3 | Me | H | H | S | H | H | H |
| 13.4 | Me | H | H | S | —CH=CH—CH=CH— | | 4-CF₃ |
| 13.5 | Me | H | H | S | H | Me | 4-cyclohexyl |
| 13.6 | Me | H | H | SO₂ | H | Me | 4-cyclohexyl |
| 13.7 | cyclopentyl | H | H | S | H | Me | 4-CF₃ |
| 13.8 | Me | H | H | S | H | n-Pr | 4-CF₃ |
| 13.9 | H | Me | H | S | H | Me | 4-CF₃ |
| 13.10 | i-Pr | H | H | S | H | Me | 4-CF₃ |

TABLE 1-continued

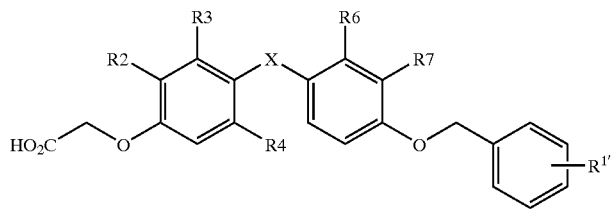

| Compound | R² | R³ | R⁴ | X | R⁶ | R⁷ | R¹' |
|---|---|---|---|---|---|---|---|
| 13.11 | Me | H | H | S | H | i-Pr | 4-CF₃ |
| 13.12 | Me | H | H | S | H | Ph | 4-CF₃ |
| 13.13 | Me | H | H | S | H | Bn | 4-CF₃ |
| 13.14 | H | i-Pr | H | S | H | Me | 4-CF₃ |
| 13.15 | H | Me | Me | S | H | Me | 4-CF₃ |
| 13.16 | —(CH₂)₄— | | H | S | H | H | 4-CF₃ |
| 13.17 | —(CH₂)₄— | | H | S | H | Me | 4-CF₃ |

Example 14

The following compounds were prepared by methods similar to those described in Example 1 and 4.

TABLE 2

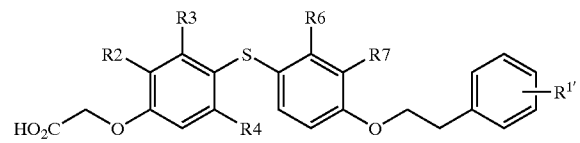

| Compound | R² | R³ | R⁴ | R⁶ | R⁷ | R¹' |
|---|---|---|---|---|---|---|
| 14.1 | i-Pr | H | H | H | Me | 4-CF₃ |
| 14.2 | n-Pr | H | H | H | Me | 4-CF₃ |
| 14.3 | —CH=CH—CH=CH— | | H | H | Me | 4-CF₃ |

Example 15

The following compounds were prepared by methods similar to those described in Examples 7 and 10.

TABLE 3

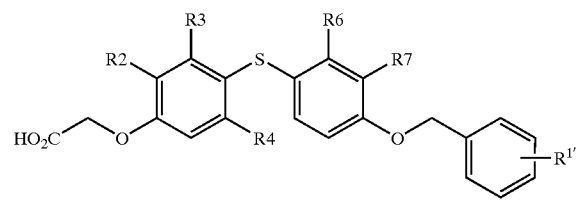

| Compound | R² | R³ | R⁴ | R⁶ | R⁷ | R¹' |
|---|---|---|---|---|---|---|
| 15.1 | Me | H | H | H | H | H |
| 15.2 | Me | H | H | H | H | 2,6-Me₂ |
| 15.3 | Me | H | H | H | H | 2,6-Cl₂ |
| 15.4 | Me | H | H | Me | H | 4-CF₃ |
| 15.5 | Me | H | H | Cl | H | 3-CF₃ |
| 15.6 | H | Me | H | H | H | 4-CF₃ |
| 15.7 | —(CH₂)₄— | | H | H | H | 4-CF₃ |
| 15.8 | i-Pr | H | H | H | H | 4-CF₃ |
| 15.9 | n-Pr | H | H | H | H | 4-CF₃ |

TABLE 3-continued

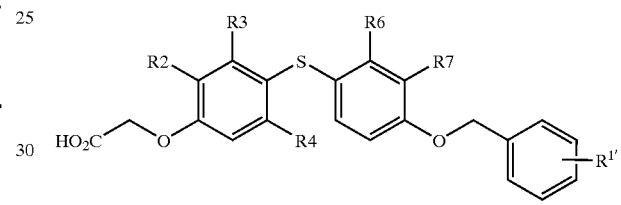

| Compound | R² | R³ | R⁴ | R⁶ | R⁷ | R¹' |
|---|---|---|---|---|---|---|
| 15.10 | Et | H | H | H | H | 4-CF₃ |
| 15.11 | n-Pr | H | H | Cl | H | 4-CF₃ |
| 15.12 | Me | H | H | H | H | 4-Me |
| 15.13 | Me | H | H | H | H | 4-Et |
| 15.14 | Me | H | H | H | H | 4-n-Pr |
| 15.15 | Me | H | H | H | H | 4-Ph |
| 15.16 | Me | H | H | H | H | 4-Ac |
| 15.17 | Me | H | H | H | H | 4-i-Pr |
| 15.18 | Me | H | H | H | H | 4-t-Bu |
| 15.19 | Me | H | H | H | H | 4-t-Pen |
| 15.20 | —CH=CH—CH=CH— | | H | H | H | 4-CF₃ |
| 15.21 | H | H | H | H | H | 4-CF₃ |
| 15.22 | H | Me | Me | H | H | 4-CF₃ |
| 15.23 | H | Me | H | Me | H | 3-CF₃ |
| 15.24 | Me | Me | H | H | H | 4-CF₃ |
| 15.25 | Me | Me | H | H | H | 3-CF₃ |
| 15.26 | Me | H | Me | H | H | 4-CF₃ |
| 15.27 | Me | H | Me | H | H | 3-CF₃ |
| 15.28 | Me | H | Me | Cl | H | 4-CF₃ |
| 15.29 | Me | H | Me | Cl | H | 3-CF₃ |
| 15.30 | Me | H | H | H | H | 3,4-Cl₂ |
| 15.31 | Me | H | H | H | H | 2,4-Cl₂ |
| 15.32 | Me | H | H | H | H | 3-CF₃ |
| 15.33 | Me | H | H | H | H | 2-CF₃ |
| 15.34 | Me | H | H | H | H | 4-CN |
| 15.35 | Me | H | H | H | H | 4-NO₂ |
| 15.36 | Me | H | H | H | H | 4-Cl |

Example 16

The following compounds were prepared by methods similar to those described in Examples 7 and 10.

TABLE 4

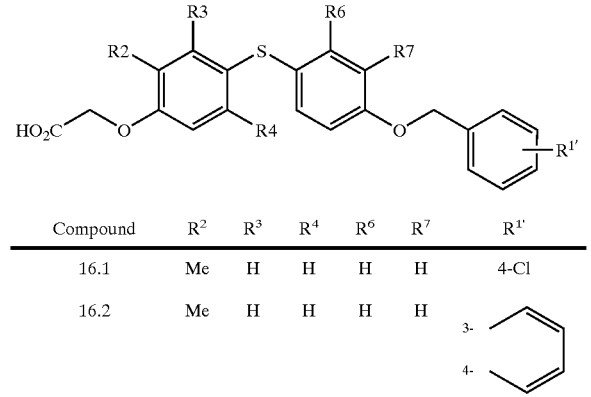

| Compound | $R^2$ | $R^3$ | $R^4$ | $R^6$ | $R^7$ | $R^{1'}$ |
|---|---|---|---|---|---|---|
| 16.1 | Me | H | H | H | H | 4-Cl |
| 16.2 | Me | H | H | H | H | 3-, 4- |

Example 17

The following compounds were prepared by the method outlined in Scheme 11.

TABLE 5

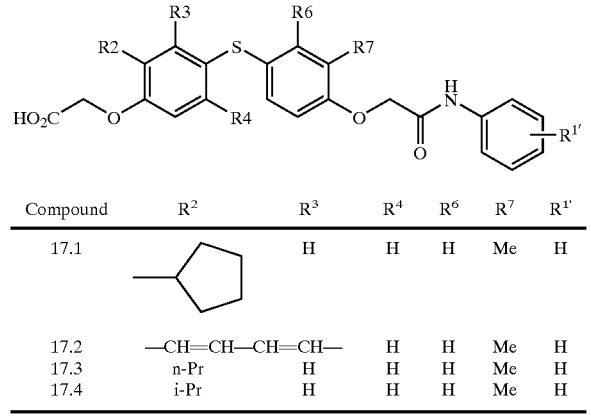

| Compound | $R^2$ | $R^3$ | $R^4$ | $R^6$ | $R^7$ | $R^{1'}$ |
|---|---|---|---|---|---|---|
| 17.1 | cyclopentyl | H | H | H | Me | H |
| 17.2 | —CH=CH—CH=CH— | | H | H | Me | H |
| 17.3 | n-Pr | H | H | H | Me | H |
| 17.4 | i-Pr | H | H | H | Me | H |

Example 18

The following compounds were prepared by method similar to that described in Example 10.

TABLE 6

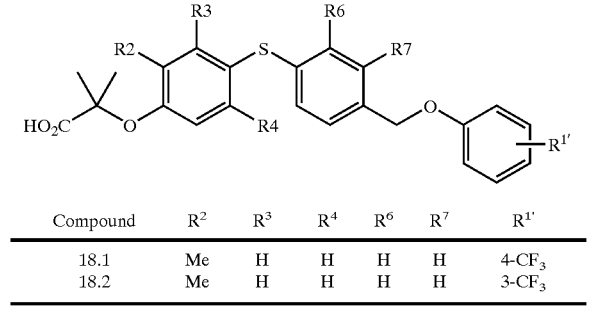

| Compound | $R^2$ | $R^3$ | $R^4$ | $R^6$ | $R^7$ | $R^{1'}$ |
|---|---|---|---|---|---|---|
| 18.1 | Me | H | H | H | H | 4-$CF_3$ |
| 18.2 | Me | H | H | H | H | 3-$CF_3$ |

Example 19

The following compounds were prepared by methods similar to those described in Example 7 and outlined in Schemes 6 and 7.

TABLE 7

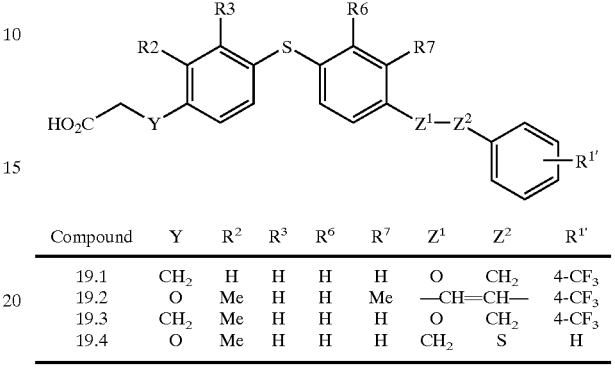

| Compound | Y | $R^2$ | $R^3$ | $R^6$ | $R^7$ | $Z^1$ | $Z^2$ | $R^{1'}$ |
|---|---|---|---|---|---|---|---|---|
| 19.1 | $CH_2$ | H | H | H | H | O | $CH_2$ | 4-$CF_3$ |
| 19.2 | O | Me | H | H | Me | —CH=CH— | | 4-$CF_3$ |
| 19.3 | $CH_2$ | Me | H | H | H | O | $CH_2$ | 4-$CF_3$ |
| 19.4 | O | Me | H | H | H | $CH_2$ | S | H |

Example 20

The following compounds were prepared by methods similar to those described in Examples 1, 7, and 10.

TABLE 8

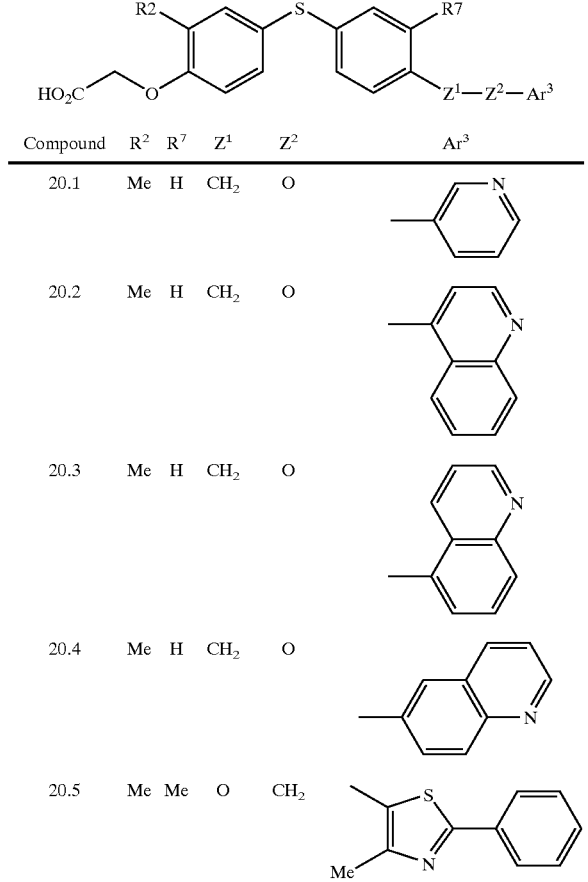

| Compound | $R^2$ | $R^7$ | $Z^1$ | $Z^2$ | $Ar^3$ |
|---|---|---|---|---|---|
| 20.1 | Me | H | $CH_2$ | O | pyridinyl |
| 20.2 | Me | H | $CH_2$ | O | quinolinyl |
| 20.3 | Me | H | $CH_2$ | O | quinolinyl |
| 20.4 | Me | H | $CH_2$ | O | quinolinyl |
| 20.5 | Me | Me | O | $CH_2$ | 4-Me-2-phenyl-thiazol-5-yl |

TABLE 8-continued

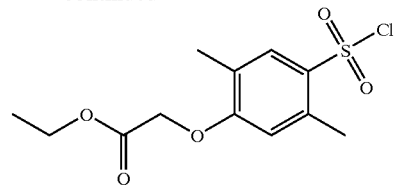

| Compound | R² | R⁷ | Z¹ | Z² | Ar³ |
|---|---|---|---|---|---|
| 20.6 | Me | Me | O | CH₂ | 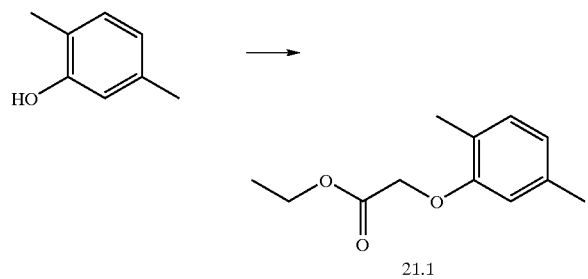 |
| 20.7 | Me | Me | O | (CH₂)₂ | |
| 20.8 | Me | Me | O | CH₂ | |

Example 21

This example illustrates the preparation of 2,5-dimethyl-4-[[2-methyl-4-[(4-trifluoromethyl-phenylamino)methyl]phenyl]sulfanyl]phenoxy-acetic acid (21).

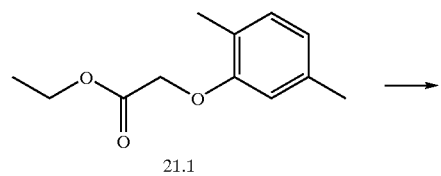

2,5-Dimethylphenoxy-acetic acid ethyl ester (21.1). The title compound was prepared according to the method described for preparing compound 10.1, using 2,5-dimethylphenol as the starting material. ¹H NMR (400 MHz) (CDCl₃) δ 7.03 (1H, d, J=7.5 Hz); 6.72 (1H, d, J=7.5 Hz); 6.52 (1H, s); 4.62 (2H, s); 4.27 (2H, q, J=7.1 Hz); 2.30 (3H, s); 2.25 (3H,s); 1.30 (3H, t, J=7.1 Hz).

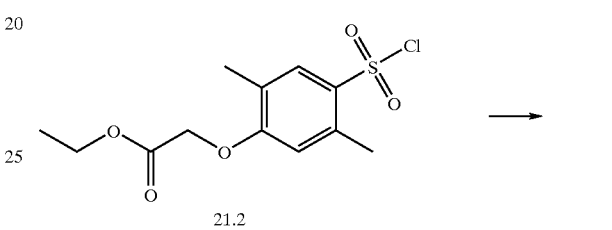

4-Chlorosulfonyl-2,5-dimethylphenoxy-acetic acid ethyl ester (21.2). The title compound was prepared according to the method described for preparing compound 10.2, using compound 21.1 as the starting material. ¹H NMR (400 MHz) (CDCl₃) δ 7.86 (1H, s); 6.61 (1H, s); 4.74 (2H, s); 4.30 (2H, q, J=7.1 Hz); 2.71 (3H, s); 2.31 (3H, s); 1.32 (3H, t, J=7.1 Hz).

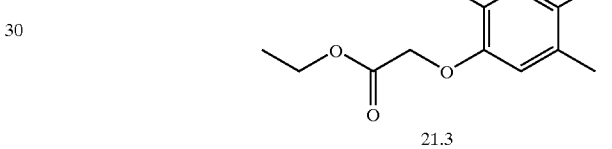

2,5-Dimethyl-4-mercaptophenoxy-acetic acid ethyl ester (21.3). The title compound was prepared according to the method described for preparing compound 10.3, using compound 21.2 as the starting material. ¹H NMR (300 MHz) (CDCl₃) δ 7.11 (1H, s); 6.54 (1H, s); 4.59 (2H, s); 4.26 (2H, q, J=7.2 Hz); 3.10(1H, s); 2.29 (3H, s); 2.21 (3H, s); 1.30 (3H, t, J=7.2 Hz).

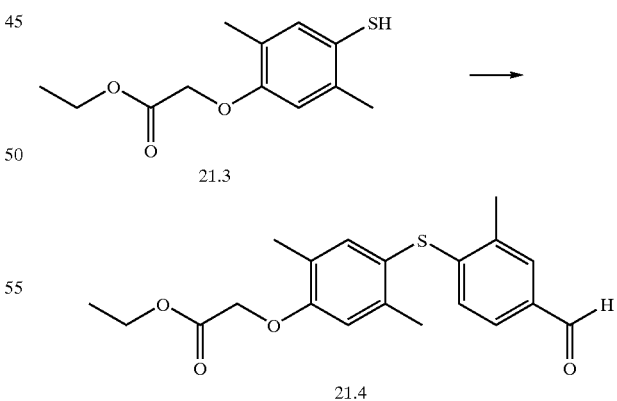

4-[(4-Formyl-2-methylphenyl)sulfanyl]-2,5-dimethylphenoxy-acetic acid ethyl ester (21.4). The title compound was prepared according to the method described for preparing compound 7.1, using compound 21.3 and 4-chloro-3-methylbenzaldehyde as the starting materials. ¹H NMR (400 MHz) (CDCl₃) δ 9.86 (1H, s); 7.62 (1H, s); 7.44

(1H, d, J=8.1 Hz); 7.33(1H, s); 6.70 (1H, s); 6.62 (1H, d, J=8.1 Hz);4.68 (2H, s); 4.29 (2H, q, J=7.1 Hz); 2.46 (3H, s); 2.29 (3H, s); 2.26 (3H, s); 1.32 (3H, t, J=7.1 Hz).

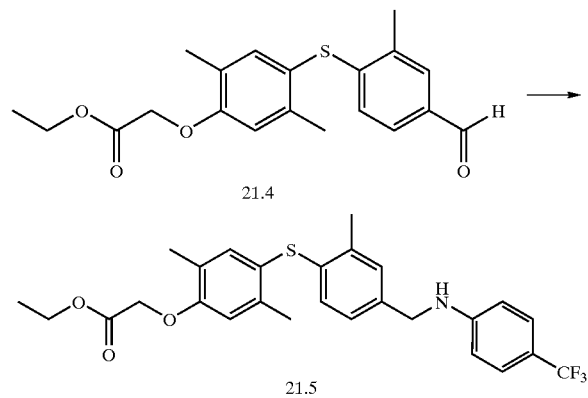

2,5-Dimethyl-4-[[2-methyl-4-[(4-trifluoromethyl-phenylamino)methyl]phenyl]sulfanyl]-phenoxy-acetic acid ethyl ester (21.5). To a stirred solution of compound 21.4 (13.5 g, 37.7 mmol) in CHCl₃ (135 mL) was successively added 4-(trifluoromethyl)aniline (6.07 g, 37.7 mmol) and AcOH (3.24 mL). After stirring at room temperature for 30 min, the reaction was cooled to 0° C., sodium triacetoxyborohydride (12.0 g, 56.6 mmol) was added, and the reaction was stirred at room temperature for 3 h. The reaction mixture was poured into 150 mL of ice-water and the product was extracted with 2×50 mL CHCl₃. The organics were sequentially washed with 150 mL aqueous NaHCO₃ and 150 mL brine, dried over MgSO₄, and concentrated to a yellow oil, which was purified with flash chromatography (SiO₂ gel 60 N, eluted with 10% EtOAc/hexanes—20% EtOAc/hexanes). The fractions containing the desired product were combined and concentrated to yield a colorless solid (18.7 g). ¹H NMR (400 MHz) (CDCl₃) δ 7.38 (2H, d, J=8.5 Hz); 7.20 (1H, s); 7.14 (1H, s); 6.97 (1H, d, J=8.1 Hz); 6.70–6.50 (4H, m); 4.66 (2H, s); 4.40–4.20 (5H, m); 2.38 (3H, s); 2.30 (3H, s); 2.22 (3H, s); 1.31 (3H, t, J=7.1 Hz).

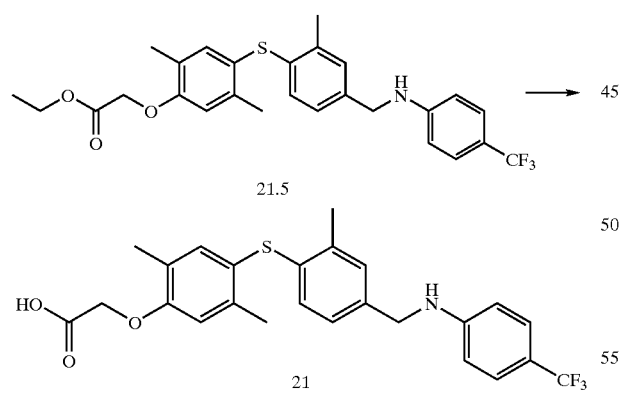

2,5-Dimethyl-4-[[2-methyl-4-[(4-trifluoromethyl-phenylamino)methyl]phenyl]sulfanyl]-phenoxy-acetic acid (21). The title compound was prepared according to the method described for preparing compound 7, using compound 21.5 as starting material. MS APSI m/e: 474 (M–H). ¹H NMR (400 MHz) (DMSO-d₆) δ 12.86 (1H, brs); 7.33 (2H, d, J=8.6 Hz); 7.21 (1H, s); 7.12 (1H, s); 7.05 (1H, d, J=8.1 Hz); 6.87 (1H, s); 6.85 (1H, t, J=5.6 Hz); 6.65 (2H, d, J=8.6 Hz); 6.62 (1H, d, J=8.1 Hz); 4.72 (2H, s); 4.22 (2H, d, J=5.6 Hz); 2.30 (3H, s); 2.23 (3H, s); 2.11 (3H, s).

Example 22

This example illustrates the preparation of (4-{2-chloro-4-[(4-trifluoromethyl-phenylamino)-methyl]-phenylsulfanyl}-5,6,7,8-tetrahydro-naphthalen-1-yloxy)-acetic acid (22).

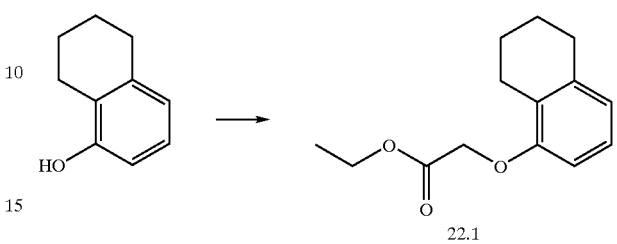

(5,6,7,8-Tetrahydro-naphthalen-1-yloxy)-acetic acid ethyl ester (22.1). The title compound was prepared according to the method described for preparing compound 10.1, using 5,6,7,8-tetrahydro-1-naphthol as the starting material.

¹H NMR (300 MHz) (CDCl₃) δ 7.02 (1H, t, J=7.7 Hz); 6.73 (1H, d, J=7.3 Hz); 6.51 (1H, d, J=8.1 Hz); 4.61 (2H, s); 4.26 (2H, q, J=7.3 Hz); 2.77–2.73 (4H, m); 1.81–1.76 (4H,m); 1.30 (3H, t, J=7.3 Hz).

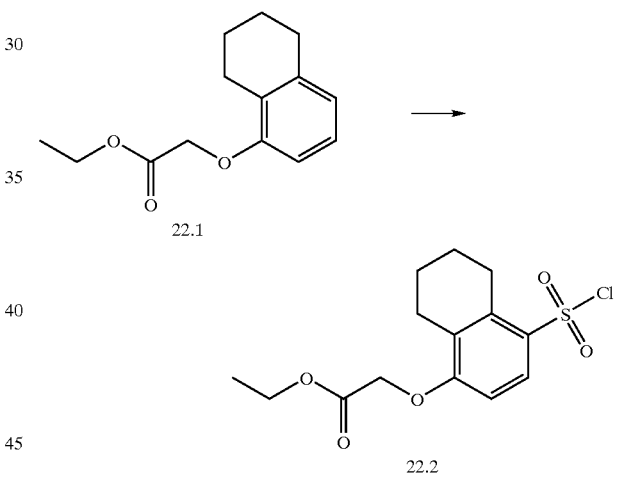

(4-Chlorosulfonyl-5,6,7,8-tetrahydro-naphthalen-1-yloxy)-acetic acid ethyl ester (22.2). The title compound was prepared according to the method described for preparing compound 10.2, using compound 22.1 as the starting material. ¹H NMR (400 MHz) (CDCl₃) δ 7.93 (1H, d, J=8.9 Hz); 6.62 (1H, d, J=9.0 Hz); 4.73 (2H, s); 4.29 (2H, q, J=7.1 Hz); 3.27–3.24 (2H, m); 2.81–2.78 (2H, m); 1.85–1.82 (4H, m); 1.32 (3H, t, J=7.2 Hz).

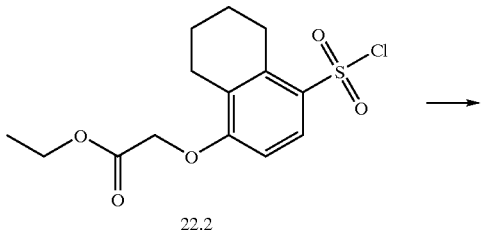

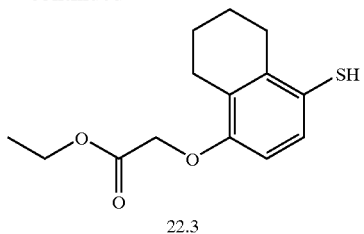

22.3

(4-Mercapto-5,6,7,8-tetrahydro-naphthalen-1-yloxy)-acetic acid ethyl ester (22.3). The title compound was prepared according to the method described for preparing compound 10.3, using compound 22.2 as the starting material. $^1$H NMR (300 MHz) (CDCl$_3$) δ 7.11 (1H, d, J=8.5 Hz); 6.46 (1H, d, J=8.4 Hz); 4.59 (2H, s); 4.26 (2H, q, J=7.1 Hz); 3.10 (1H, s); 2.76–2.65 (4H, m); 1.82–1.74 (4H, m); 1.30 (3H, t, J=7.1 Hz).

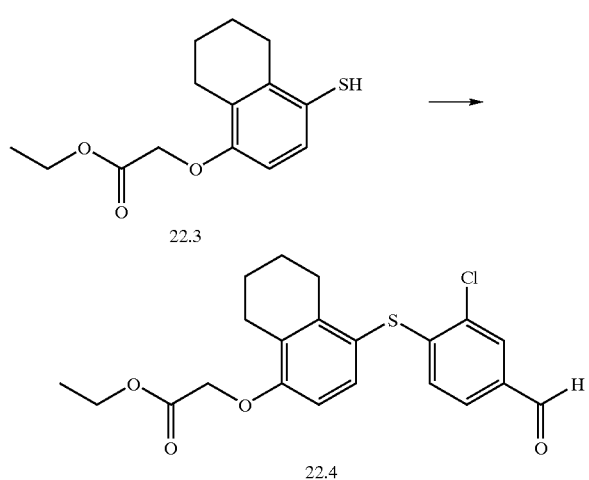

22.3

22.4

[4-(2-Chloro-4-formyl-phenylsulfanyl)-5,6,7,8-tetrahydro-naphthalen-1-yloxy]-acetic acid ethyl ester (22.4). The title compound was prepared according to the method described for preparing compound 10.4, using compound 22.3 and 3,4-dichlorobenzaldehyde as the starting materials. $^1$H NMR (300 MHz) (CDCl$_3$) δ 9.84 (1H, s); 7.82 (1H, d, J=1.8 Hz); 7.49 (1H, dd, J=1.8, 8.4 Hz); 7.40 (1H, d, J=8.4 Hz); 6.63 (1H, d, J=8.4 Hz); 6.59 (1H, d, J=8.0 Hz); 4.70 (2H, s); 4.30 (2H, q, J=7.0 Hz); 2.82–2.70 (4H, m); 1.77–1.70 (4H, m); 1.32 (3H, t, J=7.0 Hz).

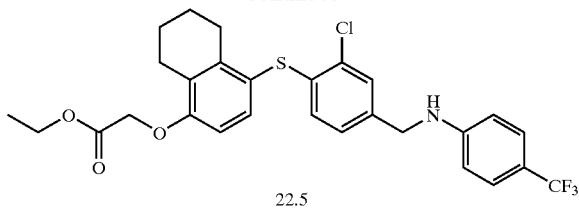

22.5

(4-{2-Chloro-4-[(4-trifluoromethyl-phenylamino)-methyl]-phenylsulfanyl}-5,6,7,8-tetrahydro-naphthalen-1-yloxy)-acetic acid ethyl ester (22.5). The title compound was prepared according to the method described for preparing compound 21.5, using compound 22.4 as the starting material. $^1$H NMR (300 MHz) (CDCl$_3$) δ 7.38 (2H, d, J=8.6 Hz); 7.34 (1H, d, J=8.6 Hz); 7.33 (1H, s); 6.99 (1H, dd, J=1.5, 7.9 Hz); 6.58 (3H, d, J=7.1 Hz); 6.49 (1H, d, J=8.2 Hz); 4.67 (2H, s); 4.37 (1H, brt); 4.28 (2H, q, J=7.2 Hz); 4.28 (2H, d, J=4.5 Hz); 2.78–2.74 (4H, m); 1.74–1.72 (4H, m); 1.31 (3H, t, J=7.1 Hz).

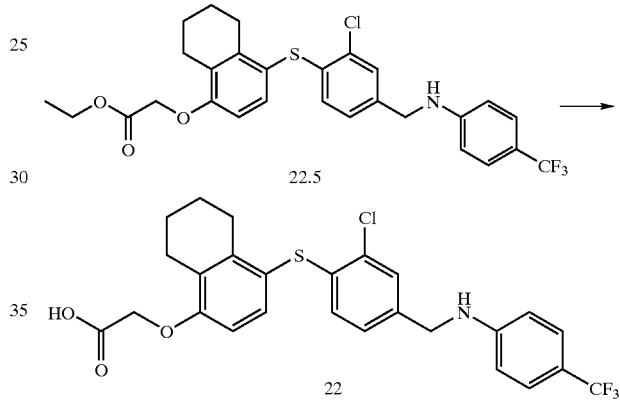

22.5

22

(4-{2-Chloro-4-[(4-trifluoromethyl-phenylamino)-methyl]-phenylsulfanyl}-5,6,7,8-tetrahydro-naphthalen-1-yloxy)-acetic acid (22). The title compound was prepared according to the method described for preparing compound 7, using compound 22.5 as the starting material. MS APSI m/e: 520 (M–H). $^1$H NMR (400 MHz) (DMSO-d$_6$) δ 13.03 (1H, brs); 7.43 (1H, s); 7.35 (2H, d, J=8.6 Hz); 7.31 (1H, d, J=8.5 Hz); 7.16 (1H, d, J=8.2 Hz); 6.98 (1H, t, J=6.0 Hz); 6.78 (1H, d, J=8.6 Hz); 6.64 (2H, d, J=8.6 Hz); 6.48 (1H, d, J=8.2 Hz); 4.75 (2H, s); 4.26 (2H, d, J=5.9 Hz); 2.66–2.63 (4H, m); 1.66–1.65 (4H, m).

Example 23

This example illustrates the preparation of {4-[2-chloro-4-(4-trifluoromethyl-phenoxymethyl)-phenylsulfanyl]-5,6,7,8-tetrahydro-naphthalen-1-yloxy}-acetic acid (23).

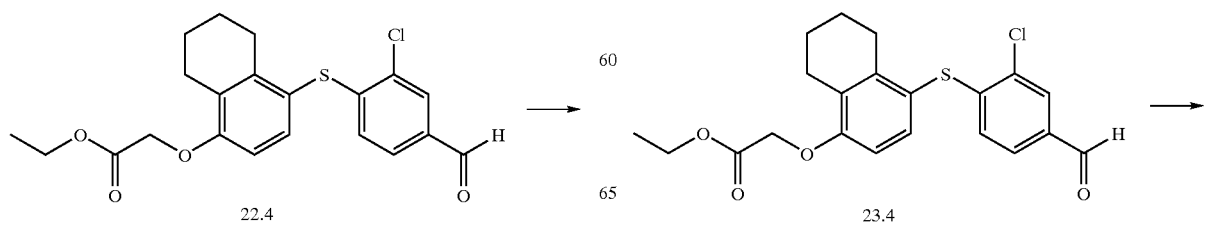

22.4

23.4

-continued

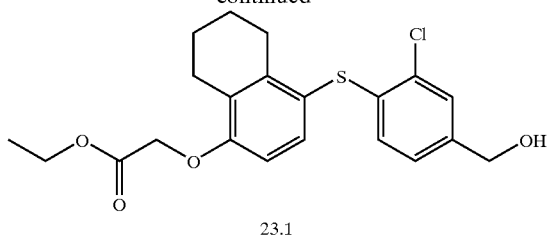
23.1

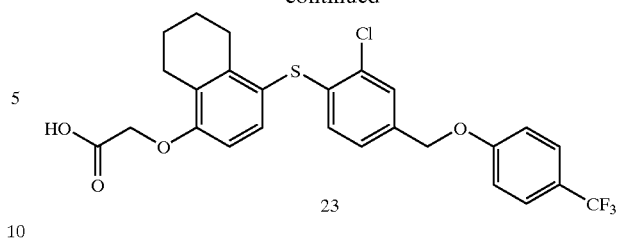
23

[4-(2-Chloro-4-hydroxymethyl-phenylsulfanyl)-5,6,7,8-tetrahydro-naphthalen-1-yloxy]-acetic acid ethyl ester (23.1). The title compound was prepared according to the method described for preparing compound 10.5, using compound 23.4 as the starting material. $^1$H NMR (400 MHz) (CDCl$_3$) δ 7.37 (1H, d, J=1.6 Hz); 7.35 (1H, d, J=8.4 Hz); 7.02 (1H, dd, J=1.6, 8.2 Hz); 6.59 (1H, d, J=8.4 Hz); 6.52 (1H, d, J=8.2 Hz); 4.67 (2H, s); 4.60 (2H, s); 4.29 (2H, q, J=7.1 Hz); 2.80–2.72 (4H, m); 1.75–1.69 (4H, m); 1.32 (3H, t, J=7.1 Hz).

{4-[2-Chloro-4-(4-trifluoromethyl-phenoxymethyl)-phenylsulfanyl]-5,6,7,8-tetrahydro-naphthalen-1-yloxy}-acetic acid (23). The title compound was prepared according to the method described for preparing compound 7, using compound 23.2 as the starting material. MS APSI m/e: 521 (M–H). $^1$H NMR (400 MHz) (DMSO-d$_6$) δ 13.04 (1H, brs); 7.66 (2H, d, J=8.8 Hz); 7.59 (1H, d, J=1.6 Hz); 7.37 (1H, d, J=8.5 Hz); 7.29 (1H, dd, J=1.6, 8.2 Hz); 7.17 (2H, d, J=8.6 Hz); 6.81 (1H, d, J=8.6 Hz); 6.51 (1H, d, J=8.2 Hz); 5.12 (2H, s); 4.77 (2H, s); 2.67–2.64 (4H, m); 1.67–1.66 (4H, m).

Example 24

This example illustrates the preparation of {4-[2-chloro-4-(4-trifluoromethyl-phenoxymethyl)-phenylsulfanyl]-2,5-dimethyl-phenoxy}-acetic acid (24).

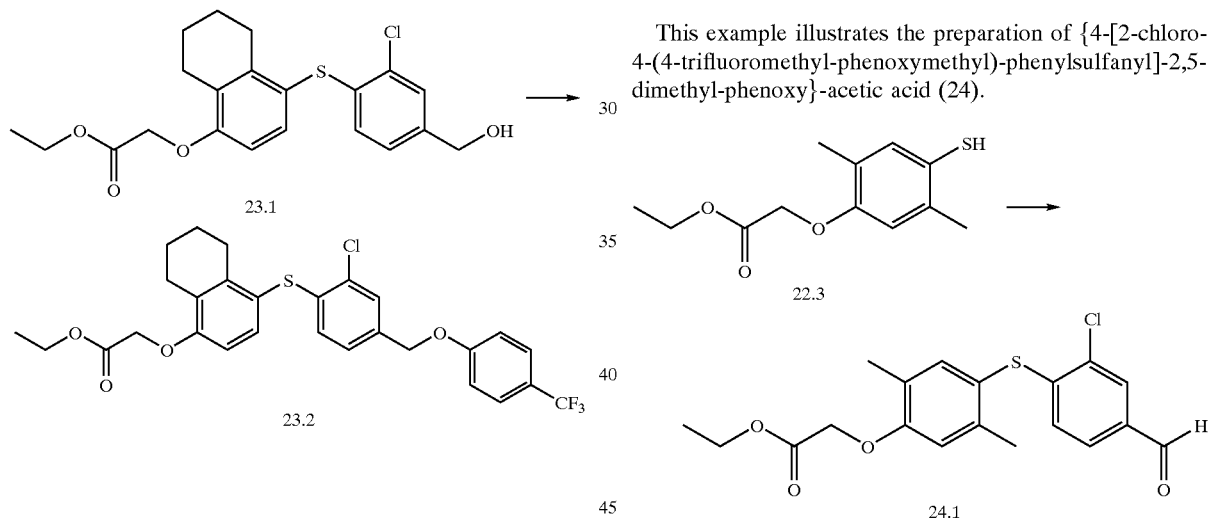

{4-[2-Chloro-4-(4-trifluoromethyl-phenoxymethyl)-phenylsulfanyl]-5,6,7,8-tetrahydro-naphthalen-1-yloxy}-acetic acid ethyl ester (23.2). The title compound was prepared according to the method described for preparing compound 10.6, using compound 23.1 as the starting material. $^1$H NMR (400 MHz) (CDCl$_3$) δ 7.54 (2H, d, J=8.7 Hz); 7.42 (1H, d, J=1.7 Hz); 7.37 (1H, d, J=8.5 Hz); 7.06 (1H, dd, J=1.8, 8.2 Hz); 6.99 (2H, d, J=8.7 Hz); 6.59 (1H, d, J=8.5 Hz); 6.52 (1H, d, J=8.2 Hz); 4.99 (2H, s); 4.68 (2H, s); 4.29 (2H, q, J=7.1 Hz); 2.80–2.73 (4H, m); 1.76–1.70 (4H, m); 1.32 (3H, t, J=7.2 Hz).

[4-(2-Chloro-4-formyl-phenylsulfanyl)-2,5-dimethyl-phenoxy]-acetic acid ethyl ester (24.1). The title compound was prepared according to the method described for preparing compound 10.4, using compound 22.3 and 3,4-dichlorobenzaldehyde as the starting materials. $^1$H NMR (400 MHz) (CDCl$_3$) δ 9.85 (1H, s); 7.82 (1H, d, J=1.7 Hz); 7.49 (1H, dd, J=1.7, 8.2 Hz); 7.36 (1H, s); 6.70 (1H, s); 6.58 (1H, d, J=8.2 Hz); 4.71 (2H, s); 4.31 (2H, q, J=7.1 Hz); 2.31 (3H, s); 2.27 (3H, s); 1.33 (3H, t, J=7.1 Hz).

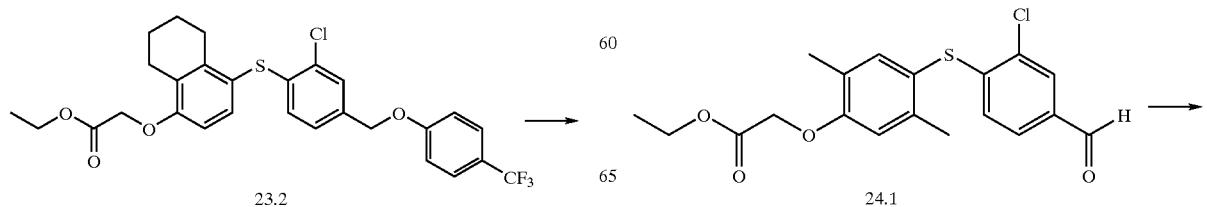

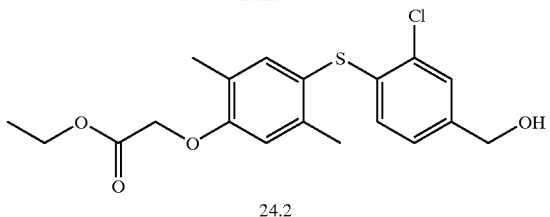

24.2

[4-(2-Chloro-4-hydroxymethyl-phenylsulfanyl)-2,5-dimethyl-phenoxy]-acetic acid ethyl ester (24.2). The title compound was prepared according to the method described for preparing compound 10.5, using compound 24.1 as the starting material. $^1$H NMR (400 MHz) (CDCl$_3$) δ 7.36 (1H, d, J=1.6 Hz); 7.33 (1H, s); 7.01 (1H, dd, J=1.9, 8.1 Hz); 6.67 (1H, s); 6.50 (1H, d, J=8.2 Hz); 4.68 (2H, s); 4.60 (2H, s); 4.30 (2H, q, J=7.2 Hz); 2.31 (3H, s); 2.25 (3H, s); 1.67 (1H, brs); 1.32 (3H, t, J=7.2 Hz).

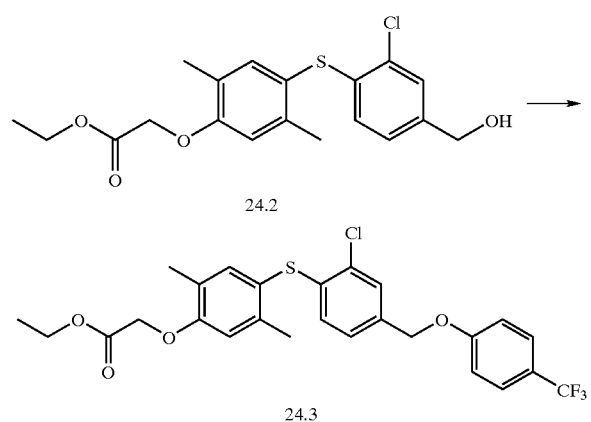

{4-[2-Chloro-4-(4-trifluoromethyl-phenoxymethyl)-phenylsulfanyl]-2,5-dimethyl-phenoxy}-acetic acid ethyl ester (24.3). The title compound was prepared according to the method described for preparing compound 10.6, using compound 24.2 as the starting material. $^1$H NMR (400 MHz) (CDCl$_3$) δ 7.54 (2H, d, J=8.8 Hz); 7.42 (1H, d, J=1.6 Hz); 7.34 (1H, s); 7.06 (1H, dd, J=1.8, 8.2 Hz); 6.99 (2H, d, J=8.7 Hz); 6.67 (1H, s); 6.51 (1H, d, J=8.2 Hz); 4.99 (2H, s); 4.68 (2H, s); 4.30 (2H, q, J=7.1 Hz); 2.31 (3H, s); 2.25 (3H, s); 1.32 (3H, t, J=7.2 Hz).

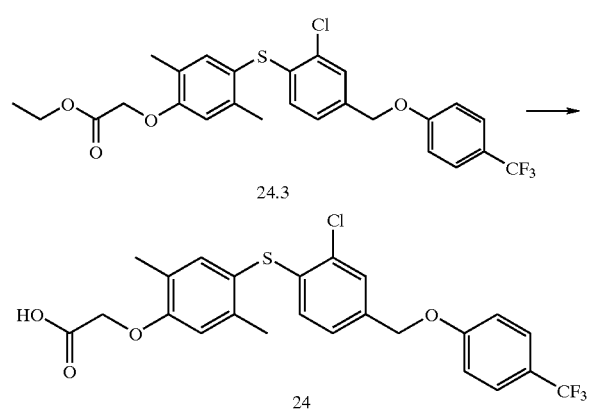

{4-[2-Chloro-4-(4-trifluoromethyl-phenoxymethyl)-phenylsulfanyl]-2,5-dimethyl-phenoxy}-acetic acid (24). The title compound was prepared according to the method described for preparing compound 7, using compound 24.3 as the starting material. MS APSI m/e: 495 (M−H). $^1$H NMR (400 MHz) (DMSO-d$_6$) δ 12.97 (1H, brs); 7.66 (2H, d, J=8.8 Hz); 7.59 (1H, d, J=1.5 Hz); 7.35 (1H, s); 7.28 (1H, dd, J=1.4, 8.0 Hz); 7.17 (2H, d, J=8.8 Hz); 6.97 (1H, s); 6.49 (1H, d, J=8.0 Hz); 5.12 (2H, s); 4.78 (2H, s); 2.24 (3H, s); 2.17 (3H, s).

Example 29

This example describes in vitro assays that were used or can be used to evaluate compounds of the invention.

Transient Transfection Assay

CV-1 cells were plated in DME medium supplemented with 10% charcoal stripped calf serum (HyClone) at a density of 24,000 cells per well in a 96-well plate (Costar) 16–24 h before transfection. Approximately 16 ng of luciferase reporter plasmid, 8 ng of a control β-galactosidase expression vector (pCMVβ, Clontech), and 2–8 ng of PPAR expression plasmid were mixed with carrier DNA (pBluescript, Stratagene) to a total of 80 ng per well in a volume of 10 μL of OptiME medium (GIBCO BRL). To this mixture was added a second mix containing 10 μL of OptiME medium and 0.7 μL of LipoFectamine (GIBCO BRL). After incubation for 30 min, an additional 80 μL of OptiME medium was added and the resulting solution was then applied to the cells. After 16 h the medium was exchanged to DME medium supplemented with 10% dilipidated fetal calf serum (Sigma) and test compound [concentrations ranging from 10 μM to 0.1 nM]. After incubation for an additional 24 h, the cells were lysed and both luciferase and β-galactosidase activity were measured. Luciferase activity was normalized for transfection efficiency by using β-galactosidase derived from the cotransfected pCMVβ plasmid as internal standard.

Plasmids

DR1$_{3X}$tk-luc reporter plasmids contain three copies of the consensus direct repeat 1 (DR1) PPAR response element [TATCA AGGTCA A AGGTCA TCTAG] inserted upstream of minimal herpes simplex thymidine kinase promoter in the pGL3 firefly luciferase reporter plasmid (Invitrogen).

G5 tk-luc contains 5 copies of the GAL4 binding site inserted upstream of minimal herpes simplex thymidine kinase promoter in the pGL3 firefly luciferase reporter plasmid.

pSG5huPPARδ and pSG5muPPARδ contain the nucleotide sequences for the human and murine PPARδ gene inserted into the expression vector pSG5 (Stratagene).

Plasmids containing nucleotide sequences encoding the ligand binding domains of human PPARα and human PPARγ inserted C-terminal to the GAL4 DNA binding domain of a suitable GAL4 DNA binding domain cloning vector can be prepared using conventional techniques.

Binding Assay

Compounds can be tested for their ability to bind to PPARα, PPARγ or PPARδ using a Scintillation Proximity Assay (SPA). Polylysine coated yttrium silicate SPA beads (Amersham) can be reconstituted by adding 200 ng beads to 40 μL assay buffer [20 mM phosphate buffer pH 7.1, 50 mM sodium chloride, 2 mM EDTA, 10% (v/v) glycerol, and 2 mM 3-[(3-cholamidopropyl)-dimethylammonio]-1-propanesulfonate (CHAPS)]. To the bead slurry, 80–280 ng of GST-PPAR protein can be added and the mixture incubated for 2 h at 4° C. The 40 μL of bead slurry can be added to 10 μL of test compound solution (concentrations ranging from 10 μM to 0.1 nM). Following incubation for 1 h at room temperature, 50 μL of a 20–40 nM radioligand solution in assay buffer can be added. After incubation for an additional 1 h at room temperature the assay mix can be quantitated using a Topcount (Packard).

Radioligands

For PPARδ and PPARα binding assays, radiolabeled 2-(4-(3-(1-((2-chloro-6-fluoro-phenyl)ethyl)-3-(2,3-dichlorophenyl)ureido)propenyl)phenoxy)-2-methylpropionic acid (Brown et al. (1997) *Chem. Biol.* 12:909–918) can be used. For PPARγ binding assay radiolabeled 5-{4-[2-(methyl-pyridine-2-yl-amino)-ethoxy]-benzyl}-thiazolidine-2,4-dione (described in U.S. Pat. No. 5,902,726) can be used.

Proteins

For GST-PPARα and GST-PPARγ, cDNAs encoding amino acids 167–468 of PPARα and amino acids 175 to 475 of PPARγ, respectively, can be inserted into the bacterial expression vector pGEX 2T (Pharmacia). For GST-PPARδ, cDNA encoding amino acids 138–440 can be inserted into the bacterial expression vector pGEX 6P-1 (Pharmacia). GST-PPAR ligand binding domain protein can be expressed in BL21 (DE3) cells (Stratagene).

iNOS Inhibition Assay

Compounds can be tested for their ability to inhibit the activity and/or expression of iNOS using lipopolysaccharide (LPS) to induce iNOS expression in the mouse macrophage cell line, J774. See, for example, International Publication No. WO 02/28434 to Buchan et al.

Measurement of iNOS Activity

LPS-induced iNOS activity can be measured using the following assay conditions: J774 cells are seeded at a density of 35000–50000 thousand cells per well, in a black, clear-bottomed, 96-well plate, 24 h prior to use. The cell culture and the drug dilutions are carried out in complete media, which consists of DMEM (Dulbecco's modification of Eagle's medium) containing fetal calf serum (10%), glutamine (2 mM), penicillin (100 u/mL) and streptomycin (100 μg/mL). The J774 cells are pre-treated with PPARδ activators or vehicle, for 6 h prior to, and for 24 h subsequent to, the addition of LPS. Twenty-four hours after the addition of LPA, iNOS activity is measured using the following method: The cell culture media/drug dilutions are removed and the cells washed with D-PBS (Dulbecco's modification of phosphate-buffered saline). The D-PBS is then removed, and replaced with D-PBS containing DAF-2 (4,5-diaminofluorescein; 5 μM) and L-arginine (500 μM). After incubation at 37° C. for 3 h, fluorescence from each well is measured at an excitation wavelength of 485 nm and an emission wavelength of 530 nm. The ability of LPS to induce iNOS activity, in the presence and absence of a PPARδ activator, can then be calculated.

Measurement of Inhibition of iNOS mRNA

LPS-induced expression of iNOS mRNA can be measured using the following assay conditions: J774 cells can be plated in 6-well plates ($10^6$ cells/well), 24 h prior to use. The cells can be pre-treated with PPARδ activator control media for 6 h, prior to addition of LPS, which can be co-incubated with the PPARδ activator/control for a further 24 h. At the end of this incubation period, the culture medium can be removed by aspirating and the cells washed with D-PBS. Following removal of the D-PBS, total cellular RNA can be isolated from each sample using a commercially available RNA isolation kit. First strand cDNA synthesis can be carried out as per instructions supplied with the AMV reverse transcription (RT) system. An aliquot (100 ng) of the RNA can be added to a mixture which contains (final concentrations) $MgCl_2$ (5 mM), Tris-HCl (10 mM; pH 8.8), KCl (50 mM), Triton X-100 (0.1%), dNTP (1 mM), rRNasin (1 U/μL), AMV reverse transcriptase (0.75 U/μL), oligo(dT)$_{15}$ (25 ng/μL). The resulting mixture can be incubated in a thermal cycler at 42° C. for 30 min, followed by 95° C. for 15 min, and, finally, 4° C., until being transferred to a freezer (−20° C.) for storage.

For use in PCR, mouse iNOS sense, mouse iNOS anti-sense, mouse GAPDH sense and mouse GAPDH anti-sense primer sets, such as those used in International Publication No. WO 02/28434 to Buchan et al., can be used. PCR can be undertaken in a 50-μL reaction volume containing 5 μL of the RT reaction, sense and anti-sense primers for iNOS/GAPDH (0.4 pmol/μL), dNTPs (160 mM), KCl (50 mM), Tris-HCl (10 mM; pH 9.0), Triton X-100 (0.1%), $MgCl_2$ (2 mM) and Taq DNA polymerase (0.04 U/μL) (final concentrations). The PCR can be carried out in a thermal cycler using the following conditions: 95° C. for 60 s, followed by 28 cycles of 94° C. for 30 s, 55° C. for 60 s, 72° C. for 90 s. Following a final extension step of 72° C. for 5 min, the samples can be maintained at 4° C. until analyzed on an agarose gel. Analysis of sybr-green-stained gels, by densitometry, can be carried out using a Storm fluorimager system (Molecular Devices).

Measurement of Inhibition of TNF

LPS-induced iNOS activity and expression of TNF can be measured using the following assay conditions: J774 cells can be seeded at a density of 35000–50000 thousand cells per well, in black, clear-bottomed, 96-well plates. The cell culture and the drug dilutions can be carried out in complete media, which consists of DMEM (Dulbecco's modification of Eagle's medium) containing fetal calf serum (10%), glutamine (2 mM), penicillin (100 u/mL) and streptomycin (100 μg/mL). The J774 cells can be pre-treated with PPARδ activators, or vehicle, for 6 h prior to, and for 24 h subsequent to the addition of LPS. Twenty-four hours after the addition of LPS, iNOS activity can be measured by the following method: The cell culture media/drug dilutions can be removed for measurement of TNF concentrations, and quantified using a commercially available ELISA system. The cells can be washed with D-PBS. The D-PBS can then be removed, and replaced with D-PBS containing DAF-2 (4,5-diaminofluorescein; 5 μM) and L-arginine (500 μM). INOS activity can then be measured as described above.

Example 30

This example describes an in vivo assay used to evaluate compounds of the invention.

HDL Cholesterol Assay in High Cholesterol Fed Rats

Male Sprague-Dawley rats (BW: 100–120 g) were fed a high cholesterol diet (1.25% cholesterol, 0.5% cholic acid and 10% coconut oil) for 14 days. The animals were orally dosed with test compounds suspended to 0.5% methylcellulose solution once a day over the final 7 days. Typical doses of test compounds were 1–30 mg/kg/day.

After 7 days of treatment, serum HDL cholesterol concentration was determined from blood obtained by tail bleeds. HDL cholesterol determination was performed on a Hitachi 7170 automatic analyzer. Data for selected compounds of the invention are summarized in Table 9.

TABLE 9

Serum HDL cholesterol levels (% of increase) determined for selected compounds of the invention.

| Compound | % of increase at 30 mg/kg |
| --- | --- |
| 1 | ++ |
| 2 | ++ |
| 3 | + |
| 4 | ++ |
| 5 | + |
| 6 | ++ |
| 7 | + |
| 8 | ++ |
| 9 | + |
| 10 | + |
| 11 | ++ |
| 21 | ++ |
| 22 | + |
| 25 | ++ |
| 26 | + |
| 27 | + |

++ denotes greater than 100%
+ denotes 100% or less

Serum HDL cholesterol level (% of increase) refers to the rate of HDL increase relative to the vehicle and was calculated as follows:

$$\frac{\text{test compound HDL cholesterol (mg/dl)} - \text{vehicle HDL cholesterol (mg/dl)}}{\text{vehicle HDL cholesterol (mg/dl)}} \times 100$$

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A compound having the formula (Ia):

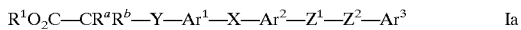
$$R^1O_2C\text{—}CR^aR^b\text{—}Y\text{—}Ar^1\text{—}X\text{—}Ar^2\text{—}Z^1\text{—}Z^2\text{—}Ar^3 \quad \text{Ia}$$

or a pharmaceutically acceptable salt or prodrug thereof, wherein

X is selected from the group consisting of $S(O)_m$, CR'R" and $SO_2NR$";

Y is O or CR'R";

$Z^1$ and $Z^2$ are independently selected from the group consisting of O, $S(O)_m$, $(CR'R")_n$, N(R'), C(O)NR" and CR'R"C(O)NR'";

alternatively, $Z^1$ and $Z^2$ may be combined to form $(C_2\text{–}C_4)$alkenyl;

$Ar^1$ and $Ar^2$ are independently an aromatic group;

$Ar^3$ is aryl;

$R^1$ is selected from the group consisting of hydrogen, $(C_1\text{–}C_8)$alkyl and aryl$(C_1\text{–}C_4)$alkyl;

$R^a$ and $R^b$ are independently selected from the group consisting of hydrogen, $(C_1\text{–}C_4)$alkyl, aryl and aryl $(C_1\text{–}C_4)$alkyl;

each R', R" and R'" is independently selected from the group consisting of hydrogen, $(C_1\text{–}C_4)$alkyl, aryl and aryl$(C_1\text{–}C_4)$alkyl;

the subscript m is an integer from 0 to 2; and the subscript n is an integer from 1 to 2.

2. A compound having the formula (Ia):

$$R^1O_2C\text{—}CR^aR^b\text{—}Y\text{—}Ar^1\text{—}X\text{—}Ar^2\text{—}Z^1\text{—}Z^2\text{—}Ar^3 \quad \text{Ia}$$

or a pharmaceutically acceptable salt or prodrug thereof, wherein

X is S;

Y is O;

$Z^1$ is $(CR'R")_n$;

$Z^2$ is O;

$Ar^1$ and $Ar^2$ are independently phenyl;

$Ar^3$ is phenyl; and $R^1$ is selected from the group consisting of hydrogen, $(C_1\text{–}C_8)$alkyl and aryl$(C_1\text{–}C_4)$alkyl;

$R^a$ and $R^b$ are independently selected from the group consisting of hydrogen, $(C_1\text{–}C_4)$alkyl, aryl and aryl $(C_1\text{–}C_4)$alkyl;

each R' and R" and is independently selected from the group, consisting of hydrogen, $(C_1\text{–}C_4)$alkyl, aryl and aryl$(C_1\text{–}C_4)$alkyl; and the subscript n is an integer from 1 to 2.

3. The compound of claim 2, having the formula (Ib):

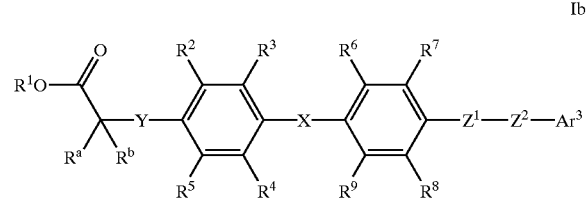

wherein $R^2$, $R^3$, $R^4$, $R^5$, $R^6$, $R^7$, $R^8$ and $R^9$ are independently selected from the group consisting of hydrogen, halogen, $(C_1\text{–}C_4)$alkyl, $(C_5\text{–}C_6)$cycloalkyl, fluoro $(C_1\text{–}C_4)$alkyl, OR', aryl, aryl$(C_1\text{–}C_4)$alkyl, $NO_2$, NR'R", C(O)R', $CO_2R$, C(O)NR'R", N(R")C(O)R', $N(R")CO_2R'$, N(R")C(O)NR'R", $S(O)_mNR'R"$, $S(O)_mR'$, CN and $N(R")S(O)_mR'$;

optionally, when R' and R" are attached to the same nitrogen atom, R' and R" may be combined with the nitrogen atom to form a 5-, 6- or 7-membered ring containing from 1 to 3 heteroatoms selected from the group consisting of N, O and S; and optionally, any two adjacent R groups selected from the group consisting of $R^2$, $R^3$, $R^4$, $R^5$, $R^6$, $R^7$, $R^8$ and $R^9$ may be combined with the carbon atoms to which they are attached to form a fused aromatic or cycloalkane ring.

4. The compound of claim 3, wherein $R^a$ and $R^b$ are both hydrogen or methyl.

5. The compound of claim 3, having the formula (II):

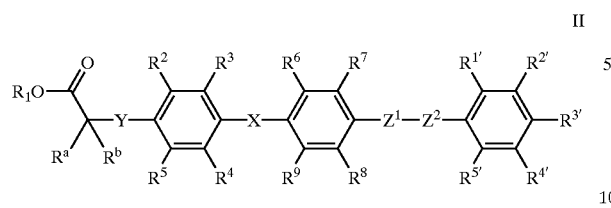

wherein

R$^{1'}$, R$^{2'}$, R$^{3'}$, R$^{4'}$ and R$^{5'}$ are independently selected from the group consisting of hydrogen, halogen, (C$_1$–C$_4$) alkyl, fluoro(C$_1$–C$_4$)alkyl, OR', aryl, aryl(C$_1$–C$_4$)alkyl, NO$_2$, NR'R", C(O)R', CO$_2$R', C(O)NR'R", N(R")C(O) R', N(R")CO$_2$R', N(R")C(O)NR'R", S(O)$_m$NR'R", S(O)$_m$R', CN and N(R")S(O)$_m$R'.

6. The compound of claim 5, wherein at least one of R$^{1'}$, R$^{2'}$, R$^{3'}$, R$^{4'}$ and R$^{5'}$ is not hydrogen.

7. The compound of claim 5, wherein at least one of R$^{1'}$, R$^{2'}$, R$^{3'}$, R$^{4'}$ and R$^{5'}$0 is fluoro(C$_1$–C$_4$)alkyl.

8. The compound of claim 7, wherein R$^{3'}$ is CF$_3$.

9. The compound of claim 7, wherein R$^{4'}$ is CF$_3$.

10. The compound of claim 7, wherein R$^{5'}$ is CF$_3$.

11. The compound of claim 3, wherein Z$^1$ is CH$_2$.

12. The compound of claim 2, or a pharmaceutically acceptable salt or prodrug thereof, wherein said compound is selected from the group consisting of:

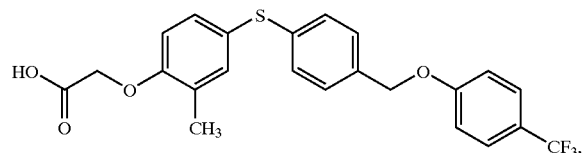

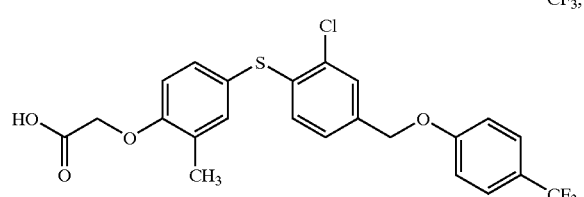

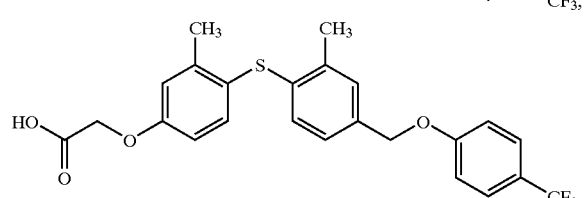

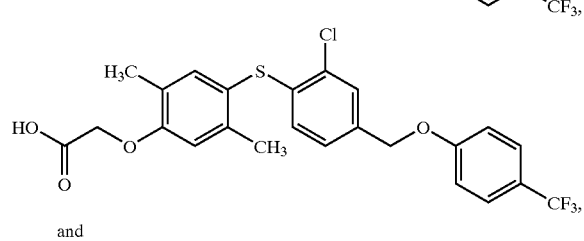

and

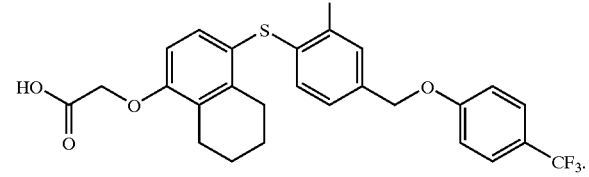

13. The compound of claim 3, wherein

R$^2$, R$^3$, R$^4$, R$^5$, R$^6$, R$^7$, R$^8$ and R$^9$ are independently selected from the group consisting of hydrogen, halogen and (C$_1$–C$_4$)alkyl and (C$_5$–C$_6$)cycloalkyl;

optionally, any two adjacent R groups selected from the group consisting of R$^2$, R$^3$, R$^4$, R$^5$, R$^6$, R$^7$, R$^8$ and R$^9$ may be combined with the carbon atoms to which they are attached to form a fused benzene or cyclohexane ring; and R$^a$ and R$^b$ are hydrogen.

14. The compound of claim 3, wherein

R$^1$ is hydrogen;

R$^2$, R$^3$, R$^4$, R$^6$ and R$^7$ are independently selected from the group consisting of hydrogen, chlorine, methyl, ethyl, n-propyl, isopropyl and cyclopentyl;

optionally, R$^2$ and R$^3$ are combined with the carbon atoms to which they are attached to form a fused benzene or cyclohexane ring;

optionally, R$^6$ and R$^7$ are combined with the carbon atoms to which they are attached to form a fused benzene ring;

R$^5$, R$^8$ and R$^9$ are each hydrogen; and

R$^a$ and R$^b$ are hydrogen.

15. A pharmaceutical composition comprising a pharmaceutically acceptable carrier, excipient, or diluent and a compound according to claim 1.

16. A method for treating a metabolic disorder disease comprising administering to a subject in need thereof a therapeutically effective amount of a compound according to claim 1 (having the formula (Ia).

17. The method of claim 16, wherein said metabolic disorder is selected from the group consisting of hypercholesterolemia, hyperlipidemia, dyslipidemia, hypertriglylceridemia, hyperglycemia, diabetes, obesity, syndrome X, insulin resistance, hyperinsulinemia and an eating disorder.

18. The method of claim 16, wherein the subject is a human.

19. The compound of claim 12 selected from the group consisting of:

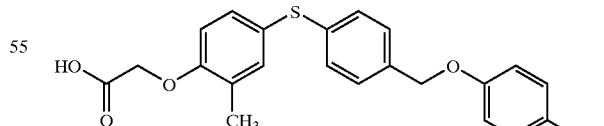

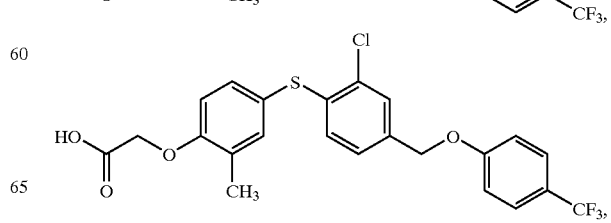

-continued

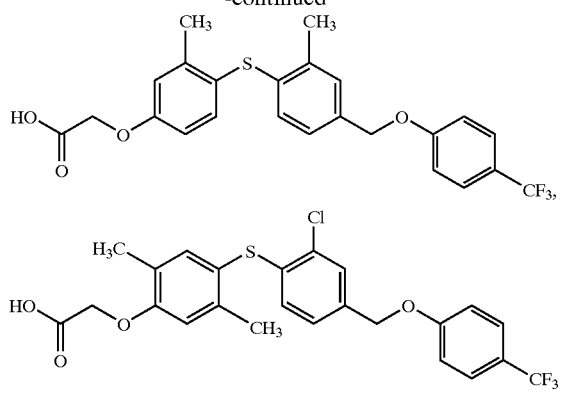

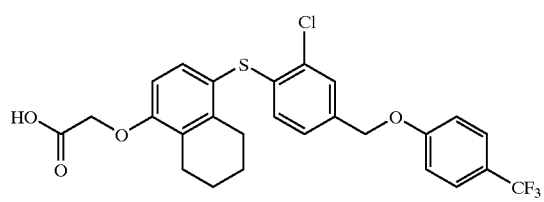

and

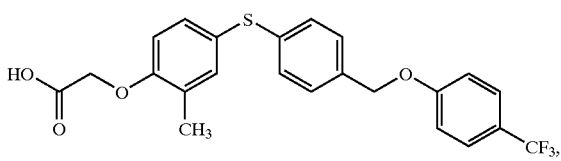

or a pharmaceutically acceptable salt thereof.

20. The pharmaceutical composition of claim 15 wherein
X is S;
Y is O;
$Z^1$ is $(CR'R'')_n$;
$Z^2$ is O;
$Ar^1$ and $Ar^2$ are independently phenyl; and
$Ar^3$ is phenyl.

21. The pharmaceutical composition of claim 15 wherein said compound is selected from the group consisting of:

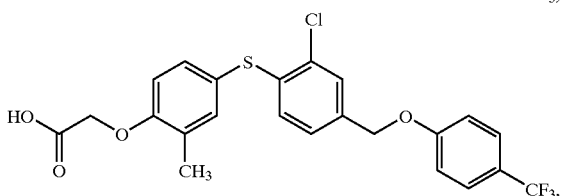

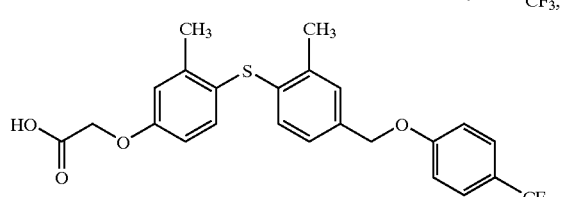

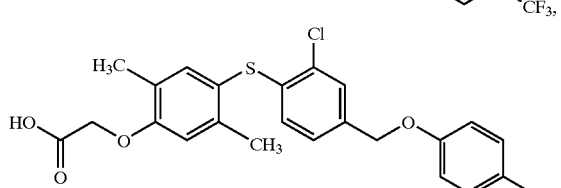

and

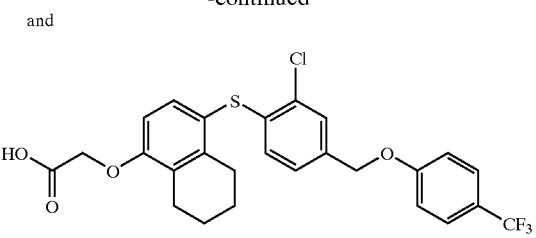

or a pharmaceutically acceptable salt or prodrug thereof.

22. The pharmaceutical composition according to claim 15 comprising a compound having the formula (Ia), or a pharmaceutically acceptable salt thereof.

23. The pharmaceutical composition of claim 21 wherein said compound is selected from the group consisting of:

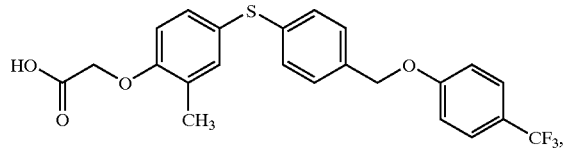

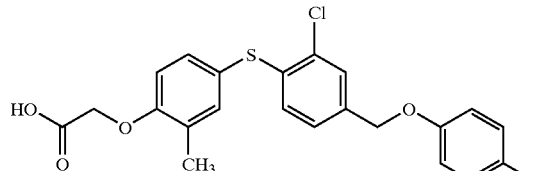

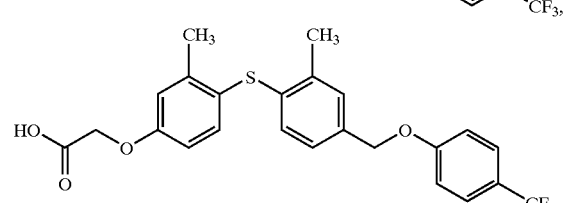

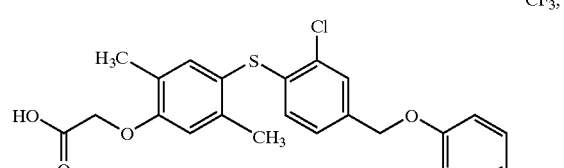

and

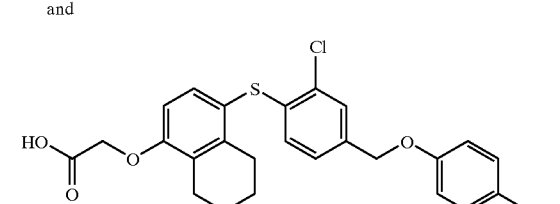

or a pharmaceutically acceptable salt thereof.

24. The method of claim 16 wherein the compound has formula (Ia), or a pharmaceutically acceptable salt thereof.

25. The method of claim 16 wherein
X is S;
Y is O;
$Z^1$ is $(CR'R'')_n$;
$Z^2$ is O;
$Ar^1$ and $Ar^2$ are independently phenyl; and
$Ar^3$ is phenyl.

26. The method of claim 16 wherein said compound is selected from the group consisting of:
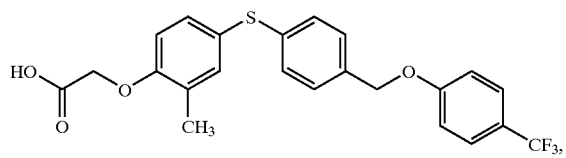
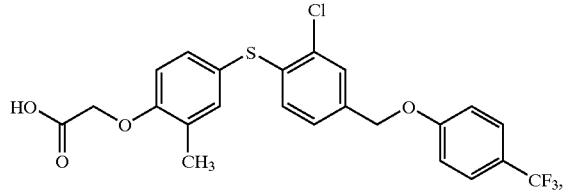
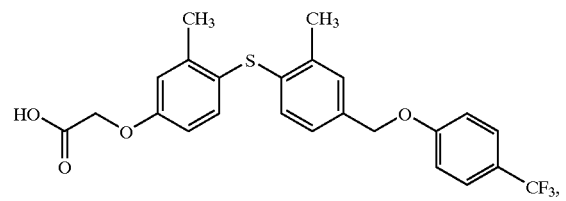
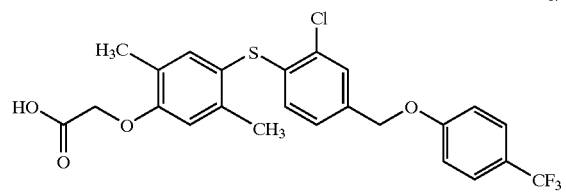
and
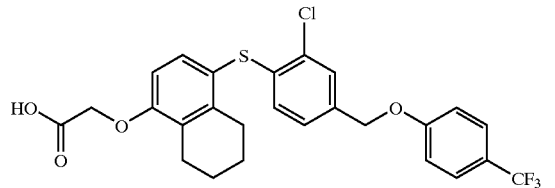
or a pharmaceutically acceptable salt or prodrug thereof.
27. The method of claim 26, wherein the subject is a human.
28. The method of claim 26 wherein said compound is selected from the group consisting of:
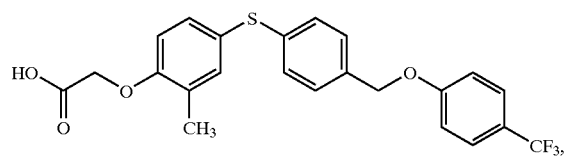
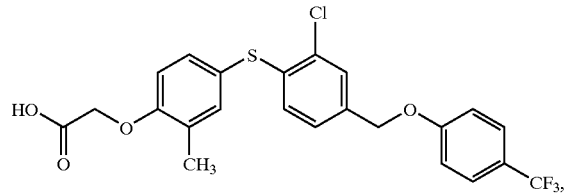
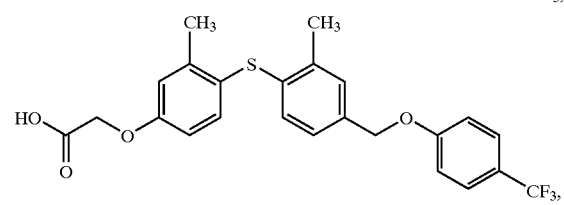
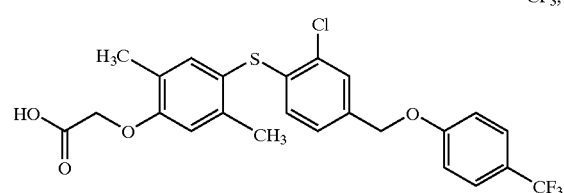
and
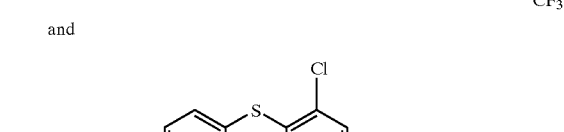
or a pharmaceutically acceptable salt thereof.
* * * * *

UNITED STATES PATENT AND TRADEMARK OFFICE
CERTIFICATE OF CORRECTION

PATENT NO. : 6,869,975 B2
DATED : May 3, 2005
INVENTOR(S) : Hiroyuki Abe et al.

It is certified that error appears in the above-identified patent and that said Letters Patent is hereby corrected as shown below:

Column 64,
Line 6, "formula_(la):" should be changed to -- formula (la): --.

Column 65,
Line 26, "$R^{5'}0$" should be changed to -- $R^{5'}$ --.

Column 66,
Line 39, "metabolic disorder disease" should be changed to -- metabolic disorder --;
Line 42, "claim 1 (having the formula (la)." should be changed to -- claim 1. --.

Signed and Sealed this

Thirtieth Day of August, 2005

JON W. DUDAS
*Director of the United States Patent and Trademark Office*